(12) United States Patent
Johnson et al.

(10) Patent No.: US 6,613,915 B1
(45) Date of Patent: Sep. 2, 2003

(54) POLYMERIZATION OF OLEFINS

(75) Inventors: Lynda Kaye Johnson, Wilmington, DE (US); Alison Margaret Anne Bennett, Wilmington, DE (US); Lin Wang, Hockessin, DE (US); Anju Parthasarathy, Glenmoore, PA (US); Elisabeth Hauptman, Wilmington, DE (US); Robert D. Simpson, Philadelphia, PA (US); Jerald Feldman, Hockessin, DE (US); Edward Bryan Coughlin, Wilmington, DE (US); Steven Dale Ittel, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 180 days.

(21) Appl. No.: 09/417,323

(22) Filed: Oct. 13, 1999

Related U.S. Application Data

(62) Division of application No. 09/006,536, filed on Jan. 13, 1998, now Pat. No. 6,174,975.
(60) Provisional application No. 60/035,190, filed on Jan. 14, 1997.

(51) Int. Cl.$^7$ .................. C07F 15/04; C07D 207/30; B01J 31/00
(52) U.S. Cl. .................. 548/402; 548/561; 548/564; 556/138; 402/162

(58) Field of Search .................. 556/138; 548/402, 548/561, 564; 502/162

(56) References Cited

U.S. PATENT DOCUMENTS

| 5,395,811 A | 3/1995 | Novak et al. ............ 502/152 |
| 5,714,556 A | 2/1998 | Johnson et al. ............ 526/135 |
| 5,986,027 A | 11/1999 | Lippert et al. ............ 526/126 |

FOREIGN PATENT DOCUMENTS

| DE | 44 15 725 C2 | 8/1997 |
| WO | WO 96/23010 | 8/1996 |
| WO | WO 98/42664 | 10/1998 |

OTHER PUBLICATIONS

Raghavendra et al., Inorganica Chimica Acta, vol. 18, pp. 257–261 (1976).*
Brunner et al., Journal of Organometallic Chemistry, vol. 64, pp. 373–383 (1974).*

* cited by examiner

*Primary Examiner*—Porfirio Nazario-Gonzalez

(57) ABSTRACT

Selected olefins such as ethylene and α-olefins are polymerized by nickel [II] complexes of certain monoanionic ligands. The polyolefins are useful in many applications such as molding resins, film, fibers and others. Also described are many novel nickel compounds and their precursors, as well a novel ligands.

35 Claims, No Drawings

POLYMERIZATION OF OLEFINS

This application claims the benefit of U.S. Provisional Application No. 60/035,190, filed Jan. 14, 1997. This is a division of application Ser. No. 09/006,536 filed Jan. 13, 1998, now U.S. Pat. No. 6,174,975.

FIELD OF THE INVENTION

Olefins are polymerized by a catalyst system that includes a nickel[II] complexes of selected monoanionic bidentate ligands. Some of these complexes are also novel.

TECHNICAL BACKGROUND

Polymers of ethylene and other olefins are important items of commerce, and these polymers are used in a myriad of ways, from low molecular weight polyolefins being used as a lubricant and in waxes, to higher molecular weight grades being used for fiber, films, molding resins, elastomers, etc. In most cases, olefins are polymerized using a catalyst, often a transition metal compound or complex. These catalysts vary in cost per unit weight of polymer produced, the structure of the polymer produced, the possible need to remove the catalyst from the polyolefin, the toxicity of the catalyst, etc. Due to the commercial importance of polymerizing olefins, new polymerization catalysts are constantly being sought.

SUMMARY OF THE INVENTION

This invention concerns a process for the polymerization of an olefin selected from one or more of $R^{67}CH{=}CH_2$, cyclopentene, a styrene, a norbornene or $H_2C{=}CH(CH_2)_s CO_2R^{77}$, comprising, contacting, at a temperature of about $-100°$ C. to about $+200°$ C., $R^{67}CH{=}CH_2$, cyclopentene, a styrene, a norbornene, or $H_2C{=}CH(CH_2)_s CO_2R^{77}$, optionally a Lewis acid, and a compound of the formula:

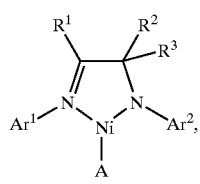

(I)

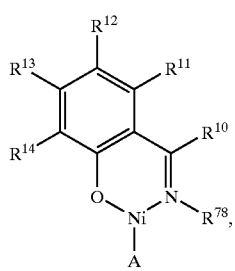

(II)

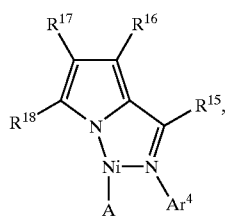

(III)

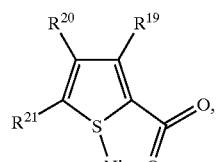

(IV)

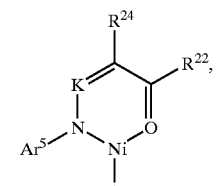

(V)

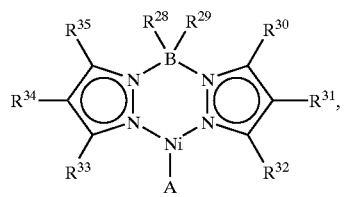

(VI)

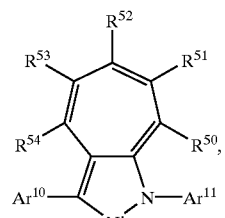

(XVIII)

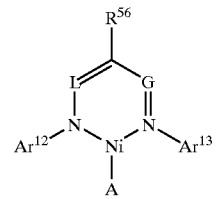

(XXVII)

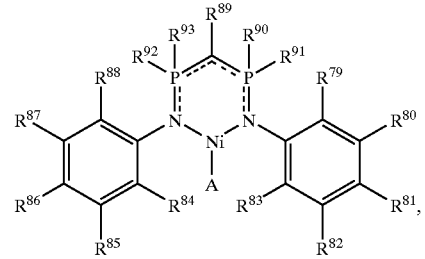

(XXXVII)

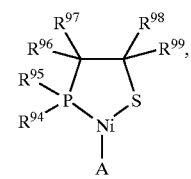

(XXXVIII)

-continued

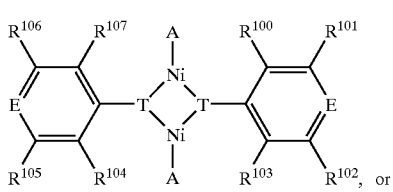

(XXXIX)

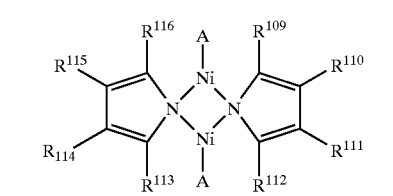

(XXXX)

wherein:

$Ar^1$, $Ar^2$, $Ar^4$, $Ar^5$, $Ar^{10}$, $Ar^{11}$, $Ar^{12}$ and $Ar^{13}$ are each independently aryl or substituted aryl;

$R^1$ and $R^2$ are each independently hydrogen, hydrocarbyl, substituted hydrocarbyl, or $R^1$ and $R^2$ taken together form a ring, and $R^3$ is hydrogen, hydrocarbyl or substituted hydrocarbyl or $R^1$, $R^2$ and $R^3$ taken together form a ring;

A is a π-allyl or π-benzyl group;

$R^{10}$ and $R^{15}$ are each independently hydrogen, hydrocarbyl or substituted hydrocarbyl;

$R^{11}$, $R^{12}$, $R^{13}$, $R^{14}$, $R^{16}$, $R^{17}$, $R^{18}$, $R^{19}$, $R^{20}$, $R^{21}$, $R^{30}$, $R^{31}$, $R^{32}$, $R^{33}$, $R^{34}$, $R^{35}$, $R^{50}$, $R^{51}$, $R^{52}$, $R^{53}$ and $R^{54}$ are each independently hydrogen, hydrocarbyl, substituted hydrocarbyl, an inert functional group, and provided that any two of these groups vicinal to one another taken together may form a ring;

K is N or $CR^{27}$;

$R^{22}$ is hydrocarbyl, substituted hydrocarbyl, —$SR^{117}$, —$OR^{117}$, or —$NR^{118}{}_2$, $R^{24}$ is hydrogen, a functional group, hydrocarbyl or substituted hydrocarbyl, and $R^{27}$ is hydrocarbyl or substituted hydrocarbyl, and provided that $R^{22}$ and R or $R^{24}$ and $R^{27}$ taken together may form a ring;

$R^{117}$ is hydrocarbyl or substituted hydrocarbyl;

each $R^{118}$ is independently hydrogen, hydrocarbyl or substituted hydrocarbyl;

G and L are both N or G is $CR^{57}$ and L is $CR^{55}$;

$R^{55}$, $R^{56}$ and $R^{57}$ are each independently hydrogen, hydrocarbyl or substituted hydrocarbyl, or any two of $R^{55}$, $R^{56}$ and $R^{57}$ taken together form a ring;

$R^{67}$ is hydrogen, alkyl or substituted alkyl;

$R^{77}$ is hydrocarbyl or substituted hydrocarbyl;

$R^{78}$ is hydrocarbyl or substituted hydrocarbyl;

$R^{79}$, $R^{80}$, $R^{81}$, $R^{82}$, $R^{83}$, $R^{84}$, $R^{85}$, $R^{86}$, $R^{87}$, $R^{88}$ and $R^{89}$ are each independently hydrogen, hydrocarbyl, substituted hydrocarbyl, or a functional group;

$R^{90}$, $R^{91}$, $R^{92}$ and $R^{93}$ are each independently hydrocarbyl or substituted hydrocarbyl;

$R^{94}$ and $R^{95}$ are each independently hydrocarbyl or substituted hydrocarbyl;

$R^{96}$, $R^{97}$, $R^{98}$, and $R^{99}$ are each independently hydrogen, hydrocarbyl, substituted hydrocarbyl or a functional group;

both of T are S (sulfur) or NH (amino);

each E is N (nitrogen) or $CR^{108}$ wherein $R^{108}$ is hydrogen, hydrocarbyl, substituted hydrocarbyl or a functional group;

$R^{100}$, $R^{101}$, $R^{102}$, $R^{103}$, $R^{104}$, $R^{105}$, $R^{106}$, and $R^{107}$ are each independently hydrogen, hydrocarbyl, substituted hydrocarbyl, or a functional group;

$R^{109}$, $R^{110}$, $R^{111}$, $R^{112}$, $R^{113}$, $R^{114}$, $R^{115}$ and $R^{116}$ are each independently hydrogen, hydrocarbyl, substituted hydrocarbyl or a functional group;

s is an integer of 1 or more; and $R^{28}$ and $R^{29}$ are each independently hydrogen, hydrocarbyl or substituted hydrocarbyl;

and provided that when $H_2C=CH(CH_2)_sCO_2R^{77}$ is present, $R^{67}CH=CH_2$ is also present.

This invention also concerns a process for the polymerization of an olefin selected from one or more of $R^{67}CH=CH_2$, a styrene, a norbornene or $H_2C=CH(CH_2)_sCO_2R^{77}$, comprising, contacting, at a temperature of about −100° C. to about +200° C., $R^{67}CH=CH_2$, cyclopentene, a styrene, a norbornene, or $H_2C=CH(CH_2)_sCO_2R^{77}$, optionally a Lewis acid, and a compound of the formula:

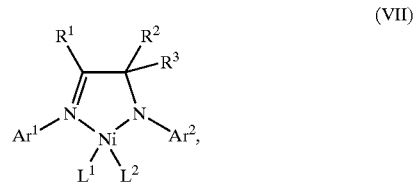

(VII)

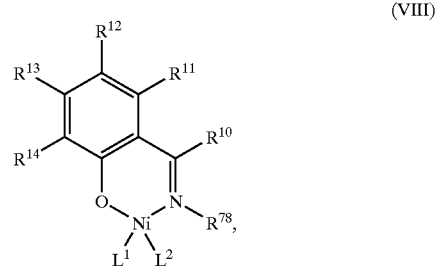

(VIII)

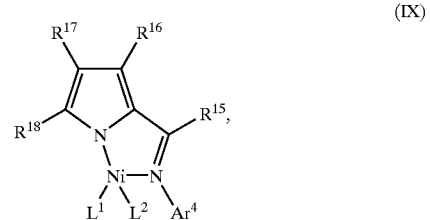

(IX)

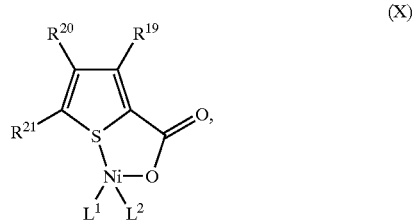

(X)

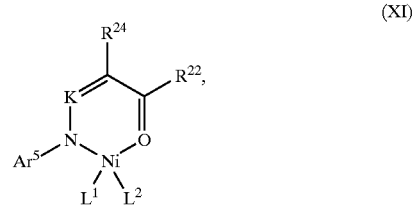

(XI)

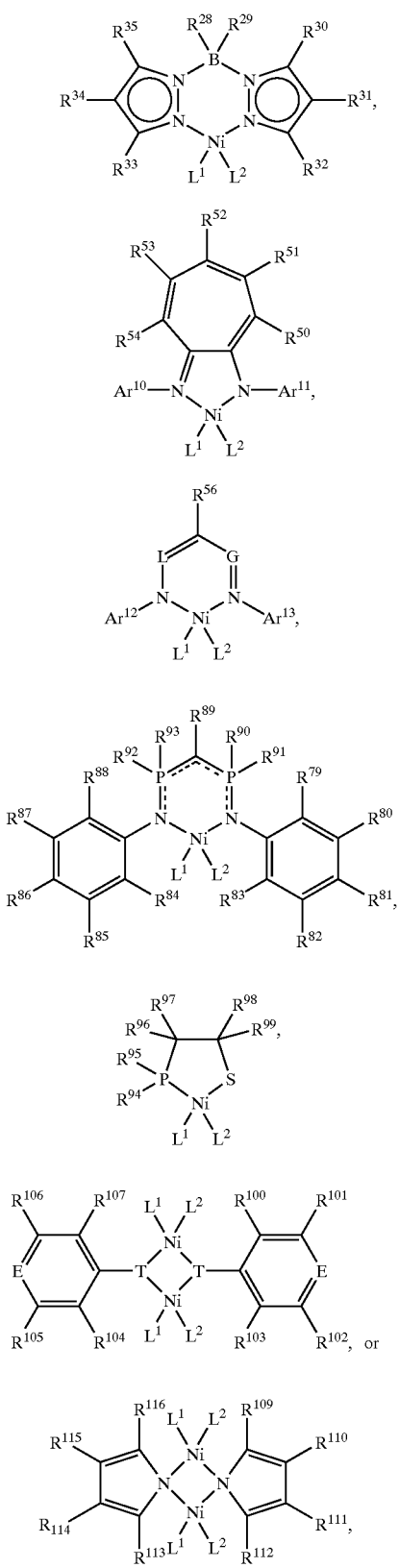

wherein:

L¹ is a neutral monodentate ligand which may be displaced by said olefin, and L² is a monoanionic monodentate ligand, or L¹ and L2 taken together are a monoanionic bidentate ligand, provided that said monoanionic monodentate ligand or said monoanionic bidentate ligand may add to said olefin;

$Ar^1$, $Ar^2$, $Ar^4$, $Ar^5$, $Ar^{10}$, $Ar^{11}$, $Ar^{12}$ and $Ar^{13}$ are each independently aryl or substituted aryl;

$R^1$ and $R^2$ are each independently hydrogen, hydrocarbyl, substituted hydrocarbyl, or $R^1$ and $R^2$ taken together form a ring, and $R^3$ is hydrogen, hydrocarbyl or substituted hydrocarbyl or $R^1$, $R^2$ and $R^3$ taken together form a ring;

$R^{10}$ and $R^{15}$ are each independently hydrogen, hydrocarbyl or substituted hydrocarbyl;

$R^{11}$, $R^{12}$, $R^{13}$, $R^{14}$, $R^{16}$, $R^{17}$, $R^{18}$, $R^{19}$, $R^{20}$, $R^{21}$, $R^{30}$, $R^{31}$, $R^{32}$, $R^{33}$, $R^{34}$, $R^{35}$, $R^{50}$, $R^{51}$, $R^{52}$, $R^{53}$ and $R^{54}$ are each independently hydrogen, hydrocarbyl, substituted hydrocarbyl, an inert functional group, and provided that any two of these groups vicinal to one another taken together may form a ring;

K is N or $CR^{27}$;

$R^{22}$ is hydrocarbyl, substituted hydrocarbyl, $-SR^{117}$, $-OR^{117}$, or $-NR^{118}_2$, $R^{24}$ is hydrogen, a functional group, hydrocarbyl or substituted hydrocarbyl, and $R^{27}$ is hydrocarbyl or substituted hydrocarbyl, and provided that $R^{22}$ and $R^{24}$ or $R^{24}$ and $R^{27}$ taken together may form a ring;

$R^{117}$ is hydrocarbyl or substituted hydrocarbyl;

each $R^{118}$ is independently hydrogen, hydrocarbyl or substituted hydrocarbyl;

G and L are both N or G is $CR^{57}$ and L is $CR^{55}$;

$R^{55}$, $R^{56}$ and $R^{57}$ are each independently hydrogen, hydrocarbyl or substituted hydrocarbyl, or any two of $R^{55}$, $R^{56}$ and $R^{57}$ taken together form a ring;

$R^{67}$ is hydrogen, alkyl or substituted alkyl;

$R^{77}$ is hydrocarbyl or substituted hydrocarbyl;

$R^{78}$ is hydrocarbyl or substituted hydrocarbyl;

$R^{79}$, $R^{80}$, $R^{81}$, $R^{82}$, $R^{83}$, $R^{84}$, $R^{85}$, $R^{86}$, $R^{87}$, $R^{88}$ and $R^{89}$ are each independently hydrogen, hydrocarbyl, substituted hydrocarbyl, or a functional group;

$R^{90}$, $R^{91}$, $R^{92}$ and $R^{93}$ are each independently hydrocarbyl or substituted hydrocarbyl;

$R^{94}$ and $R^{95}$ are each independently hydrocarbyl or substituted hydrocarbyl;

$R^{96}$, $R^{97}$, $R^{98}$, and $R^{99}$ are each independently hydrogen, hydrocarbyl, substituted hydrocarbyl or a functional group;

both of T are S (sulfur) or NH (amino);

each E is N (nitrogen) or $CR^{108}$ wherein $R^{108}$ is hydrogen, hydrocarbyl, substituted hydrocarbyl or a functional group;

$R^{100}$, $R^{101}$, $R^{102}$, $R^{103}$, $R^{104}$, $R^{105}$, $R^{106}$, and $R^{107}$ are each independently hydrogen, hydrocarbyl, substituted hydrocarbyl, or a functional group;

$R^{109}$, $R^{110}$, $R^{111}$, $R^{112}$, $R^{113}$, $R^{114}$, $R^{115}$ and $R^{116}$ are each independently hydrogen, hydrocarbyl, substituted hydrocarbyl or a functional group;

s is an integer of 1 or more; and $R^{28}$ and $R^{29}$ are each independently hydrogen, hydrocarbyl or substituted hydrocarbyl;

and provided that when $H_2C=CH(CH_2)_s CO_2R^{77}$ is present, $R^{67}CH=CH_2$ is also present.

Also described herein is a compound of the formula:

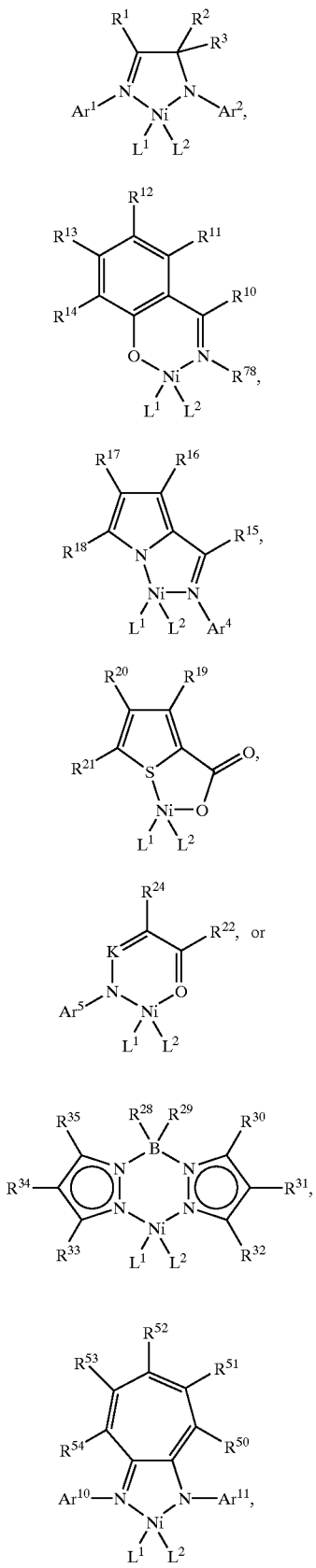

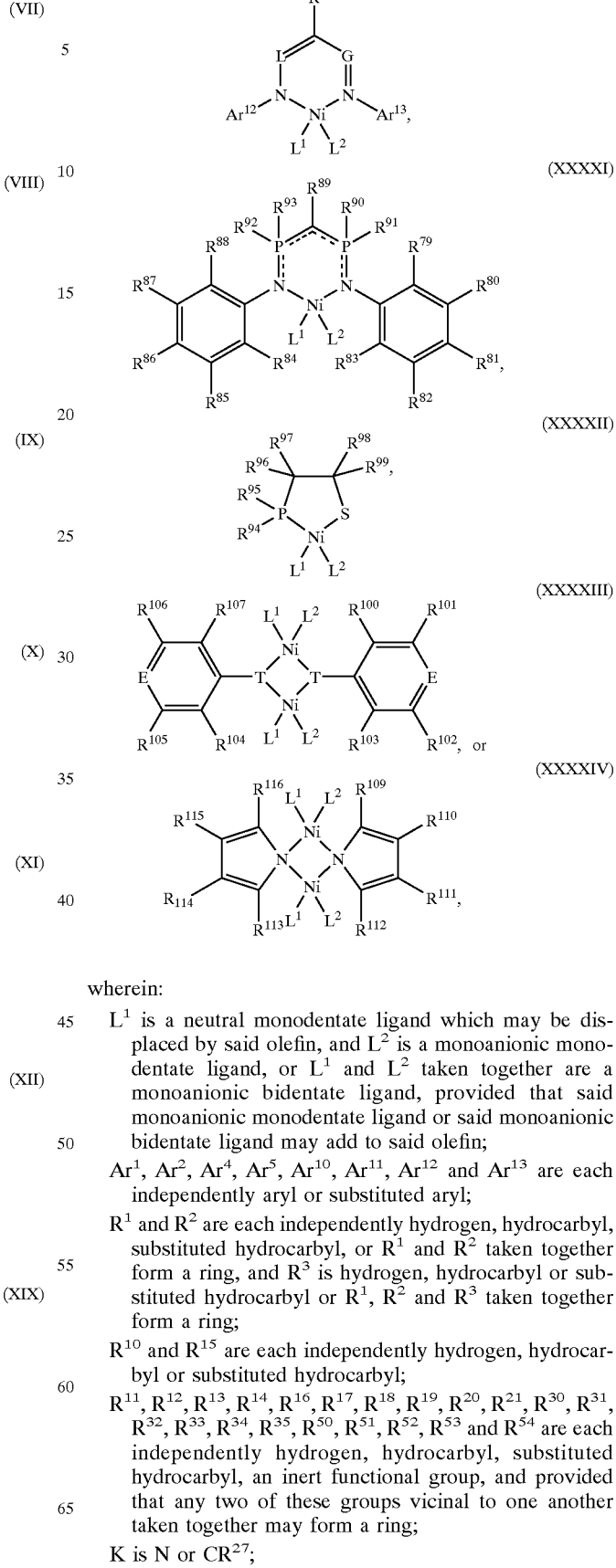

wherein:

L¹ is a neutral monodentate ligand which may be displaced by said olefin, and L² is a monoanionic monodentate ligand, or L¹ and L² taken together are a monoanionic bidentate ligand, provided that said monoanionic monodentate ligand or said monoanionic bidentate ligand may add to said olefin;

$Ar^1$, $Ar^2$, $Ar^4$, $Ar^5$, $Ar^{10}$, $Ar^{11}$, $Ar^{12}$ and $Ar^{13}$ are each independently aryl or substituted aryl;

$R^1$ and $R^2$ are each independently hydrogen, hydrocarbyl, substituted hydrocarbyl, or $R^1$ and $R^2$ taken together form a ring, and $R^3$ is hydrogen, hydrocarbyl or substituted hydrocarbyl or $R^1$, $R^2$ and $R^3$ taken together form a ring;

$R^{10}$ and $R^{15}$ are each independently hydrogen, hydrocarbyl or substituted hydrocarbyl;

$R^{11}$, $R^{12}$, $R^{13}$, $R^{14}$, $R^{16}$, $R^{17}$, $R^{18}$, $R^{19}$, $R^{20}$, $R^{21}$, $R^{30}$, $R^{31}$, $R^{32}$, $R^{33}$, $R^{34}$, $R^{35}$, $R^{50}$, $R^{51}$, $R^{52}$, $R^{53}$ and $R^{54}$ are each independently hydrogen, hydrocarbyl, substituted hydrocarbyl, an inert functional group, and provided that any two of these groups vicinal to one another taken together may form a ring;

K is N or $CR^{27}$;

$R^{22}$ is hydrocarbyl, substituted hydrocarbyl, —$SR^{117}$, —$OR^{117}$, or —$NR^{118}{}_2$, $R^{24}$ is hydrogen, a functional group, hydrocarbyl or substituted hydrocarbyl, and $R^{27}$ is hydrocarbyl or substituted hydrocarbyl, and provided that $R^{22}$ and $R^{24}$ or $R^{24}$ and $R^{27}$ taken together may form a ring;

$R^{117}$ is hydrocarbyl or substituted hydrocarbyl;

each $R^{118}$ is independently hydrogen, hydrocarbyl or substituted hydrocarbyl;

G and L are both N or G is $CR^{57}$ and L is $CR^{55}$;

$R^{55}$, $R^{56}$ and $R^{57}$ are each independently hydrogen, hydrocarbyl or substituted hydrocarbyl, or any two of $R^{55}$, $R^{56}$ and $R^{57}$ taken together form a ring;

$R^{78}$ is hydrocarbyl or substituted hydrocarbyl;

$R^{79}$, $R^{80}$, $R^{81}$, $R^{82}$, $R^{83}$, $R^{84}$, $R^{85}$, $R^{86}$, $R^{87}$, $R^{88}$ and $R^{89}$ are each independently hydrogen, hydrocarbyl, substituted hydrocarbyl, or a functional group;

$R^{90}$, $R^{91}$, $R^{92}$ and $R^{93}$ are each independently hydrocarbyl or substituted hydrocarbyl;

$R^{94}$ and $R^{95}$ are each independently hydrocarbyl or substituted hydrocarbyl;

$R^{96}$, $R^{97}$, $R^{98}$, and $R^{99}$ are each independently hydrogen, hydrocarbyl, substituted hydrocarbyl or a functional group;

both of T are S (sulfur) or NH (amino);

each E is N (nitrogen) or $CR^{108}$ wherein $R^{108}$ is hydrogen, hydrocarbyl, substituted hydrocarbyl or a functional group;

$R^{100}$, $R^{101}$, $R^{102}$, $R^{103}$, $R^{104}$, $R^{105}$, $R^{106}$, and $R^{107}$ are each independently hydrogen, hydrocarbyl, substituted hydrocarbyl, or a functional group;

$R^{109}$, $R^{110}$, $R^{111}$, $R^{112}$, $R^{113}$, $R^{114}$, $R^{115}$ and $R^{116}$ are each independently hydrogen, hydrocarbyl, substituted hydrocarbyl or a functional group; and $R^{28}$ and $R^{29}$ are each independently hydrogen, hydrocarbyl or substituted hydrocarbyl.

Also disclosed herein is a compound of the formula (XXXIII)

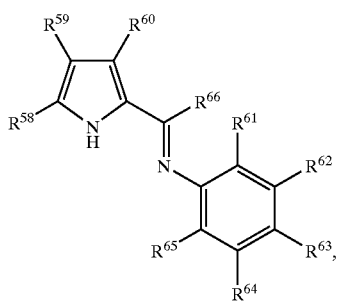

wherein:

$R^{58}$, $R^{59}$, $R^{60}$, $R^{62}$, $R^{63}$ and $R^{64}$ are each independently hydrogen, hydrocarbyl, substituted hydrocarbyl, or a functional group, and provided that any two of these groups vicinal to one another taken together may form a ring, or if vicinal to $R^{61}$ or $R^{65}$ form a ring with them;

$R^{66}$ is hydrogen, hydrocarbyl or substituted hydrocarbyl; and $R^{61}$ and $R^{65}$ are each independently hydrocarbyl containing 2 or more carbon atoms, or substituted hydrocarbyl containing 2 or more carbon atoms, and provided that $R^{61}$ and $R^{65}$ may form a ring with any group vicinal to it.

This invention also concerns a compound of the formula (XXXVI)

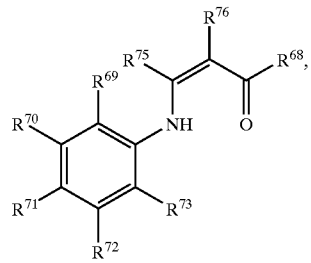

wherein:

$R^{68}$ is hydrocarbyl, substituted hydrocarbyl, —$SR^{117}$, —$OR^{117}$, or —$NR^{118}{}_2$, $R^{76}$ is hydrogen, a functional group, hydrocarbyl or substituted hydrocarbyl, and $R^{75}$ is hydrocarbyl or substituted hydrocarbyl, and provided that $R^{68}$ and $R^{76}$ or $R^{75}$ and $R^{76}$ taken together may form a ring;

$R^{117}$ is hydrocarbyl or substituted hydrocarbyl;

each $R^{118}$ is independently hydrogen, hydrocarbyl or substituted hydrocarbyl;

$R^{70}$, $R^{71}$ and $R^{72}$ are each independently hydrogen, hydrocarbyl, substituted hydrocarbyl or a functional group;

$R^{69}$ and $R^{73}$ are hydrocarbyl containing 3 or more carbon atoms, substituted hydrocarbyl containing 3 or more carbon atoms or a functional group;

and provided that any two of $R^{70}$, $R^{71}$, $R^{72}$, $R^{69}$ and $R^{73}$ vicinal to one another together may form a ring.

DETAILS OF THE INVENTION

Herein, certain terms are used. Some of them are:

A "hydrocarbyl group" is a univalent group containing only carbon and hydrogen. If not otherwise stated, it is preferred that hydrocarbyl groups herein preferably contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain preferably 1 to about 30 carbon atoms. Included in the meaning of "substituted" are heteroaromatic rings.

By "(inert) functional group" herein is meant a group other than hydrocarbyl or substituted hydrocarbyl which is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —$OR^{25}$, —$CO^2R^{25}$, —$NO_2$, a —$NR^{25}{}_2$, wherein $R^{25}$ is hydrocarbyl or substituted hydrocarbyl. In cases in which the functional group may be near a nickel atom the functional group should not coordinate to the metal atom more strongly than the groups in compounds which are shown as coordinating to the metal atom, that is they should not displace the desired coordinating group.

By a "polymerization process" herein (and the polymers made therein) is meant a process which produces a polymer with a degree of polymerization (DP) of about 5 or more, preferably about 10 or more, more preferably about 40 or more [except where otherwise noted, as in P in compound (XVII)]. By "DP" is meant the average number of repeat (monomer) units in the polymer.

By "aryl" herein is meant a monovalent radical whose free valence is to a carbon atom of an aromatic ring. Unless otherwise noted herein, preferred aryl groups contain carbocyclic rings, but heterocyclic rings are also included within the definition of "aryl". The aryl radical may contain one ring or may contain 2 or more fused rings, such as 9-anthracenyl or 1-naphthyl. Unless otherwise stated aryl groups preferably contain 5 to 30 carbon atoms.

By "substituted aryl" herein is meant an aryl radical substituted with one or more groups that do not interfere with the synthesis of the compound or the resulting polymerization. Suitable substituents include alkyl, aryl such as phenyl, halo, alkoxy, ester, dialkylamino and nitro. Unless otherwise stated, substituted aryl groups contain 5 to about 30 carbon atoms.

By a "monoanionic ligand" is meant a ligand with one negative charge.

By a "neutral ligand" is meant a ligand that is not charged.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By a styrene herein is meant a compound of the formula

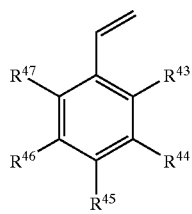

(XXXIV)

wherein $R^{43}$, $R^{44}$, $R^{45}$, $R^{46}$ and $R^{47}$ are each independently hydrogen, hydrocarbyl, substituted hydrocarbyl or a functional group, all of which are inert in the polymerization process. It is preferred that all of $R^{43}$, $R^{44}$, $R^{45}$, $R^{46}$ and $R^{47}$ are hydrogen. Styrene (itself) is a preferred styrene.

By a norbornene is meant ethylidene norbornene, dicyclopentadiene, or a compound of the formula

(XXXV)

wherein $R^{40}$ is hydrogen or hydrocarbyl containing 1 to 20 carbon atoms. It is preferred that $R^{40}$ is hydrogen or alkyl, more preferably hydrogen or n-alkyl, and especially preferably hydrogen. The norbornene may be substituted by one or more hydrocarbyl, substituted hydrocarbyl or functional groups in the $R^{40}$ or other positions, with the exception of the vinylic hydrogens, which remain. Norbornene (itself), dimethyl endo-norbornene-2,3-dicarboxylate, t-butyl 5-norbornene-2-carobxylate are preferred norbornenes and norbornene (itself) is especially preferred.

By a π-allyl group is meant a monoanionic ligand with 3 adjacent sp² carbon atoms bound to a metal center in an η³ fashion. The three sp2 carbon atoms may be substituted with other hydrocarbyl groups or functional groups. Typical π-allyl groups include

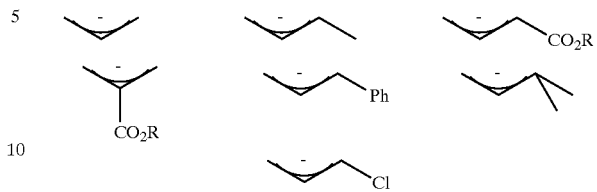

wherein R is hydrocarbyl. By a π-benzyl group is meant π-allyl ligand in which two of the sp² carbon atoms are part of an aromatic ring. Typical π-benzyl groups include

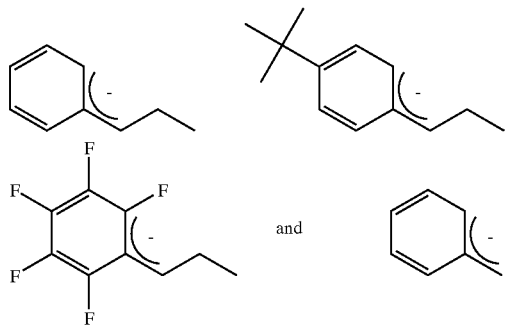

and

π-Benzyl compounds usually initiate polymerization of the olefins fairly readily even at room temperature, but π-allyl compounds may not necessarily do so. Initiation of 7E-allyl compounds can be improved by using one or more of the following methods:

Using a higher temperature such as about 80° C.

Decreasing the bulk of the monoanionic ligand, such as aryl being 2,6-dimethylphenyl instead of 2,6-diisopropylphenyl.

Making the π-allyl ligand more bulky, such as using

rather than the simple π-allyl group itself.

Having a Lewis acid or a material that acts as a Lewis acid present while using a π-allyl or π-benzyl group, especially a functional π-allyl or π-benzyl group. Relatively weak Lewis acids such as triphenylborane, tris(pentafluorophenyl)borane, tris(3,5-trifluoromethylphenyl)borane, and poly(methylaluminoxane) are preferred. Suitable functional groups include chloro and ester.

Lewis acids may also be optionally present when compounds containing $L^1$ and/or $L^2$ are present in the polymerization, even when $L^2$ is not a π-allyl or π-benzyl group. It is believed that the Lewis acid, if present, may help to remove $L^1$ (if present) from the nickel atom, thereby facilitating the coordination of the olefin to the Ni atom. If a compound containing $L^1$ and/or $L^2$ does not act as a polymerization catalyst, it is suggested that a Lewis acid, such as those mentioned above be added to the process to determine if polymerization will then take place. Such testing requires minimal experimentation, and is illustrated in the Examples. Not surprisingly, with any particular set of polymerization process ingredients, some Lewis acids may be more effective than others.

In preferred olefins herein, $R^{67}$ is hydrogen or α-alkyl containing 1 to 20 carbon atoms (an α-olefin), more preferably n-alkyl containing 1 to 8 carbon atoms, or more preferably hydrogen (e.g., ethylene) or methyl (e.g., propylene), and especially preferably hydrogen. A combination of ethylene and $H_2C$=$CHR^{67}$ wherein $R^{67}$ n-alkyl containing 1 to 8 carbon atoms is also preferred, and a combination of ethylene and propylene is more preferred. It is also preferred that s is 2 or more, and/or $R^{77}$ is alkyl, especially preferably methyl or ethyl. When $H_2C$=$CH(CH_2)_sCO_2R^{77}$ is present as one of the olefins, it is preferred that $R^{67}$ is hydrogen.

While not all homopolymers and copolymers of the olefinic monomers useful herein can be made using the polymerization processes described herein, most homopolymers and many copolymers can be made. The following homopolymers can be readily made in these polymerization processes: polyethylene, polystyrene, a polynorbornene, poly-α-olefins (often lower molecular weight polymers obtained), polycyclopentene (often lower molecular weight polymers obtained). Attempted homopolymerization of functionalized norbornenes often does not proceed, nor do homopolymerizations of compounds of the formula $H_2C$=$CH(CH_2)_sCO_2R^{77}$. Many copolymers can be made, including ethylene/α-olefins, styrene/norbornene copolymers, copolymers of 2 or more norbornenes including functionalized norbornenes, copolymers of ethylene and cyclopentene, copolymers of ethylene and a norbornene, and copolymers of ethylene and $H_2C$=$CH(CH_2)_sCO_2R^{77}$.

Not every variation of every nickel complex listed in the various polymerizations will make every one of the polymers listed immediately above. However, many of them will make most if not all of these types of polymers. While no hard and fast rules can be given, it is believed that for polymerizations which include ethylene and/or α-olefins, steric hindrance about the nickel atom caused by substituent groups is desirable for making polymers, especially higher molecular weight polymers, while for polymers containing one or more of a styrene and/or a norbornene such steric hindrance is not as important.

The Ni[II] complexes that are useful herein for the polymerization of ethylene contain a bidentate monoanionic ligand (other than a combined $L^1$ and $L^2$ ) in which the coordinating atoms are 2 nitrogen atoms, a nitrogen atom and an oxygen atom, a phosphorous atom and a sulfur atom, or an oxygen atom and a sulfur atom. Compounds of formulas (I) through (VI), (XVIII), (XXVII), and (XXXVII)–(XXXX) can be made by reaction of 2 moles of the anionic form of the ligand with one mole of the appropriate nickel allyl or benzyl precursor (XXI),

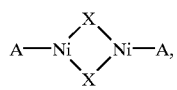
(XXI)

wherein X is preferably chlorine or bromine and A is a π-allyl or π-benzyl group, to form the nickel compound (see Examples 17–40 and 469–498).

Compounds of formulas (VII) through (XII), (XIX), (XXVIII), and (XXXXI)–(XXXXIV) can be synthesized by protonation of a suitable Ni[0] or Ni[II] precursor by the neutral ligand or by reaction of a suitable Ni[II] precursor with the anionic form of the ligand. Examples of suitable Ni[0] and Ni[II] precursors include $Ni(1,4\text{-cyclooctadiene})_2$, $(N,N,N'N'\text{-tetramethylethylenediamine})NiMe_2$, 2,2'-bipyridineNiMe$_2$, $(MePPh_2)_3NiMe_2$, $[Ni(OMe)Me(PPh_3)]_2$, $[Ni(OMe)Me(PMe_3)]_2$, $NiBr_2$, N,N,N'N'-tetramethylethylenediamine)Ni (acetylacetonate)$_2$, (1,2-dimethoxyethane) $NiBr_2$, N,N,N'N'-tetramethylethylenediamine)Ni $(CH_2$=$CHCO_2CH_3)_2$, (pyridine)$_2Ni(CH_2$=$CHCO_2CH_3)_2$, and (acetylacetonate)Ni(Et)(PPh$_3$). The addition of phosphine or ligand "sponges" such as CuCl, BPh$_3$ or tris (pentafluorophenyl)borane may aid such reactions.

Some of the nickel compounds herein such as (XXXIX), (XXXX), (XXXXIII) and (XXXXIV) may exist as "dimers" or monomers, or in equilibrium between the two. The dimer contains two nickel atoms, each nickel atom being coordinated to $L^1$ and $L^2$, wherein $L^1$ and $L^2$ combined may be a bidentate monoanionic ligand such as a π-allyl or π-benzyl group, and both Ni atoms "share" coordination to each of the other ligands present. As described herein, depiction of the monomeric compound also includes the dimeric compound, and vice versa. Whether any particular nickel compound is (predominantly) a monomer or dimer, or both states are detectable will depend on the ligands present. For instance it is believed that as the ligands become more bulky, especially about the nickel atom, the tendency is to form a monomeric compound.

Ligands for compounds (I) and (VII) of the formula

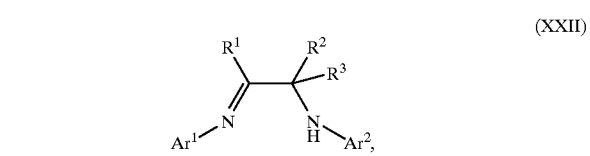
(XXII)

can be made by reaction of an alpha-diimine of the formula $Ar^1N$=$CR^1$—$CR^2$=$NAr^2$ with one equivalent of a compound of the formula $R^3$ Li, see for instance M. G. Gardner, et al., Inorg. Chem., vol. 34 p. 4206–4212 (1995). In another case, a ligand of the formula

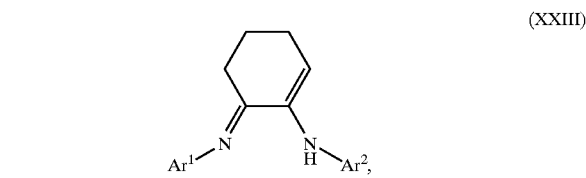
(XXIII)

can be made by the condensation of 1,2-cyclohexadione with the corresponding aromatic amine(s), see for instance R. van Asselt, et. al, Recl. Trav. Chim. Pays-Bas, vol. 113, p. 88–98 (1994). Note that in (XXIII) $R^1$, $R^2$ and $R^3$ taken together form a ring, with $R^2$ and $R^3$ both "part of" a double bond to the same carbon atom. These ligands can then be converted to their corresponding nickel complexes by the methods described above.

Compounds of the formula (II) can be made by the reaction of a ligand of the formula

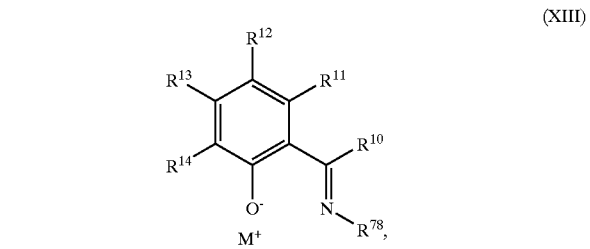
(XIII)

while compounds of the formula (VIII) can be made from the protonated form of (XIII). (XIII) can be made from the corresponding salicylaldehyde (when $R^{10}$ is hydrogen) and aromatic amine, followed by reaction with an alkali metal base (such as an alkali metal hydride) to form the aryloxide.

(III) and (IX) can be made by reacting pyrrole-2-carboxyaldehyde with the appropriate aromatic amine to form the pyrrole-2-imine, followed by reaction with a strong base to form the pyrrole anion, and then reaction with the nickel precursors described above to form the nickel[II] complex.

Similarly, (IV) and (X) can be formed from an alkali metal thiophene-2-carboxylate and the nickel precursors described above.

When K is $CR^{27}$ the ligand for (V) and (XI) can be made by the reaction of the corresponding ketone (which may contain other functional groups) with an aromatic amine to give

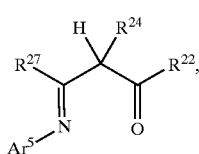

(XXIV)

which is a tautomer of

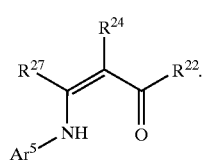

(XXV)

Useful ketones for making (V) and (XI) include ethyl acetoacetate, ethyl 2-ethylacetoacetate, isobutyl acetoacetate, t-butyl acetoacetate, S-t-butyl acetoacetate, allyl acetoacetate, ethyl 2-methylacetoacetate, methyl 2-chloroacetoacetate, ethyl 2-chloroacetoacetate, methyl 4-chloroacetoacetate, ethyl 4-chloroacetoacetate, ethyl 4,4,4-trifluoroacetoacetate, S-methyl 4,4,4-trifluoro-3-oxothiobutyrate, 2-methoxyethyl acetoacetate, methyl 4-methoxyacetoacetate, methyl propionylacetate, ethyl propionyl acetate, ethyl isobutyrylacetate, methyl 4,4-dimethyl-3-oxopentanoate, ethyl bytyrylacetate, ethyl 2,4-dioxovalerate, methyl 3-oxo-6-octenoate, dimethyl 1,3-acetonedicarboxylate, diethyl 1,3-acetonedicarboxylate, di-t-butyl 1,3-acetonedicarboxylate, dimethyl 3-oxoadipate, diethyl 3-oxopimelate, dimethyl acetylsuccinate, diethyl acetylsuccinate, diethyl 2-acetylglutarate, methyl 2-cyclopentatecarboxylate, ethyl 2-cyclopentanecarboxylate, ethyl 4-methyl-2-cyclohexanone-1-carboxylate, ethyl 4-methyl-2-cyclohexanone-1-carboxylate, ethyl 3-(1-adamantyl)-3-oxopropionate, methyl 2-oxo-1-cycloheptanecarboxylate, N-t-butylacetoamide, 2-chloro-N,N-dimethylacetoacetamide, 4,4,4-trifluoro-1-phenyl-1,3-butanedione, 4,4,4-trifluoro-1-(2-naphthyl)-1,3-butanedione, 2-acetyl-1-tetralone, ethyl 2-benzylacetoacetonate, methyl 1-benzyl-4-oxo-3-piperidinecarboxylate hydrochloride, benzyl acetoacetate, aceto-acetanilide, o-acetoacetotoluide, N-(2,4-dimethylphenyl)-3-oxobutyramide, o-acetoacetanisidide, 41-chloroacetoacetanilide, and 1,1,1-trifluoro-3-thianoylacetone.

When K is N in (V) and (XI), and $R^{24}$ is nitrile, the ligand can made by the reaction of $R^{22}C(O)CH_2CN$ with the diazonium salt of the corresponding arylamine, see for instance V. P. Kurbatov, et al., Russian Journal of Inorganic Chemistry, vol. 42, p. 898–902(1997). This paper also reviews methods of making ligands wherein K is $CR^{27}$.

The boron containing ligands needed for compounds (VI) and (XII),

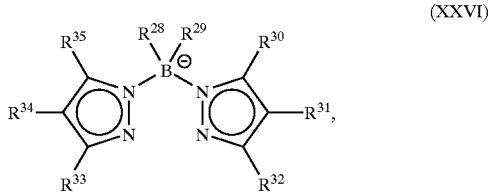

(XXVI)

can be made by known procedures, see for instance S. Trofimenko, Prog. Inorg. Chem., vol. 34, p. 115–210 (1986) and S. Trofimenko, Chem. Rev., vol. 93, p. 943–980 (1993).

The synthesis of the tropolone-type ligands required for (XVIII) and (XIX) are described in J. J. Drysdale, et al., J. Am. Chem. Soc., vol. 80, p. 3672–3675 (1958); W. R. Brasen, et al., vol. 83, p. 3125–3138 (1961); and G. M. Villacorta, et al., J. Am. Chem. Soc., vol. 110, p. 3175–3182 (1988). These can be reacted as described above to form the corresponding nickel complex.

The ligand for (XXVII) and (XXVIII),

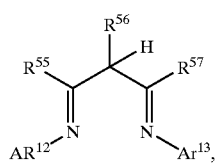

(XXIX)

or either of its tautomers,

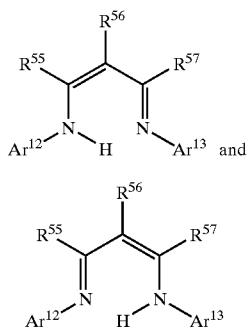

(XXX)

(XXXI)

can be made by reaction of the appropriate α,χ-dioxo compound such as a 1,3-dione or 1,3-dial or similar compound with the appropriate aromatic amine, see for instance J. E. Parks, et al., Inorg. Chem., vol. 7, p. 1408 (1968); R. H. Holm, Prog. Inorg. Chem., vol. 14, p. 241 (1971); and P. C. Healy, et al., Aust. J. Chem., vol. 32, p. 727 (1979).

If the ligand precursor may form a tautomer, the ligand itself may usually be considered a tautomer. For instance, the monoanionic ligand derived from (XXIX) and it tautomers may be written as

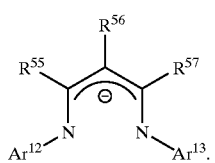

(XXXII)

In (XXVII) and (XXVIII) when L and/or G is N, the ligand can be made by the method described in Y. A. Ibrahim, et al., Tetrahedron, vol. 50, p. 11489–11498(1994) and references described therein.

The ligands for (XXXVII) and (XXXXI) can be made by methods described in Phosphorous, Sulfur and Silicon, vol. 47, p. 401 et seq. (1990), and analogous reactions.

The ligands for (XXXVIII) and (XXXXII) can be made by reacting $R_2PLi$ (from $R_2PH$ and n-BuLi) with propylene sulfide to form $R_2CH_2CH(CH_3)SLi$, and analogous reactions.

The ligands for (XXXIX) and (XXXXIII), and for (XXXX) and (XXXXIV) are commercially available. Those used herein were bought from Aldrich Chemical Co., Inc., Milwaukee, Wis., U.S.A.

In the compounds (and ligands in those compounds) (I) through (XII), (XVIII), (XIX), (XXVII), (XXVIII), and (XXXVII)–(XXXXIV), certain groups are preferred. When present, they are:

$R^1$ and $R^2$ are both hydrogen; and/or
$R^3$ is alkyl or aryl containing 1 to 20 carbon atoms, more preferably $R^3$ is t-butyl; and/or
$R^1$, $R^2$ and $R^3$ taken together are

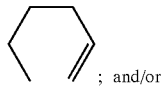 ; and/or $Ar^1$, $Ar^2$, $Ar^3$, $Ar^4$, $Ar^5$, $Ar^{10}$ and $Ar^{11}$ are each independently (XIV)

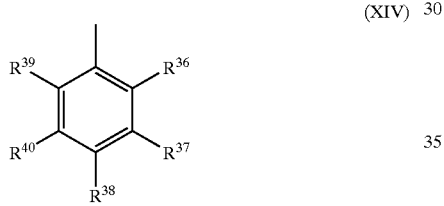

wherein $R^{36}$, $R^{37}$, $R^{38}$, $R^{39}$ and $R^{40}$ are each independently hydrogen, hydrocarbyl, substituted hydrocarbyl or a functional group, provided that any 2 of $R^{37}$, $R^{37}$, $R^{38}$, $R^{39}$ and $R^{40}$ that are vicinal to one another taken together may form a ring (for example the group 9-anthracenyl), and it is especially preferred that $R^{36}$ and $R^{39}$ are halo, phenyl or alkyl containing 1 to 6 carbon atoms, and it is more preferred that $R^{36}$ and $R^3$ are methyl, bromo, chloro, t-butyl, hydrogen, or isopropyl; and/or
$R^{78}$ is $Ar^3$, which is aryl or substituted aryl;
$Ar^1$, $Ar^2$, $Ar^3$, $Ar^4$, $Ar^5$, $Ar^{10}$ and $Ar^{11}$ are each independently 2-pyridyl or substituted 2-pyridyl;
if a π-allyl group is (XX)

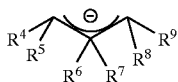

then $R_4$, $R_5$, $R_6$, and $R_8$ are hydrogen; and/or
$R^4$, $R^5$, $R^6$, $R_7$, $R^8$ and $R^9$ are hydrogen; and/or
$R^4$, $R^5$, $R^6$, and $R^7$ are hydrogen and $R^8$ and $R^9$ are methyl;
one of $R^7$ or $R^9$ is —$CO_2R^{41}$ or chloro, and the other is hydrogen, and wherein $R^{41}$ is hydrocarbyl, preferably alkyl containing 1 to 6 carbon atoms; and/or
$R^{11}$, $R^{12}$, $R^{13}$ and $R^{14}$ are each independently chloro, bromo, iodo, alkyl, alkoxy, hydrogen or nitro; and/or
$R^{11}$ and $R^{12}$ taken together form an aromatic carbocyclic 6-membered ring; and/or $R^{14}$ and $R^{12}$ are both chloro, bromo, iodo, t-butyl or nitro; and/or
$R^{11}$ and $R^{13}$ are methoxy;
$R^{14}$ is hydrogen and $R^{12}$ is nitro; and/or
one or more of $R^{11}$, $R^{12}$, $R^{13}$ and $R^{14}$ are hydrogen; and/or
$R^{16}$, $R^{17}$, $R^{18}$, $R^{19}$, $R^{20}$, and $R^{21}$ are hydrogen; and/or
$R^{16}$, $R^{17}$, $R^{18}$, $R^{19}$, and $R^{20}$ are hydrogen and $R^{21}$ is methyl; and/or
K is $CR^{27}$; and/or
$R^{27}$ is hydrogen, hydrocarbyl, substituted hydrocarbyl, or a functional group; and/or
$R^{27}$ is alkyl, more preferably methyl; and/or
$R^{24}$ is hydrogen, alkyl, cyano, or halo, more preferably hydrogen; and/or
$R^{22}$ is hydrocarbyl or —$OR^{117}$, wherein $R^{117}$ is hydrocarbyl, more preferably alkyl containing 1 to 6 carbon atoms, or $R^{22}$ is phenyl; and/or
$R^{32}$ and $R^{33}$ are both alkyl containing 1 to 6 carbon atoms or phenyl, more preferably isopropyl; and/or
$R^{28}$ and $R^{29}$ are both hydrogen or phenyl; and/or
$R^{30}$, $R^{31}$, $R^{34}$ and $R^{35}$ are all hydrogen; and/or
$R^{31}$ and $R^{32}$ taken together and $R^{33}$ and $R^{34}$ taken together are both a 6-membered aromatic carbocyclic ring having a t-butyl group vicinal to the $R^{32}$ and $R^{33}$ positions; and/or
$R^{50}$, $R^{51}$, $R^{52}$, $R^{53}$ and $R^{54}$ are hydrogen; and/or
L is $CR^{55}$ wherein $R^{55}$ is hydrocarbyl, hydrogen, or substituted hydrocarbyl; and/or
G is $CR^{57}$ wherein $R^{57}$ is hydrocarbyl, hydrogen or substituted hydrocarbyl; and/or
more preferably $R^{55}$ and $R^{57}$ are both alkyl or fluorinated alkyl, more preferably methyl; and/or
$R^{56}$ is hydrogen; and/or
$Ar^{12}$ and $Ar_{13}$ are both 2,6-diisopropylphenyl; and/or
$R^{79}$, $R^{80}$, $R^{81}$, $R^{82}$, $R^{83}$, $R^{84}$, $R^{85}$, $R^{86}$, $R^{87}$, $R^{88}$ and $R^{89}$ are each independently hydrogen or alkyl; and/or
$R_{90}$, $R_{91}$, $R_{92}$ and $R_{93}$ are each independently hydrocarbyl, more preferably aryl, and especially referably phenyl; and/or
$R^{94}$ and $R^{95}$ are each independently hydrocarbyl; and/or
$R^{96}$, $R^{97}$, $R^{98}$, and $R^{99}$ are each independently hydrogen or hydrocarbyl; and/or
E is N or $CR^{108}$; and/or
$R^{108}$ is hydrogen or hydrocarbyl; and/or
$R^{100}$, $R^{101}$, $R^{102}$, $R^{103}$, $R^{104}$, $R^{105}$, $R^{106}$, and $R^{107}$ is each independently hydrogen, hydrocarbyl, or halo; and/or
$R^{109}$, $R^{110}$, $R^{111}$, $R^{112}$, $R^{113}$, $R^{114}$, $R^{115}$, and $R^{116}$ are each independently hydrogen or hydrocarbyl.

Specific preferred compounds (I)–(IV) and (VI) are given in Table A. The same groupings shown in the Table are preferred for the analogous compounds (VII)–(X) and (XII). In all of these compounds, where applicable, $R^4$, $R^5$, $R^6$, $R^8$, $R^9$ [in (XX) above], $R^{15}$, $R^{16}$, $R^{17}$, $R^{18}$, $R^{19}$, $R^{20}$, $R^{30}$, and $R^{35}$ are all hydrogen (with the exceptions in the footnotes), $R^{10}$ is hydrogen or methyl, $R^{21}$ is hydrogen or methyl, and $R^7$ is —$CO_2CH_3$ (with the exceptions in the footnotes). In compounds wherein $L_1$ and $L_2$ appear, and especially in compounds of formula (VIII) it is preferred that $L_2$ is a nitrile, such as benzonitrile, p-methylbenzonitrile methyl nitrile, or pyridine or a substituted pyridine such as 2,6-dimethyl pyridine. A preferred $L_2$ is an alkyl group, especially methyl. $L_1$ and $L_2$ taken together may be a π-allyl or π-benzyl group, but for all compounds in which $L_1$ and $L_2$ are present (i.e. combined) it is preferred that they are not a π-allyl or π-benzyl group.

Table B give specific preferred compounds for (V), (XXXVII) and (XXXIX) as well as the corresponding compounds (XI), (XXXXI) and (XXXXIII) respectively. In all of these compounds $Ar^5$ is 2,6-diisopropylphenyl, K is $CCH_3$, $R^{24}$, $R^{79}$, $R^{80}$, $R^{82}$, $R^{85}$, $R^{87}$, $R^{88}$, and $R^{89}$ are hydrogen, $R^{90}$, $R^{91}$, $R^{92}$, and $R^{93}$ are phenyl.

In a specific preferred compounds (XXVII) and the corresponding (XXVIII), $Ar^{12}$ and $Ar^{13}$ are 2,6-diisopropylphenyl, L and G are $CCH_3$, and $R^{56}$ is hydrogen.

In a specific preferred compound (XXXVIII) and the corresponding (XXXXVII), $R^{94}$ and $R^{95}$ are each cyclohexyl, $R^{96}$, $R^{97}$ and $R^{98}$ are hydrogen, and $R^{99}$ is methyl.

In a specific preferred compound (XXXX) and the corresponding (XXXXIV), $R^{110}$, $R^{111}$, $R^{114}$ and $R^{115}$ are hydrogen and $R^{109}$, $R^{112}$, $R^{113}$ and $R^{116}$ are methyl.

TABLE A

| Cmpd[c] | $R^1$ | $R^2$ | $R^3$ | $Ar^1$ and $Ar^2$ | $Ar^3$ | $R^{11}$ | $R^{12}$ | $R^{13}$ | $R^{14}$ | $Ar^4$ |
|---|---|---|---|---|---|---|---|---|---|---|
| Ia | [a] | [a] | [a] | 2,6-i-Pr—Ph | — | — | — | — | — | — |
| Ib | H | H | t-butyl | 2,6-i-Pr—Ph | — | — | — | — | — | — |
| IIa | — | — | — | — | 2,6-i-Pr—Ph | H | t-butyl | H | t-butyl | — |
| IIb | — | — | — | — | 2,6-i-Pr—Ph | [b] | [b] | H | H | — |
| IIc | — | — | — | — | 2,6-Me—Ph | [b] | [b] | H | H | — |
| IId | — | — | — | — | 2,6-Me—Ph | H | Cl | H | Cl | — |
| IIe | — | — | — | — | 2,6-i-Pr—Ph | H | Cl | H | Cl | — |
| IIf | — | — | — | — | 2,6-i-Pr—Ph | H | $NO_2$ | H | $NO_2$ | — |
| IIg | — | — | — | — | 2,4,6-t-butyl-Ph | H | $NO_2$ | H | $NO_2$ | — |
| IIh | — | — | — | — | 2,6-Br-4-Me—Ph | H | $NO_2$ | H | $NO_2$ | — |
| IIi | — | — | — | — | 2,6-Me—Ph | H | $NO_2$ | H | $NO_2$ | — |
| IIj | — | — | — | — | 2,6-i-Pr—Ph | H | $NO_2$ | H | H | — |
| IIk | — | — | — | — | 2-t-Bu—Ph | H | $NO_2$ | H | $NO_2$ | — |
| IIl | — | — | — | — | 2,6-Me—Ph | H | t-butyl | H | t-butyl | — |
| IIm | — | — | — | — | 2,6-Br-4-F—Ph | H | t-butyl | H | t-butyl | — |
| IIn | — | — | — | — | 2-Cl-6-Me—Ph | H | $NO_2$ | H | $NO_2$ | — |
| IIo | — | — | — | — | [f] | H | $NO_2$ | H | $NO_2$ | — |
| IIp | — | — | — | — | 2,6-i-Pr—Ph | H | I | H | I | — |
| IIq | — | — | — | — | 2,6-i-Pr—Ph | OMe | H | OMe | H | — |
| IIr | — | — | — | — | 2,6-Br-4-F—Ph | [b] | [b] | H | H | — |
| IIs | — | — | — | — | 3-Me-1-pyridyl | [b] | [b] | H | H | — |
| IIt | — | — | — | — | 2-t-Bu—Ph | [b] | [b] | H | H | — |
| IIu | — | — | — | — | [e] | H | H | H | H | — |
| IIIa | — | — | — | — | — | — | — | — | — | 2,6-i-Pr—Ph |
| VIa | — | — | — | — | — | — | — | — | — | — |
| VIb | — | — | — | — | — | — | — | — | — | — |

| Cmpd[c] | $R^{28}$ | $R^{29}$ | $R^{30}$ | $R^{31}$ | $R^{32}$ | $R^{33}$ | $R^{34}$ | $R^{35}$ |
|---|---|---|---|---|---|---|---|---|
| Ia | — | — | — | — | — | — | — | — |
| Ib | — | — | — | — | — | — | — | — |
| IIa | — | — | — | — | — | — | — | — |
| IIb | — | — | — | — | — | — | — | — |
| IIc | — | — | — | — | — | — | — | — |
| IId | — | — | — | — | — | — | — | — |
| IIe | — | — | — | — | — | — | — | — |
| IIf | — | — | — | — | — | — | — | — |
| IIg | — | — | — | — | — | — | — | — |
| IIh | — | — | — | — | — | — | — | — |
| IIi | — | — | — | — | — | — | — | — |
| IIj | | | | | | | | |
| IIk | | | | | | | | |
| IIl | | | | | | | | |
| IIm | | | | | | | | |
| IIn | | | | | | | | |
| IIo | | | | | | | | |
| IIp | | | | | | | | |
| IIq | | | | | | | | |
| IIr | | | | | | | | |
| IIs | | | | | | | | |
| IIt | | | | | | | | |
| IIu | | | | | | | | |
| IIIa | — | — | — | — | — | — | — | — |
| VIa | H | H | H | [d] | [d] | [d] | [d] | H |
| VIb | Ph | Ph | H | H | i-propyl | i-propyl | H | H |

[a]$R^1$, $R^2$ and $R^3$ taken together are =CH—$CH_2$—$CH_2$—$CH_2$— wherein a vinylic carbon is vicinal to the amino nitrogen atom.
[b]$R^{11}$ and $R^{12}$ taken together form a 6 membered aromatic ring (the two fused rings together form a naphthalene group).
[c]$R^7$ in (XX) is —$CO_2CH_3$. All other groups in (XX) are H.
[d]$R^{31}$ and $R^{32}$, and $R^{33}$ and $R^{34}$, each pair taken together form a 6-membered aromatic carbocyclic ring substituted with a t-butyl group at the carbon atoms vicinal to the $R^{32}$ and $R^{33}$ positions.
[e]$R^{10}$ and $R^{78}$ taken together are, respectively, —$OCH_2C(CH_3)_2$— wherein the oxygen atom is attached to a carbon atom.
[f]1,2,3,4-tetrahydro-1-naphthyl

TABLE B

| Cmpd | R22 | R81 | R83 | R84 | R86 | T | E | R100 | R101 | R102 | R103 | R104 | R105 | R106 | R107 |
|---|---|---|---|---|---|---|---|---|---|---|---|---|---|---|---|
| Va | OMe | — | — | — | — | — | — | — | — | — | — | — | — | — | — |
| Vb | Me | — | — | — | — | — | — | — | — | — | — | — | — | — | — |
| XXXVIIa | — | Me | H | H | Me | — | — | — | — | — | — | — | — | — | — |
| XXXVIIb | — | H | Me | Me | H | — | — | — | — | — | — | — | — | — | — |
| XXXIXa | — | — | — | — | — | S | N | Cl | Cl | Cl | Cl | Cl | Cl | Cl | Cl |
| XXXIXb | — | — | — | — | — | NH | CCH₃ | Br | H | H | Br | Br | H | H | Br |

For clarity, the structures of compounds (Ia), (IIb) and (VIa) are shown below;

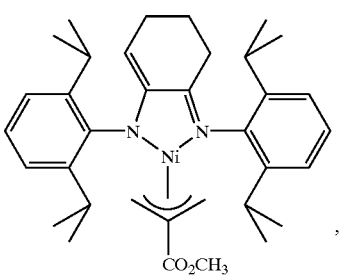
(Ia)

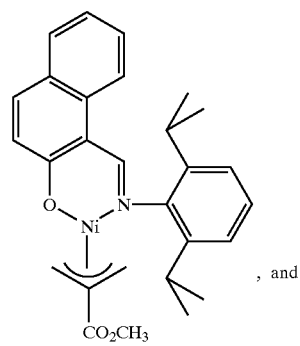
, and
(IIb)

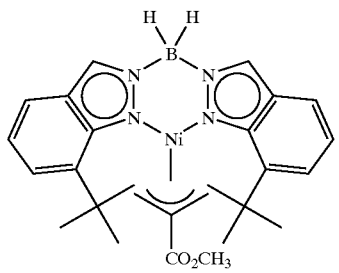
(VIa)

In (XXXIII) it is preferred that:
R⁵⁸, R⁵⁹, R⁶⁰, R⁶², R⁶³ and R⁶⁴ are each independently hydrogen, hydrocarbyl, substituted hydrocarbyl, or a functional group, and provided that any two of these groups vicinal to one another taken together may form a ring;
R⁶⁶ is hydrogen, hydrocarbyl or substituted hydrocarbyl; and
R⁶¹ and R⁶⁵ are each independently hydrocarbyl containing 2 or more carbon atoms, or substituted hydrocarbyl containing 2 or more carbon atoms.

$R^{58}$, $R^{59}$, $R^{60}$, $R^{62}$, $R^{63}$ and $R^{64}$ are each hydrogen; and/or
$R^{66}$ is hydrogen; and/or
$R^{61}$ and $R^{65}$ are each independently alkyl, and more preferred that both are isopropyl or methyl.
In a preferred compound or ligand (XVIII) and (XIX):
$R^{50}$, $R^{51}$, $R^{52}$, $R^{53}$ and $R^{54}$ are hydrogen; and/or
$Ar^{10}$ and $Ar^{11}$ are 2,6-dialkyl substituted phenyl, more preferably 2,6-dimethylphenyl or 2,6-diisopropylphenyl.

Monoanionic ligands which the olefins herein may add to include hydride, alkyl, substituted alkyl, aryl, substituted aryl, or $R^{26}C(=O)$— wherein $R^{26}$ is hydrocarbyl or substituted hydrocarbyl, and groups π-allyl and π-benzyl groups such as $\eta^3$-$C_8H_{13}$, see for instance J. P. Collman, et al., *Principles and Applications of Organotransition Metal Chemistry*, University Science Book, Mill Valley, Calif., 1987. Such groups are also described in World Patent Application WO 96/23010.

In compound (XXXVI) it is preferred that $R^{68}$ is —$OR^{117}$ or aryl, and/or $R^{75}$ is hydrocarbyl or substituted hydrocarbyl, and/or $R^{76}$ is hydrogen, hydrocarbyl, substituted hydrocarbyl or a functional group, more preferably hydrogen, hydrocarbyl or substituted hydrocarbyl.

In the second polymerization process described herein a nickel[II] complex such as any one of (VII)–(XII), (XIX), (XXVIII) or (XXXXI)–(XXXXIV) is either added to the polymerization process or formed in situ in the process. In fact, more than one such complex may be formed during the course of the process, for instance formation of an initial complex and then reaction of that complex to form a living ended polymer containing such a complex.

An example of such a complex which may be formed initially in situ is

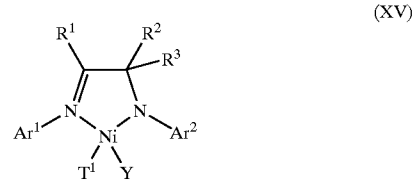
(XV)

wherein $R^1$ through $R^3$, $Ar^1$ and $Ar^2$ are as defined above, $T^1$ is hydride, alkyl, or $R^{42}C(=O)$— wherein $R^{42}$ is hydrocarbyl or substituted hydrocarbyl or any other monoanionic ligand which ethylene may add to, and Y is a neutral ligand, or $T^1$ and Y taken together are a bidentate monoanionic ligand which ethylene may add to. Similar complexes may also be formed with the ligands in (VIII)–(XII), (XIX), (XXVIII) and (XXXXI)–(XXXXIV). Such complexes may be added directly to the process or formed in situ.

After the olefin polymerization has started, the complex may be in forms such as

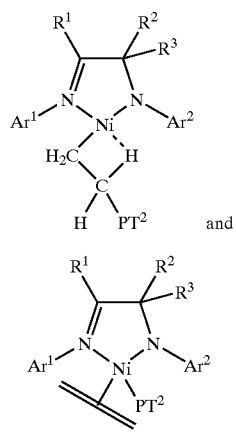

(XVI)

and (XVII)

wherein $R^1$ through $R^3{}_1$, $Ar^1$ and $Ar^2$ are as defined above, P is a divalent (poly)olefin group [the specific olefin shown in (XVI) and (XVII) is ethylene], —(CH2)$_x$— wherein x is an integer of 2 or more, and $T^1$ is an end group, for example the groups listed for $T^1$ above. (XVI) is a so-called agostic form complex. Similar complexes may also be formed with the ligands in (VIII)–(XII), (XI), (XXVIII) and (XXXXI)–(XXXXIV). Analogous compounds with other olefins in place of ethylene also may be formed. In all the polymerization processes herein, the temperature at which the olefin polymerization is carried out is about −100° C. to about +200° C., preferably about 0° C. to about 150° C., more preferably about 25° C. to about 100° C. The olefin concentration at which the polymerization is carried out is not critical, atmospheric pressure to about 275 MPa being a suitable range for ethylene and propylene.

The polymerization processes herein may be run in the presence of various liquids, particularly aprotic organic liquids. The catalyst system, olefin, and polyolefin may be soluble or insoluble in these liquids, but obviously these liquids should not prevent the polymerization from occurring. Suitable liquids include alkanes, cycloalkanes, selected halogenated hydrocarbons, and aromatic hydrocarbons. Hydrocarbons are the preferred solvent. Specific useful solvents include hexane, toluene, benzene, chloroform, methylene chloride, 1,2,4-trichlorobenzene, p-xylene, and cyclohexane.

The catalysts herein may be "heterogenized" by coating or otherwise attaching them to solid supports, such as silica or alumina. Where an active catalyst species is formed by reaction with a compound such as an alkylaluminum compound, a support on which the alkylaluminum compound is first coated or otherwise attached is contacted with the nickel compound precursor to form a catalyst system in which the active nickel catalyst is "attached" to the solid support. These supported catalysts may be used in polymerizations in organic liquids, as described in the immediately preceding paragraph. They may also be used in so-called gas phase polymerizations in which the olefin(s) being polymerized are added to the polymerization as gases and no liquid supporting phase is present.

Included herein within the definitions of all the polymerization processes are mixtures of starting materials that lead to the formation in situ of the nickel compounds specified in all of the polymerization processes.

In the Examples all pressures are gauge pressures.

Quantitative 3C NMR data for the polymers was obtained using a 10 mm probe on typically 15–20% solutions of the polymer and 0.05M Cr(acetylacetonate)$_3$ in 1,2,4-trichlorobenzene are 120–140° C. For a full description of determination of branching by $^{13}$C and $^1$H NMR, and for a definition of branches, see World Patent Application 96/23010, which is hereby included by reference.

In the Examples, the following abbreviations are used:
Am—amyl
Bu—butyl
Cy—cyclohexyl
E—ethylene
Et—ethyl
GPC—gel permeation chromatography
Me—methyl
MI—melt index
Mn—number average molecular weight
Mw—weight average molecular weight
MW—molecular weight
N—norbornene
P—propylene
PE—polyethylene
PDI—polydispersity, Mw/Mn
PMAO—poly(methylaluminoxane)
Pr—propyl
RI—refractive index
rt—room temperature
S—styrene
TCB—1,3,5-trichlorobenzene
THF—tetrahydrofuran
Tm—melting point
tmeda—N,N,N',N'-tetramethylethylenediamine
TO—turnovers, moles of monomer polymerized per mole of catalyst (nickel compound) used

EXAMPLES 1–16

Ligand Syntheses

Ligand syntheses and deprotonations were carried out according to the general procedures given below unless stated otherwise. The general procedure for imine synthesis is based upon published procedures for the synthesis of N-aryl-substituted imines given in the following reference: Tom Dieck, H.; Svoboda, M.; Grieser, T. Z. Naturforsch 1981, 36b, 823–832. The synthesis of ArN=CH—CH(t-Bu)—N(Ar)(Li) [Ar=2,6-(i-Pr)$_2$C$_6$H$_3$] is based on the published synthesis of (t-Bu)N=CH—CH(t-Bu)—N(t-Bu)(Li): Gardiner, M. G.; Raston, C. L. Inorg. Chem. 1995, 34, 4206–4212. The synthesis of ArN=C(Me)—CH=C(Me)—NH(Ar) [Ar=2,6-(i-Pr)$_2$C$_6$H$_3$] was published in WO Pat. Appl. 96/23010, and it was deprotonated according to the general procedure given below. The bis(pyrazolyl)borate anions that were used to synthesize complexes 18 and 19 were provided by S. Trofimenko (DuPont) and were synthesized according to the procedures published in the following review: Trofimenko, S. Chem. Rev. 1993, 93, 943.

General Procedure for Imine Synthesis. In a fume hood, formic acid catalyst was added to a methanol solution of the aldehyde and the aniline (~1.1–1.2 equiv). The reaction mixture was stirred and the resulting precipitate was collected on a frit and washed with methanol. The product was then dissolved in Et$_2$O or CH$_2$Cl$_2$ and stirred over Na$_2$SO$_4$ overnight. The solution was filtered through a frit with Celite® and the solvent was removed in vacuo to yield the product.

General Procedure for the Synthesis of Sodium Salts. The protonated forms of the ligands were dissolved in anhydrous THF in the drybox. Solid NaH was slowly added to the solution, and then the reaction mixture was stirred overnight. The next day, the solution was filtered through a frit with dry Celite®. The solvent was removed and the resulting powder was dried in vacuo. With some exceptions (e.g., Example 1), the sodium salts were not soluble in pentane and were further purified by a pentane wash.

EXAMPLE 1

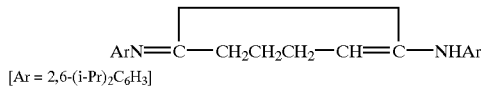
[Ar = 2,6-(i-Pr)$_2$C$_6$H$_3$]

A drop of formic acid was added to a solution of 1,2-cyclohexanedione (0.25 g, 2.2 mmol) and 2,6-diisopropylaniline (0.85 mL, 4.5 mmol) in 5 mL of methanol. The reaction mixture was stirred at rt for 3 days. The white solid thus formed was filtered, washed with a small amount of methanol and dried under vacuum. After recrystallization from hot methanol, the product (0.4 g; 41% yield; mp 81–83° C.) was isolated as white crystals: $^1$H NMR (CDCl$_3$, 300 MHz, rt): δ 7.28–7.08 (m, 6, H$_{aryl}$), 6.45 (s, 1, NH), 4.84 (t, 1, J=4.6, —CH=CNHAr), 3.30 (septet, 2, J=6.88, CHMe$_2$), 2.86 (septet, 2, J=6.87, C'HMe$_2$), 2.22 (m, 4, ArN=CCH$_2$CH$_2$—), 1.75 (m, 2, CH$_2$CH=CNHAr), 1.24 and 1.22 (d, 12 each, CHMe$_2$ and C'HMe$_2$); $^{13}$C NMR (CDCl$_3$, 300 MHz, rt) δ 162.1, 147.3, 145.8, 139.6, 137.0, and 136.4 (ArNH—C—C=NAr, Ar: C$_{ipso}$, C$_o$; Ar': C$_{ipso}$, C$_o$), 126.5, 123.4, 123.3 and 122.9 (Ar: C$_p$, C$_m$; Ar': C$_p$, C$_m$), 106.0 (ArNHC=CH—), 29.3, 28.4 and 28.3 (ArNHC=CH—CH$_2$CH$_2$CH$_2$C=NAr), 24.2 and 23.30 (CHMe$_2$, C'HMe$_2$), 23.25 and 22.9 (CHMe$_2$, C'HMe$_2$).

The sodium salt was cleanly synthesized according to the above general procedure: $^1$H NMR (300 MHz, THF-d$_8$): no THF coordinated.

EXAMPLE 2

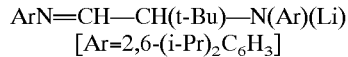

In a nitrogen-filled drybox, t-BuLi (7.81mL of a 1.7 M solution in pentane) was filtered through a short plug of dry Celite® into a round bottom flask. The flask was cooled to −35° C. in the drybox freezer. The diimine ArN=CH—CH=NAr [Ar=2,6-(i-Pr)$_2$C$_6$H$_3$] was added as a solid over a period of 15 min to the cold t-BuLi solution. The reaction mixture was stirred for ~2 h to give a viscous red solution. The solution was diluted with pentane and then filtered through a frit with Celite®. The resulting clear solution was concentrated under vacuum and then cooled in the drybox freezer to −35 ° C. An orange powder was obtained (3.03 g, 51.8%, 1st crop): $^1$H NMR (THF-d$_8$, 300 MHz, rt) δ 8.29 (s, 1, CH=N), 7.08 (d, 2, J=7.4, Ar: H$_m$), 7.00 (t, 1, J=7.0, Ar: H$_p$), 6.62 (m, 2, Ar: H$_m$), 6.14 (t, 1, J=7.4, Ar: H$_p$), 4.45 (s, 1, CH(t-Bu)), 3.08 (br septet, 2, CHMe$_2$), 3.05 (septet, 2, J=6.8, CHMe$_2$), 1.35 (d, 3, J=6.7, CHMe$_2$), 1.13 (d, 3, J=7.0, CHMe$_2$), 1.13 (br s, 12, CHMe$_2$), 1.02 (d, 3, J=6.7, CHMe$_2$), 0.93 (s, 9, CMe$_3$); $^{13}$C NMR (THF-d$_8$, 75 MHz, rt) δ 184.5 (N=CH), 161.9 and 150.1 (Ar, Ar': C$_{ipso}$), 139.7, 139.5 (br), 139.0 (br) and 137.3 (Ar, Ar': C$_o$), 125.0, 124.0, 123.5, 122.4 and 112.2 (Ar, Ar': C$_m$ and C$_p$), 80.8 (CH(t-Bu)), 41.5 (CMe$_3$), 29.3, 28.6, 27.8 (br), 26.5 (br), 26.3, 25.9, 25.6, 25.0 and 23.3 (br) (Ar, Ar': CHMe$_2$; CMe$_3$)

EXAMPLE 3

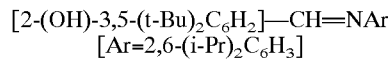

The general procedure for imine synthesis was followed using 10.1 g (43.0 mmol) of 3,5-di-t-butyl-2-hydroxybenzaldehyde and 9.91 g (55.9 mmol, 1.30 equiv) of 2,6-diisopropylaniline. A light yellow powder (10.5 g, 62.1%) was isolated: $^1$H NMR (CDCl$_3$, 300 MHz, rt) δ 13.50 (s, 1, OH), 8.35 (s, 1, CH=NAr), 7.56 (d, 1, J=2.7, H$_{aryl}$), 7.22 (m, 4, H$_{aryl}$), 3.08 (septet, 2, J=6.8, CHMe$_2$), 1.55 (s, 9, CMe$_3$), 1.39 (s, 9, C'Me$_3$), 1.23 (d, 12, J=6.7, CHMe$_2$).

The sodium salt was cleanly synthesized according to the above general procedure: H NMR (300 MHz, THF-d$_8$): 0.63 equiv of THF coordinated.

EXAMPLE 4

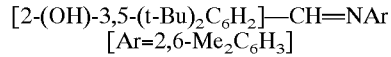

The general procedure for imine synthesis was followed using 3.05 g (13.0 mmol) of 3,5-di-t-butyl-2-hydroxybenzaldehyde and 1.89 g (15.6 mmol, 1.20 equiv) of 2,6-dimethylaniline. A yellow powder (2.00 g, 45.6%) was isolated: $^1$H NMR (CDCl$_3$, 300 MHz, rt, OH resonance not assigned) δ 8.34 (s, 1, CH=NAr), 7.50 and 7.16 (d, 1 each, H$_{aryl}$), 7.10 (d, 2, Ar: H$_m$), 7.01 (t, 1, Ar: H$_p$), 2.22 (s, 6, Ar: Me), 1.49 (s, 9, CMe$_3$), 1.34 (s, 9, C'Me$_3$).

The sodium salt was cleanly synthesized according to the above general procedure: H NMR (300 MHz, THF-d$_8$): 0.51 equiv of THF coordinated.

EXAMPLE 5

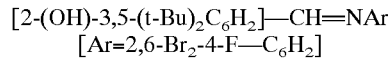

The general procedure for imine synthesis was followed using 2.12 g (9.05 mmol) of 3,5-di-t-butyl-2-hydroxybenzaldehyde and 1.89 g (10.8 mmol, 1.20 equiv) of 2,6-dibromo-4-fluoroaniline. A yellow powder (1.11 g, 25.5%) was isolated: $^1$H NMR (CDCl$_3$, 300 MHz, rt, OH resonance not assigned) δ 8.45 (s, 1, CH=NAr), 7.54 (d, 1, H$_{aryl}$), 7.40 (d, 2, J$_{HF}$ ~9, Ar: H$_m$), 7.19 (d, 1, H$_{aryl}$), 1.50 (s, 9, CMe$_3$), 1.35 (s, 9, C'Me$_3$).

The sodium salt was cleanly synthesized according to the above general procedure: 1H NMR (300 MHz, THF-d$_8$): 0.58 equiv of THF coordinated.

EXAMPLE 6

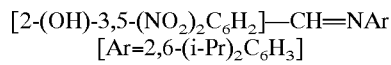

The general procedure for imine synthesis was followed using 4.98 g (23.5 mmol) of 3,5-dinitro-2-hydroxybenzaldehyde and 4.16 g (23.5 mmol) of 2,6-diisopropylaniline. A yellow powder (6.38 g, 73.1%) was isolated: $^1$H NMR (CDCl$_3$, 300 MHz, rt, OH resonance not assigned) δ 9.06 (d, 1, H$_{aryl}$), 8.52 (d, 1, H$_{aryl}$), 8.31 (d, 1, J~6, CH=NAr), 7.40 (t, 1, Ar: H$_p$), 7.30 (d, 2, Ar: H$_m$), 2.96 (septet, 2, CHMe$_2$), 1.25 (d, 12, CHMe$_2$).

The sodium salt was cleanly synthesized according to the above general procedure: $^1$H NMR (300 MHz, THF-d$_8$): 0.57 equiv of THF coordinated.

EXAMPLE 7

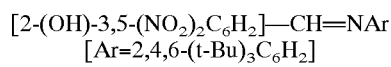

The general procedure for imine synthesis was followed using 3.00 g (14.1 mmol) of 3,5-dinitro-2-hydroxybenzaldehyde and 3.88 g (14.9 mmol, 1.06 equiv) of 2,4,6-tris (t-butyl)aniline. A yellow powder (4.78 g, 74.5%) was isolated: $^1$H NMR (CDCl$_3$, 300 MHz, rt, OH resonance not assigned) δ 9.09 (d, 1, H$_{aryl}$), 8.41 (d, 1, H$_{aryl}$), 8.16 (d, 1, J~12, CH=NAr), 7.48 (s, 1, Ar: H$_m$), 1.38 (s, 18, CMe$_3$), 1.36 (s, 9 C'Me$_3$).

The sodium salt was cleanly synthesized according to the above general procedure: $^1$H NMR (300 MHz, THF-d$_8$): 2 equiv of THF coordinated.

EXAMPLE 8

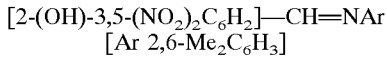
[Ar 2,6-Me$_2$C$_6$H$_3$]

The general procedure for imine synthesis was followed using 3.11 g (14.7 mmol) of 3,5-dinitro-2-hydroxybenzaldehyde and 1.96 g (16.1 mmol, 1.10 equiv) of 2,6-dimethylaniline. A yellow powder (3.63 g, 78.4%) was isolated: $^1$H NMR (CDCl$_3$, 300 MHz, rt, OH resonance not assigned) δ 9.05 (d, 1, H$_{aryl}$), 8.52 (d, 1, H$_{aryl}$), 8.42 (d, 1, J~9, CH=NAr), 7.22 (m, 3, Ar: H$_p$ and H$_m$), 2.36 (s, 6, Ar: Me).

The sodium salt was cleanly synthesized according to the above general procedure: $^1$H NMR (300 MHz, THF-d$_8$): 0.25 equiv of THF coordinated.

EXAMPLE 9

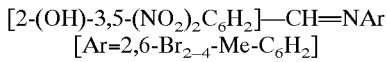
[Ar=2,6-Br$_{2-4}$-Me-C$_6$H$_2$]

The general procedure for imine synthesis was followed using 3.10 g (14.6 mmol) of 3,5-dinitro-2-hydroxybenzaldehyde and 4.64 g (17.5 mmol, 1.20 equiv) of 2,6-dibromo-4-methylaniline. A yellow powder (5.15 g, ~76.8%) was isolated. The $^1$H NMR spectrum of the product showed the presence of methanol, so the powder was dissolved in THF in the drybox under a nitrogen atmosphere and the solution was placed over molecular sieves for several days. The solution was then filtered through a frit with Celite® and the solvent was removed in vacuo: $^1$H NMR (CDCl$_3$, 300 MHz, rt; OH resonance not assigned; ~1 equiv of THF is present) δ 8.95 (d, 1, J=2.8, H$_{aryl}$), 8.76 (s, 1, CH=NAr), 8.71 (d, 1, J=2.8, H$_{aryl}$), 7.43 (s, 2, Ar: H$_m$), 2.31 (s, 3,Ar: Me).

The sodium salt was cleanly synthesized according to the above general procedure: $^1$H NMR (300 MHz, THF-d$_8$): 3 equiv of THF coordinated.

EXAMPLE 10

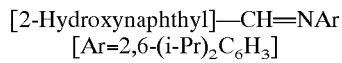
[Ar=2,6-(i-Pr)$_2$C$_6$H$_3$]

The general procedure for imine synthesis was followed using 20.1 g (117 mmol) of 2-hydroxy-1-naphthaldehyde and 24.8 g (140 mmol, 1.20 equiv) of 2,6-diisopropylaniline. A yellow-gold powder (30.8 g, 79.5%) was isolated: $^1$H NMR (CDCl$_3$, 300 MHz, rt) δ 15.30 (d, 1, OH), 9.15 (d, 1, CH=N), 8.08 (d, 1, H$_{naphthyl}$), 7.98 (d, 1, H$_{naphthyl}$), 7.88 (d, 1, H$_{naphthyl}$), 7.60 (t, 1, H$_{naphthyl}$), 7.45 (t, 1, H$_{naphthyl}$), 7.35 (m, 3, Ar: H$_m$ and H$_p$), 7.29 (d, 1, H$_{naphthyl}$), 3.20 (septet, 2, CHMe$_2$), 1.33 (d, 12, CHMe$_2$).

The sodium salt was cleanly synthesized according to the above general procedure $^1$H NMR (300 MHz, THF-d$_8$): 0.5 equiv of THF coordinated.

EXAMPLE 11

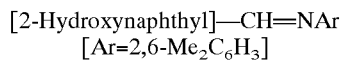
[Ar=2,6-Me$_2$C$_6$H$_3$]

The general procedure for imine synthesis was followed using 33.7 g (196 mmol) of 2-hydroxy-1-naphthaldehyde and 28.4 g (235 mmol, 1.20 equiv) of 2,6-dimethylaniline. A golden yellow powder (47.2 g, 87.5%) was isolated: $^1$H NMR (CDCl$_3$, 300 MHz, rt, OH resonance not assigned) 5 9.23 (d, 1, N=CH), 8.4–7.1 (m, 9, H$_{aryl}$), 2.41 (s, 6, Ar: Me).

The sodium salt was cleanly synthesized according to the above general procedure: $^1$H NMR (300 MHz, THF-d$_8$): 0.5 equiv of THF coordinated.

EXAMPLE 12

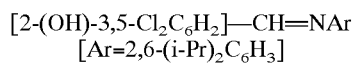
[Ar=2,6-(i-Pr)$_2$C$_6$H$_3$]

The general procedure for imine synthesis was followed using 8.67 g (45.4 mmol) of 3,5-dichloro-2-hydroxybenzaldehyde and 9.66 g (54.5 mmol, 1.20 equiv) of 2,6-diisopropylaniline. A light yellow powder (10.7 g, 67.3%) was isolated: $^1$H NMR (CDCl$_3$, 300 MHz, rt) δ 13.95 (s, 1, OH), 8.20 (s, 1, CH=NAr), 7.50 (d, 1, H$_{aryl}$), 7.18–6.83 (m, 3, H$_{aryl}$), 7.23 (d, 1, H$_{aryl}$), 2.89 (septet, 2, CHMe$_2$), 1.16 (d, 12, CHMe$_2$); $^{13}$C NMR (CDCl$_3$, 75 MHz, rt) δ 165.1 (N=CH), 156.1, 145.0, 138.7, 132.9, 129.8, 128.6, 126.2, 123.4, 123.0 and 119.7 (C$_{aryl}$), 28.3 (CHMe$_2$), 23.6 (CHMe$_2$).

The sodium salt was cleanly synthesized according to the above general procedure: $^1$H NMR (300 MHz, THF-d$_8$)g: 0.5 equiv of THF coordinated.

EXAMPLE 13

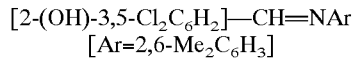
[Ar=2,6-Me$_2$C$_6$H$_3$]

The general procedure for imine synthesis was followed using 16.2 g (85.0 mmol) of 3,5-dichloro-2-hydroxybenzaldehyde and 11.3 g (93.5 mmol, 1.10 equiv) of 2,6-dimethylaniline. A yellow powder (18.2 g, 72.7%) was isolated: $^1$H NMR (CDCl$_3$, 300 MHz, rt) δ 14.15 (s, 1, OH), 8.43 (s, 1, N=CH), 7.65 (d, 1, J=2.5, H$_{aryl}$), 7.41 (d, 1, J=2.5, H$_{aryl}$), 7.30–7.18 (m, 3, Ar: H$_m$ and H$_p$), 2.35 (s, 6, Me).

The sodium salt was cleanly synthesized according to the above general procedure: $^1$H NMR (300 MHz, THF-d$_8$): 0.33 equiv of THF coordinated.

EXAMPLE 14

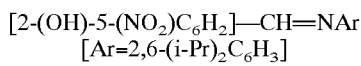
[Ar=2,6-(i-Pr)$_2$C$_6$H$_3$]

The general procedure for imine synthesis was followed using 5.22 g (31.2 mmol) of 5-nitro-2-hydroxybenzaldehyde and 6.65 g (37.5 mmol, 1.20 equiv) of 2,6-diisopropylaniline. A yellow powder (4.39 g, 43.1%) was isolated: $^1$H NMR (CDCl$_3$, 300 MHz, rt, OH resonance not assigned) 8 8.38 (s, 1, CH=NAr), 8.35 (d,. 1, J=3, H'$_m$ to hydroxy), 8.30 (dd, 1, J=9, 3, H$_m$ to hydroxy), 7.23 (s, 3, Ar: H$_m$ and H$_p$), 7.15 (d, 1, J=9, H$_o$ to hydroxy), 2.93 (septet, 2, CHMe$_2$), 1.20 (s, 12, CHMe$_2$).

The sodium salt was cleanly synthesized according to the above general procedure: $^1$H NMR (300 MHz, THF-d$_8$): 0.25 equiv of THF coordinated.

EXAMPLE 15

Pyrrole-2-(CH=NAr) [Ar=2,6-(i-Pr)$_2$C$_6$H$_3$]

The general procedure for imine synthesis was followed using 5.00 g (52.6 mmol) of pyrrole-2-carboxaldehyde and 10.3 g (57.9 mmol, 1.1 equiv) of 2,6-diisopropylaniline. The compound was isolated as an off-white powder: $^1$H NMR (CDCl$_3$, 300 MHz, rt) δ 10.96 (s, 1, NH), 8.05 (s, 1, N=CH), 7.26 (s, 3, Ar: H$_m$, H$_p$), 6.68, 6.29 and 6.24 (m, 1 each, H$_{pyrrole}$), 3.17 (septet, 2, J=6.9, CHMe$_2$), 1.20 (d, 12, J=7.2, CHMe$_2$); $^{13}$C NMR (CDCl$_3$, 75 MHz, rt) δ 152.6 (N=CH), 148.5, 138.9 and 129.9 (pyrrole: C$_{ipso}$; Ar: C$_{ipso}$, C$_o$), 124.5, 124.0, 123.2, 116.5 and 109.9 (pyrrole: 3 CH carbons and Ar: C$_m$, C$_p$), 27.9 (CHMe$_2$), 23.6 (CHMe$_2$).

The sodium salt was cleanly synthesized according to the above general procedure: $^1$H NMR (300 MHz, C$_6$D$_6$/THF-d$_8$): 1 equiv of THF coordinated.

EXAMPLE 16

(Ar) (H)N—C(Me)=CH—C(O)OMe
[Ar=2,6-(i-Pr)$_2$C$_6$H$_3$]

Concentrated HCl (2 drops) was added to a solution of methylacetoacetate (5.2 mL; 48.5 mmol) and 2,6-diisopropylaniline (8.58 g, 48.5 mmol) in methanol. The reaction mixture was stirred at room temperature for 30 h. The product (5.95 g; 45% yield; mp 125–127° C.) was filtered, washed with a small amount of methanol, and then dried under vacuum. Additional product (3.79 g, 28%; mp 115–122° C.) was isolated from the mother liquor: $^1$H NMR (300 MHz, CDCl$_3$, rt): δ 9.78 (br s, 1, NH), 7.29 (t, 1, J=8.1, Ar: H$_p$), 7.17 (d, 2, J=8.2, Ar: H$_m$), 4.71 (s, 1, =CH), 3.70 (s, 3, OMe), 3.10 (septet, 2, J=6.8, CHMe$_2$), 1.61 (s, 3, =CMe), 1.22 (d, 6, J=6.8, CHMeMe'), 1.1.5 (d, 6, J=6.7, CHMeMe').

The sodium salt was cleanly synthesized according to the above general procedure: $^1$H NMR (300 MHz, THF-d$_8$): no THF coordinated.

EXAMPLES 17–40

Synthesis of Nickel Complexes

General Synthesis of Nickel Allyl Initiators. A mixture of two equiv of the appropriate anionic ligand and one equiv of [(allyl)Ni(μ-X)]$_2$ (X=Cl or Br) was dissolved in THF. The reaction mixture was stirred for several h before being filtered. The solvent was removed in vacuo to yield the desired product. Depending on the solubility of the product, further purification was often carried out by dissolving the product in Et$_2$O or pentane and filtering again or washing the product with Et$_2$O or pentane. Due to ease of characterization and, especially, ease of initiation in the presence of a Lewis acid, typically allyl=(a) H$_2$CC(CO$_2$Me)CH$_2$. However, other allyl derivatives were also synthesized and their polymerization activity explored; these include allyl= (b) H$_2$CCHCH$_2$, (c) H$_2$CCHCHMe, (d) H$_2$CCHCMe$_2$, (f) H$_2$CCHCHCl, and (g) H$_2$CCHCHPh. The [(allyl)Ni(μ-X)]$_2$ precursors were synthesized according to the procedures published in the following reference: Wilke, G.; Bogdanovic, B.; Hardt, P.; Heimbach, P; Keim, W.; Kroner, M.; Oberkirch, W.; Tanaka, K.; Steinrucke, E.; Walter, D.; Zimmermann, H. *Angew. Chem. Int. Ed. Engl.* 1966, 5, 151–164.

Complexes 1–20 were synthesized according to the above general procedure and their structures, syntheses and characterization follow:

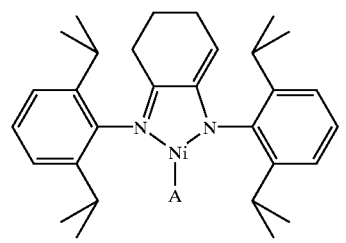

1

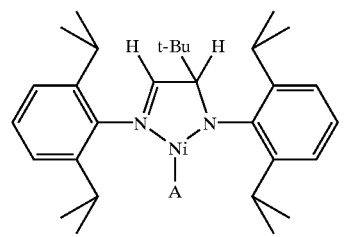

2

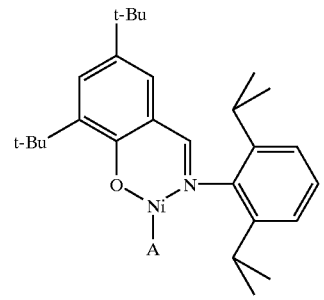

3

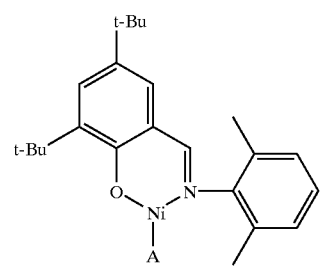

4

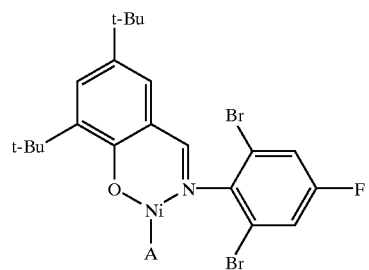

5

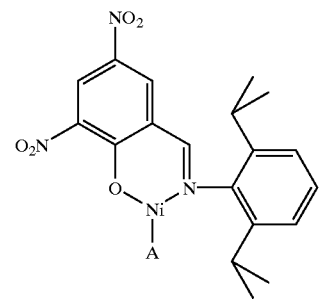

6

-continued

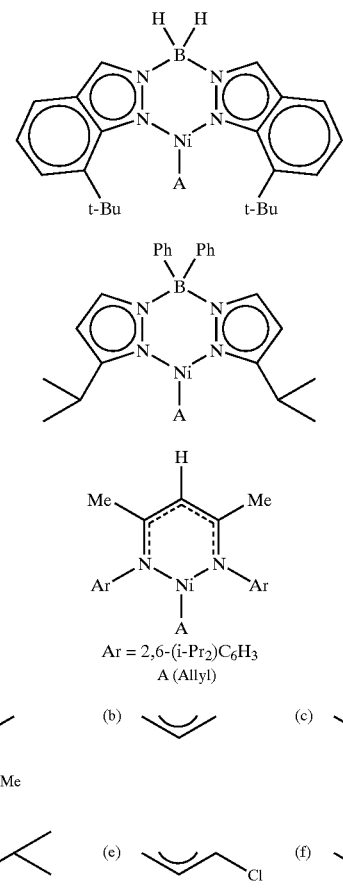

Ar = 2,6-(i-Pr$_2$)C$_6$H$_3$
A (Allyl)

EXAMPLE 17

Complex 1a. Two equiv (610 mg, 1.35 mmol) of the sodium salt of the ligand were reacted with one equiv (321 mg, 0.674 mmol) of [(allyl)Ni($\mu$-Br)]$_2$ (allyl=H$_2$CC(CO$_2$Me)CH$_2$) to give 655 mg (82.6% yield) of a deep purple powder.

EXAMPLE 18

Complex 1d. Two equiv (667 mg, 1.47 mmol) of the sodium salt of the ligand were reacted with one equiv (306 mg, 0.737 mmol) of [(allyl)Ni($\mu$-Br)]$_2$ (allyl=H$_2$CCHCMe$_2$) to give a purple solid: $^1$H NMR (C$_6$D$_6$, 300 MHz, rt, H$_2$CCHCMe$_2$ resonances not assigned) δ 7.25–6.79 (m, 6, H$_{aryl}$), 4.93 (t, 1, J=4.6, ArNHC=CH—), 4.56 (br m, 1, H$_2$CCHCMe$_2$), 3.48 (septet, 2, J=6.9, CHMe$_2$), 2.99 (septet, 2, J=6.9, C'HMe$_2$), 2.07 (m, 2, Cy: CH$_2$), 1.92 (m, 2, Cy: CH$_2$), 1.42 (m, 2, Cy: CH$_2$), 1.2–1.1 (doublets, 24, CHMe$_2$, C'HMe$_2$), 0.72 and 0.61 (br s, 3 each, H$_2$CCHCMeMe').

EXAMPLE 19

Complex 2a. Two equiv (1.08 g, 2.44 mmol) of the lithium salt of the ligand were reacted with one equiv (581 mg, 1.22 mmol) of [(allyl)Ni($\mu$-Br)]$_2$ (allyl=H$_2$CC(CO$_2$Me)CH$_2$) to yield 1.35 g (93.8% yield) of a red powder. $^1$H NMR spectrum in C$_6$D$_6$ is complex.

EXAMPLE 20

Complex 3a. Two equiv (4.01 g, 8.71 mmol) of the sodium salt of the ligand were reacted with one equiv (2.07 g, 4.35 mmol) of [(allyl)Ni($\mu$-Br)]$_2$ (allyl=H$_2$CC(CO$_2$Me)CH$_2$) to yield 3.61 g (75.2% yield) of a golden yellow powder. $^1$H NMR (C$_6$D$_6$, 300 MHz, rt) δ 7.84 (s, 1, N=CH), 7.44 and 6.92 (d, 1 each, H$_{aryl}$), 7.20 (m, 3, Ar: H$_m$, H'$_m$ and H$_p$), 3.88 (d, 1, HH'CC(CO$_2$Me)CHH'), 3.86 (septet, 1, CHMe$_2$), 3.80 (s, 3, OMe), 3.04 (septet, 1, C'HMe$_2$), 2.91 (s, 1, HH'CC(CO$_2$Me)CHH'), 1.89 (m, 1, HH'CC(CO$_2$Me)CHH'), 1.43 (s, 1, HH'CC(CO$_2$Me)CHH'), 1.41 and 1.25 (s, 9 each, CMe$_3$ and C'Me$_3$), 1.37, 1.27, 1.16 and 1.02 (d, 3 each, CHMeMe' and C'HMeMe'); $^{13}$C NMR (CD$_2$Cl$_2$, 75 MHz, rt) δ 166.6 (N=CH), 167.4, 164.7, 153.0, 141.3, 140.9, 139.9, 136.5, 117.7 and 110.9 (H$_2$CC(CO$_2$Me)CH$_2$; Ar: C$_{ipso}$, C$_o$, C'$_o$; Ar': C$_{ipso}$, C$_o$, C$_m$, C'$_m$), 130.2, 127.9, 126.8, 124.0 and 123.9 (Ar: C$_m$, C'$_m$, C$_p$; Ar': Cp and C'$_o$), 59.8 and 47.0 (H$_2$CC(CO$_2$Me)CH$_2$), 53.1 (CO$_2$Me), 35.9 and 34.3 (CMe$_3$ and C'Me$_3$), 31.6 and 30.0 (CMe$_3$ and C'Me$_3$), 29.0, 28.5, 25.7, 25.6, 23.3 and 22.7 (CHMeMe' and C'HMeMe').

Single crystals were formed by cooling a pentane solution of the complex to −35° C. in the drybox freezer. The structure of the compound was solved by X-ray crystallography and is in agreement with the proposed structure.

EXAMPLE 21

Complex 4a. Two equiv (834 mg, 2.11 mmol) of the sodium salt of the ligand were reacted with one equiv (501 mg, 1.05 mmol) of [(allyl)Ni($\mu$-Br)]$_2$ (allyl=H$_2$CC(CO$_2$Me)CH$_2$) to give 935 mg (89.7% yield) of a golden yellow powder: $^1$H NMR (THF-d$_8$, 300 MHz, rt) δ 7.94 (s, 1, N=CH), 7.40 (d, 1, H$_{aryl}$), 7.13–6.92 (m, 3, Ar: H$_m$, H'$_m$, H$_p$), 7.00 (d, 1, H$_{aryl}$), 3.78 (s, 3, OMe), 3.76 (d, 1, HH'CC(CO$_2$Me)CHH'), 2.80 (s, 1, HH'CC(CO$_2$Me)CHH'), 2.45 (s, 3, Ar: Me), 2.10 (s, 3, Ar: Me'), 1.85 (d, 1, HH'C(CO$_2$Me)CHH'), 1.60 (t, 1, HH'CC(CO$_2$Me)CHH'), 1.40 and 1.24 (s, 9 each, CMe$_3$ and C'Me$_3$); $^{13}$C NMR (CD$_2$Cl$_2$, 75 MHz, rt) δ 166.2 (N=CH), 167.3, 164.3, 155.1, 141.1, 136.2, 130.0, 129.4, 118.0 and 110.3 (H$_2$CC(CO$_2$Me)CH$_2$, Ar: C$_{ipso}$, C$_o$, C'$_o$; Ar': C$_{ipso}$, C$_o$, C$_m$, C'$_m$), 129.8, 128.5, 128.4, 127.8 and 125.6 (Ar: C$_m$, C'$_m$, C$_p$; Ar': C$_p$, C'$_o$), 57.8 and 47.7 (H$_2$CC(CO$_2$Me)CH$_2$), 52.8 (OMe), 35.7 and 34.1 (CMe$_3$ and C'Me$_3$), 31.4 and 29.4 (CMe$_3$ and C'Me$_3$), 19.0 and 18.4 (Ar: Me and Me').

EXAMPLE 22

Complex 5a. Two equiv (390 mg, 0.709 mmol) of the sodium salt of the ligand were reacted with one equiv (169 mg, 0.355 mmol) of [(allyl)Ni($\mu$-Br)]$_2$ (allyl H$_2$CC(CO$_2$Me)CH$_2$) to give 189 mg (45.8% yield) of a golden yellow powder: $^1$H NMR (CDCl$_3$, 300 MHz, rt, broad resonances) δ 7.80 (br s, 1, N=CH), 7.50 (br s, 1, H$_{aryl}$), 7.42 (br s, 1, Ar: H$_m$, H'$_m$), 6.96 (br s, 1, H$_{aryl}$), 3.92 (br s, 1, HH'CC(CO$_2$Me)CHH'), 3.86 (br s, 3, OMe), 2.84 (br s, 1, HH'CC(CO$_2$Me)CHH'), 1.98 and 1.76 (br s, 1 each, HH'CC(CO$_2$Me)CHH'), 1.43 and 1.29 (br s, 9 each, CMe$_3$ and C'Me$_3$).

EXAMPLE 23

Complex 6a. Two equiv (900 mg, 2.10 mmol) of the sodium salt of the ligand were reacted with one equiv (500 mg, 1.05 mmol) of [(allyl)Ni($\mu$-Br)]$_2$ (allyl=H$_2$CC(CO$_2$Me)CH$_2$) to give 864 mg (77.9% yield) of a golden yellow powder: $^1$H NMR (C$_6$D$_6$, 300 MHz, rt) δ 8.40 (d, 1, J=3.0, H$_{aryl}$), 7.66 (d, 1, J=3.0, H$_{aryl}$), 7.12 (s, 1, N=CH), 7.10–6.90 (m, 3, Ar: H$_m$, H'$_m$, H$_p$), 4.05 (m, 1, HH'CC(CO$_2$Me)CHH'), 3.49 (septet, 1, J=6.9, CHMe$_2$), 3.21 (s, 3, OMe), 2.96 (septet, 1, J=6.8, C'HMe$_2$), 2.67 (s, 1, HH'CC (CO$_2$Me)CHH'), 2.23 (m, 1, HH'CC(CO$_2$Me)CHH'), 1.34 (br s, 1, HH'CC(CO$_2$Me)CHH'), 1.36, 1.15, 0.95 and 0.84 (d, 3 each, J=6.8, CHMeMe', C'HMeMe').

EXAMPLE 24

Complex 6f. Two equiv (267 mg, 0.621 mmol) of the sodium salt of the ligand were reacted with one equiv (105 mg, 0.310 mmol) of [(allyl)Ni($\mu$-Cl)]$_2$ (allyl=H$_2$CCHCHCl) to give 245 mg (78.3% yield) of a golden yellow powder: $^1$H NMR spectrum in C$_6$D$_6$ is complex.

EXAMPLE 25

Complex 7a. Two equiv (926 mg, 1.49 mmol) of the sodium salt of the ligand were reacted with one equiv (354 mg, 0.745 mmol) of [(allyl)Ni($\mu$-Br)]$_2$ (allyl=H$_2$CC(CO$_2$Me)CH$_2$) to give 861 mg (94.4% yield) of a golden yellow powder: $^1$H NMR (C$_6$D$_6$, 300 MHz, rt) δ 8.43 (d, 1, J=2.6, H$_{aryl}$), 7.81 (d, 1, J=2.9, H$_{aryl}$), 7.48 (s, 2, Ar: H$_m$), 7.45 (s, 1, N=CH), 4.12 (d, 1, J=2.9, HH'C(CO$_2$Me)CHH'), 3.28 (s, 3, OMe), 2.84 (s, 1, HH'C(CO$_2$Me)CHH'), 2.44 (t, 1, J=2.4, HH'C(CO$_2$Me)CHH'), 1.58, 1.41 and 1.28 (s, 9 each, CMe$_3$, C'Me$_3$, C"Me$_3$), 1.31 (d, 1, J=1.1, HH'C(CO$_2$Me)CHH'); $^{13}$$^{13}$C NMR (C$_6$D$_6$, 75 MHz, rt) δ 166.4 (N=CH), 165.5, 162.9, 151.0, 148.1, 144.9, 139.4, 138.8, 134.21, 120.5 and 113.4 (H$_2$CC(CO$_2$Me)CH$_2$; Ar: C$_{ipso}$, C$_o$, C'$_o$, C$_p$; Ar': C$_{ipso}$, C$_o$, C$_m$, C'$_m$), 134.16, 126.1, 125.1 and 124.7 (Ar: C$_m$, C'$_m$ and Ar': C$_p$ and C'$_o$), 63.3 and 49.0 (H$_2$C(CO$_2$Me)CH$_2$), 52.4 (OMe), 37.2 (CMe$_3$), 34.8, 34.4 and 31.4 (CMe$_3$, C'Me$_3$ and C"Me$_3$), (C'Me$_3$ and C"Me$_3$ overlap with CMe$_3$ or CMe$_3$ or C'Me$_3$ resonances).

EXAMPLE 26

Complex 8a. Two equiv (529 mg, 1.49 mmol) of the sodium salt of the ligand were reacted with one equiv (354 mg, 0.745 mmol) of [(allyl)Ni($\mu$-Br)]$_2$ (allyl=H$_2$CC(CO$_2$Me)CH$_2$) to give 662 mg (94.1% yield) of a golden yellow powder: $^1$H NMR (CD$_2$Cl$_2$, 300 MHz, rt) δ 8.80 (d, 1, H$_{aryl}$), 8.40 (d, 1, H$_{aryl}$), 8.08 (s, 1, N=CH), 7.14 (m, 3, Ar: H$_m$, H'$_m$, H$_p$), 3.82 (d, 1, HH'CC(CO$_2$Me)CHH'), 3.88 (s, 3, OMe), 3.00 (s, 1, HH'C(CO$_2$Me)CHH'), 2.46 (s, 3, Ar: Me), 2.16 (m, 1, HH'CC(CO$_2$Me)CHH'), 2.14 (s, 3, Ar: Me'), 1.91 (m, 1, HH'CC(CO$_2$Me)CHH').

EXAMPLE 27

Complex 9a. Two equiv (1.46 g, 2.09 mmol) of the sodium salt of the ligand were reacted with one equiv (497 mg, 1.05 mmol) of [(allyl)Ni($\mu$-Br)]$_2$ (allyl=H$_2$CC(CO$_2$Me)CH$_2$) to give 1.42 g (96.0% yield) of a red powder: $^1$H NMR (CD$_2$Cl$_2$, 300 MHz, rt) δ 8.79 (d, 1, H$_{aryl}$), 8.44 (d, 1, H$_{aryl}$), 8.06 (s, 1, N=CH), 7.51 and 7.49 (s, 1 each, Ar: H$_m$, H'$_m$), 3.96 (d, 1, HH'CC(CO$_2$Me)CHH'), 3.85 (s, 3, OMe), 3.65 (br s, ~1.25 equiv THF), 3.00 (s, 1, HH'CC(CO$_2$Me)CHH'), 2.37 (s, 3, Ar: Me), 2.23 (m, 1, HH'CC(CO$_2$Me)CHH'), 2.13 (s, 1, HH'CC(CO$_2$Me)CHH'), 1.85 (br s, 1.25 equiv THF); $^{13}$C NMR (CD$_2$Cl$_2$, 75 MHz, rt) δ 168.3 (N=CH), 166.0, 163.6, 148.9, 142.7, 140.5, 134.3, 122.0, 117.3, 116.7 and 114.8 (H$_2$CC(CO$_2$Me)CH$_2$; Ar: C$_{ipso}$, C$_o$, C'$_o$, C$_p$; Ar': C$_{ipso}$, C$_o$, C$_m$, C'$_m$), 136.1, 133.5, 133.5 and 126.3 (Ar: C$_m$, C'$_m$; Ar': C$_p$, C'$_o$); 72.6 (br, THF), 61.2 and 51.4 (H$_2$CC(CO$_2$Me)CH$_2$), 53.6 (OMe), 34.9 (br, THF), 20.8 (Ar: Me).

EXAMPLE 28

Complex 10a. Two equiv (490 mg, 1.3 mmol) of the sodium salt of the ligand were reacted with one equiv (300 mg, 0.63 mmol) of [(allyl)Ni($\mu$-Br)]$_2$ (allyl=H$_2$CC(CO$_2$Me)CH$_2$) to give 259 mg (41% yield) of a yellow-green powder. About 12.5% of the isolated sample consists of a second species whose NMR spectrum is consistent with a (ligand)$_2$Ni(II) complex. The remainder is the allyl complex: $^1$H NMR (C$_6$D$_6$, 300 MHz, rt) δ 8.75 (s, 1, N=CH), 7.50–6.90 (m, 8, H$_{aryl}$), 6.03 (d, 1, J=9.2, H$_{aryl}$), 4.16 (d, 1, J=3.0, HH'CC(CO$_2$Me)CHH'), 3.92 (septet, 1, J=6.9, CHMe$_2$), 3.33 (s, 3, OMe), 3.27 (septet, 1, J=6.8, C'HMe$_2$), 2.83 (s, 1, HH'CC(CO$_2$Me)CHH'), 2.77 (dd, 1, J=3.4, 1.6, HH'CC(CO$_2$Me)CHH'), 1.47 (dd, 1, J=1.5, 0.9, HH'CC(CO$_2$Me)CHH'), 1.36, 1.20, 1.02 and 0.92 (d, 3 each, J=6.5–6.8, CHMeMe', C'HMeMe'). [Proposed (ligand)$_2$Ni(II) complex: δ 8.19 (s, 2, N=CH), 7.50–6.90 (m, 16, H$_{aryl}$), 6.12 (d, 2, H$_{aryl}$), 4.54 (septet, 4, J=6.98, CHMe$_2$), 1.53 (d, 12, J=6.8 CHMeMe'), 1.18 (d, 12, CHMeMe').]

EXAMPLE 29

Complex 11a. Two equiv (487 mg, 1.32 mmol) of the sodium salt of the ligand were reacted with one equiv (314 mg, 0.660 mmol) of [(allyl)Ni($\mu$-Br)]$_2$ (allyl=H$_2$CC(CO$_2$Me)CH$_2$) to give 351 mg (61.5% yield) of a yellow-green powder. About 17% of the isolated product consists of a second species whose NMR spectrum is consistent with a (ligand)$_2$Ni(II) complex; the remainder is the allyl complex: $^1$H NMR (C$_6$D$_6$, 300 MHz, rt) δ 8.64 (s, 1, N=CH), 7.41–6.93 (m, 8, H$_{aryl}$), 6.05 (d, 1, J=9.2, H$_{aryl}$), 4.07 (d, 1, J=3.3, HH'CC(CO$_2$Me)CHH'), 3.30 (s, 3, OMe), 2.65 (s, 1, HH'CC(CO$_2$Me)CHH'), 2.28 (s, 3, Ar: Me), 2.16 (s, 4, Ar: Me' and HH'CC(CO$_2$Me)CHH'), 1.41 (br s, 1, HH'CC(CO$_2$Me)CHH'. [Proposed (ligand)$_2$Ni complex: δ 8.01 (s, 2, N=CH), 2.66 (s, 12, Ar: Me).]

EXAMPLE 30

Complex 11b. Two equiv (179 mg, 0.484 mmol) of the sodium salt of the ligand were reacted with one equiv (101 mg, 0.242 mmol) of [(allyl)Ni(g-Br)]$_2$ (allyl=H$_2$CCHCMe$_2$) to give an orange-yellow powder (176 mg, 90.4%): $^1$H NMR (C$_6$D$_6$, 300 MHz, rt) δ 8.65 (s, 1, N=CH), 7.48–6.94 (m, 9, H$_{aryl}$), 5.14 (dd, 1, J=13.0, 7.9, H$_2$CCHCMe$_2$), 2.34 (s, 3, Ar: Me), 2.08 (s, 3, Ar: Me'), 1.40 (d, 1, J=7.7, HH'CCHCMe$_2$), 1.36 (d, 1, J=13.1, HH'CCHCMe$_2$), 1.13 and 1.02 (s, 3 each, H$_2$CCHCMeMe').

EXAMPLE 31

Complex 12a. Two equiv (862 mg, 2.11 mmol) of the sodium salt of the ligand were reacted with one equiv (501 mg, 1.05 mmol) of [(allyl)Ni($\mu$-Br)]$_2$ (allyl H$_2$CC(CO$_2$Me)CH$_2$) to give 951 mg (88.8% yield) of a yellow-green powder. About 10% of the isolated product consists of a second species whose NMR spectrum is consistent with a (ligand)$_2$Ni(II) complex; the remainder is the allyl complex: $^1$H NMR (C$_6$D$_6$, 300 MHz, rt) δ 7.40 (s, 1, N=CH), 7.38–6.98 (m, 5, H$_{aryl}$), 4.13 (d, 1, J=2.9, HH'CC(CO$_2$Me)CHH'), 3.61 (septet, 1, J=6.9, CHMe$_2$), 3.27 (s, 3, OMe), 3.03 (septet, 1, J=6.8, C'HMe$_2$), 2.78 (s, 1, HH'CC(CO$_2$Me)CHH'), 2.16 (t, 1, J=1.7, HH'CC(CO$_2$Me)CHH'), 1.38 (br s, 1, HH'CC(CO$_2$Me)CHH'), 1.34, 1.16, 0.94 and 0.83 (d, 3 each, J=6.6–7.0, CHMeMe', C'HMeMe'); $^{13}$$^{13}$C NMR (C$_6$D$_6$, 75 MHz, rt, diagnostic resonances) δ 165.2 (N=CH), 61.9 and 48.7 (H$_2$CC(CO$_2$Me)CH$_2$), 52.3 (OMe), 28.7 and 28.4 (CHMe$_2$; C'HMe$_2$), 25.3, 25.3, 22.8 and 22.6 (CHMeMe', C'HMeMe'). [Proposed (ligand)$_2$Ni complex: 1H NMR (C$_6$D$_6$) δ 7.20–6.36 (m, 12, N=CH and H$_{aryl}$), 4.49 (septet, 4, J=6.9, CHMe$_2$), 1.42 and 1.13 (d, 12 each, J=7.0, CHMeMe'); $^{13}$$^{13}$C NMR (C$_6$D$_6$) δ 29.6: (CHMe$_2$), 24.4 and 23.6 (CHMeMe').]

EXAMPLE 32

Complex 13a. Two equiv (491 mg, 1.26 mmol) of the sodium salt of the ligand were reacted with one equiv (300 mg, 0.632 mmol) of [(allyl)Ni($\mu$-Br)]$_2$ (allyl H$_2$CC(CO$_2$Me)CH$_2$) to give 469 mg (-82.4% yield) of a green powder. 13% of the isolated product consists of a second species whose NMR spectrum is consistent with a (ligand)$_2$Ni(II) complex; the remainder is the allyl complex: $^1$H NMR (C$_6$D$_6$, 300 MHz, rt) $\delta$ 7.37 (d, 1, J=2.6, H$_{aryl}$), 6.98 (s, 1, N=CH), 6.98–6.86 (m, 3, H$_{aryl}$), 6.56 (d, 1, J=2.0, H$_{aryl}$), 4.05 (d, 1, J=2.6, HH'CC(CO$_2$Me)CHH'), 3.23 (s, 3, OMe), 2.60 (s, 1, HH'CC(CO$_2$Me)CHH', overlaps with Ar: Me of dimer), 2.09 and 2.03 (s, 3 each, Ar: Me, Me'), 2.06 (m, 1, HH'CC(CO$_2$Me)CHH'), 1.31 (s, 1, HH'CC(CO$_2$Me)CHH'). [Proposed (ligand)$_2$Ni(II) complex: $\delta$ 2.60 (s, Ar: Me).]

EXAMPLE 33

Complex 14a. Two equiv (772 mg, 2.11 mmol) of the sodium salt of the ligand were reacted with one equiv (501 mg, 1.05 mmol) of [(allyl)Ni($\mu$-Br)]$_2$ (allyl=H$_2$CC(CO$_2$Me)CH$_2$) to give 891 mg (87.4% yield) of a yellow-orange powder: $^1$H NMR (CD$_2$Cl$_2$, 300 MHz, rt) $\delta$ 8.25 (d, 1, Ar': H$_o$), 8.16 (dd, 1, Ar': H$_p$), 7.98 (s, 1, N=CH), 7.24 (m, 3, Ar: H$_m$, H'$_m$, H$_p$), 6.90 (d, 1, Ar': H$_m$), 3.92 (d, 1, HH'CC(CO$_2$Me)CHH'), 3.86 (s, 3, OMe), 2.99 (septet, 1, CHMe$_2$), 3.02 (s, 1, HH'CC(CO$_2$Me)CHH'), 2.98 (septet, 1, C'HMe$_2$), 2.08 (m, 1, HH'CC(CO$_2$Me)CHH'), 1.66 (t, 1, HH'CC(CO$_2$Me)CHH'), 1.39, 1.31, 1.17 and 1.01 (d, 3 each, CHMeMe' and C'HMeMe').

EXAMPLE 34

Complex 15a. Two equiv (1.09 g, 3.13 mmol) of the sodium salt of the ligand were reacted with one equiv (743 mg, 1.56 mmol) of [(allyl)Ni($\mu$-Br)]$_2$ (allyl=H$_2$CC(CO$_2$Me)CH$_2$) to give 858 mg (66.7% yield) of a yellow-orange powder: $^1$H NMR (C$_6$D$_6$, 300 MHz, rt) $\delta$ 7.20–7.00 (m, 5, N=CH; Ar: H$_m$, H'$_m$, H$_p$; H$_{pyrrole}$), 6.77 (m, 1, H$_{pyrrole}$), 6.42 (m, 1, H$_{pyrrole}$), 3.84 (m, 1, HH'CC(CO$_2$Me)CHH'), 3.65 (septet, 1, J=6.8, CHMe$_2$), 3.30 (s, 3, OMe), 3.19 (septet, 1, J=6.9, C'HMe$_2$), 2.85 (m, 1, HH'CC(CO$_2$Me)CHH'), 2.20 (d, 1, J=0.89, HH'CC(CO$_2$Me)CHH'), 1.89 (d, 1, J=0.89, HH'CC(CO$_2$Me)CHH'), 1.24, 1.18, 1.05 and 0.92 (d, 3 each, J=6.8–7.1, CHMeMe', C'HMeMe'); $^{13}$C NMR (C$_6$D$_6$, 75 MHz, rt) $\delta$ 162.5 (N=CH), 166.2, 148.7, 141.5, 141.4, 141.3, 140.8, 126.5, 123.43, 123.39, 118.8, 114.0 and 109.6 (H$_2$CC(CO$_2$Me)CH$_2$); C$_{aryl}$; C$_{pyrrole}$), 54.0 and 50.3 (H$_2$CC(CO$_2$Me)CH$_2$), 52.1 (OMe), 28.4 and 28.3 (CHMe$_2$, C'HMe$_2$), 25.1, 24.9, 23.0 and 22.5 (CHMeMe' and C'HMeMe').

EXAMPLE 35

Complex 16a. Two equiv (323 mg, 2.15 mmol) of the sodium salt of the ligand were reacted with one equiv (511 mg, 1.07 mmol) of [(allyl)Ni($\mu$-Br)]$_2$ (allyl=H$_2$CC(CO$_2$Me)CH$_2$) to give 322 mg (62.6% yield) of an off-white (slightly red) powder.

EXAMPLE 36

Complex 17a. Two equiv (987 mg, 3.32 mmol) of the sodium salt of the ligand were reacted with one equiv (789 mg, 1.66 mmol) of [(allyl)Ni(4-Br)]$_2$ (allyl=H$_2$CC(CO$_2$Me)CH$_2$) to give 1.14 g (79.4% yield) of a bright yellow-orange powder: $^1$H NMR (C$_6$D$_6$, 300 MHz, rt) $\delta$ 7.06 (br s, 3, H$_{aryl}$), 4.86 (d, 1, J=1.2, ArNC(Me)CHCO$_2$Me), 4.04 (septet, 1, J=6.7, CHMe$_2$), 3.90 (d, 1, J=3.0, HH'CC(CO$_2$Me)CHH'), 3.37 and 3.36 (s, 3 each, (OMe)allyl and (OMe)ligand), 3.24 (septet, 1, J=7.0, C'HMe$_2$), 2.66 (s, 1, HH'CC(CO$_2$Me)CHH'), 2.01 (m, 1, HH'CC(CO$_2$Me)CHH'), 1.44 (s, 3, ArNC(Me)CHCO$_2$Me), 1.36, 1.29, 1.17 and 1.03 (d, 3 each, J=6.2–6.9, CHMeMe', C'HMeMe'), 1.14 (br s, 1, HH'CC(CO$_2$Me)CHH'); $^{13}$C NMR (C$_6$D$_6$, 75 MHz, rt) $\delta$ 170.5, 169.4, 166.7, 151.5, 147.3, 141.1, 140.1, 125.4, 123.7 and 109.2 (Ar: C$_{ipso}$, C$_o$, C$_o$', C$_m$, C$_m$', C$_p$; H$_2$CC(CO$_2$Me)CH$_2$; ArNC(Me)CHCO$_2$Me), 80.2 (ArNC(Me)CHCO$_2$Me), 60.8 and 46.3 (H$_2$CC(CO$_2$Me)CH$_2$), 52.0 and 50.9 (H$_2$CC(CO$_2$Me)CH$_2$, ArNC(Me)CHCO$_2$Me), 28.4 and 28.1 (CHMe$_2$, C'HMe$_2$), 24.5, 24.3, 24.3 and 23.6 (CHMeMe', C'HMeMe'), 23.2 (ArNC(Me)CHCO$_2$Me).

EXAMPLE 37

Complex 18a. Two equiv (1.20 g, 2.14 mmol) of the thallium salt of the ligand were reacted with one equiv (508 mg, 1.07 mmol) of [(allyl)Ni($\mu$-Br)]2 (allyl=H$_2$CC(CO$_2$Me)CH$_2$) to give 730 mg (72.2% yield) of a red powder: H NMR spectrum in C$_6$D$_6$ is complex.

EXAMPLE 38

Complex 19a. Two equiv (435 mg, 1.03 mmol) of the potassium salt of the ligand were reacted with one equiv (245 mg, 0.514 mmol) of [(allyl)Ni($\mu$-Br)]2 (allyl=H$_2$CC(CO$_2$Me)CH$_2$) to give 309 mg (60.4% yield) of a golden yellow powder. Some impurities are present, but the majority of the product is the allyl complex: $^1$H NMR (CD$_2$Cl$_2$, 300 MHz, rt) $\delta$ 7.44 (s, 2, H$_{pyrazole}$), 7.4–7.0 (m, 10, H$_{aryl}$), 6.00 (s, 2, H$_{pyrazole}$), 3.91 (s, 3, OMe), 3.50 (s, 2, HH'CC(CO$_2$Me)CHH'), 2.96 (septet, 2, J=6.8, CHMe$_2$), 1.27 (d, 6, J=7.0, CHMeMe'), 1.19 (d, 6, J=7.0, CHMeMe'), 0.90 (s, 2, HH'CC(CO$_2$Me)CHH').

EXAMPLE 39

Complex 20a. Two equiv (583 mg, 1.32 mmol) of the sodium salt of the ligand were reacted with one equiv (315 mg, 0.662 mmol) of [(allyl)Ni($\mu$-Br)]2 (allyl=H$_2$CC(CO$_2$Me)CH$_2$) to give 407 mg (53.6% yield) of a bright yellow-green powder: $^1$H NMR (C$_6$D$_6$, 300 MHz, rt) $\delta$ 7.11 (m, 6, H$_{aryl}$), 5.04 (s, 1, NC(Me)C(H)C(Me)N), 4.04 (septet, 2, CHMe$_2$), 3.40 (septet, 2, C'HMe$_2$), 3.35 (s, 3, OMe), 2.29 (s, 2, HH'CC(CO$_2$Me)CHH'), 1.95 (s, 2, HH'CC(CO$_2$Me)CHH'), 1.62 (s, 6, NC(Me)C(H)C(Me)N), 1.38, 1.32, 1.20 and 1.07 (d, 6 each, CHMeMe', C'HMeMe').

EXAMPLE 40

Complex 20b. Two equiv (296 mg, 0.672 mmol) of the sodium salt of the ligand were reacted with one equiv (90.8 mg, 0.336 mmol) of [(allyl)Ni($\mu$-Cl)]2 (allyl=H$_2$CCHCH$_2$) to give 151 mg (43.4% yield) of a bright yellow-orange powder: $^1$H NMR (C$_6$D$_6$, 300 MHz, rt) $\delta$ 7.14–7.02 (m, 6, H$_{aryl}$), 5.84 (m, 1, H$_2$CCHCH$_2$), 5.04 (s, 1, NC(Me)C(H)C(Me)N), 4.05 (septet, 2, J=6.9, CHMe$_2$), 3.43 (septet, 2, J=6.9, C'HMe$_2$), 1.79 (d, 2, J=12.8, HH'CCHCHH'), 1.64 (s, 6, NC(Me)C(H)C(Me)N), 1.53 (d, 2, J=6.8, HH'CCHCHH'), 1.39 1.29, 1.21 and 1.10 (d, 6 each, J=6.8–7.1, CHMeMe', C'HMeMe')

EXAMPLES 41–130

Ethylene and Propylene Polymerization Procedures and Reactions

The results of ethylene and propylene polymerizations catalyzed by complexes 1–20 under various reaction conditions (see general procedures and Table 1 below) are reported in Tables 2–5. The polymers were characterized by NMR, GPC, and DSC analysis. A description of the methods used to analyze the amount and type of branching in polyethylene samples by $^{13}$C NMR spectroscopy is given in WO Pat. Appl. 96/23010. GPC's were run in trichlorobenzene at 135° C. and calibrated against polystyrene standards.

General Procedure for the Screening of Ethylene Polymerizations by Nickel Allyl Initiators at 6.9 MPa Ethylene In the drybox, a glass insert was loaded with the isolated allyl initiator. The insert was cooled to −35° C. in the drybox freezer, 5 mL of solvent (typically $C_6D_6$ or $CDCl_3$) was added to the cold insert, and the insert was cooled again. A Lewis acid cocatalyst [typically $BPh_3$ or $B(C_6F_5)_3$] was often added to the cold solution, and the insert was then capped and sealed. Outside of the drybox, the cold tube was placed under ethylene (typically 6.9 MPa) and allowed to warm to rt as it was shaken mechanically for approximately 18 h. An aliquot of the solution was used to acquire a $^1$H NMR spectrum. The remaining portion was added to ~20 mL of MeOH in order to precipitate the polymer. The polyethylene was isolated and dried under vacuum.

General Procedure for the Screening of Ethylene Polymerizations by Nickel Allyl Initiators at 28–35 kPa Ethylene with Polymethylaluminoxane (PMAO) Cocatalyst In the drybox, the nickel complex was placed in a Schlenk flask and dissolved in ~20 mL of toluene. The flask was sealed, removed from the drybox and attached to an ethylene line where it was purged with first nitrogen and then ethylene. After purging with ethylene, PMAO was quickly added to the reaction mixture and the flask was placed under 28–35 kPa of ethylene. After being stirred overnight, the reaction mixture was quenched with 15 mL of a solution of concentrated HCl in methanol (10:90 volume percent solution). The polymer was collected on a frit, washed with methanol and then acetone and then dried in vacuo overnight.

General Procedure for the Screening of Propylene Polymerization by Nickel Allyl Initiators at 48 kPa Propylene with Polymethylaluminoxane (PMAO) Cocatalyst In the drybox, the nickel complex was placed in a Schlenk flask and dissolved in ~10 mL of toluene. The flask was sealed, removed from the drybox and attached to an ethylene line where it was purged with first nitrogen and then propylene. After purging with propylene, PMAO was quickly added to the reaction mixture and the flask was placed under ~48 kPa of propylene. After being stirred overnight, the reaction mixture was quenched with ~10 mL of a solution of concentrated HCl in methanol (10:90 volume percent solution). The polymer was collected on a frit, washed with methanol and then acetone and then dried in vacuo overnight.

General Procedure for the Screening of Propylene Polymerization by Nickel Allyl Initiators at 48 kPa Propylene with $B(C_6F_5)_3$ Cocatalyst In the drybox, the nickel complex was placed in a Schlenk flask and dissolved in ~10 mL of $CH_2Cl_2$. Two equiv of $B(C_6F_5)_3$ were dissolved in a minimal amount of $CH_2Cl_2$ and the solution was transferred to the Schlenk flask. The flask was sealed, removed from the drybox and attached to an ethylene line where it was purged with first nitrogen and then propylene. The flask was placed under ~48 kPa of propylene and the reaction mixture was stirred overnight and then was quenched with ~10 mL of a solution of concentrated HCl in methanol (10:90 volume percent solution). The polymer was collected on a frit, washed with methanol and then acetone and then dried in vacuo overnight

General Procedure for the Screening of Propylene Polymerization by Nickel Allyl Initiators at 600 kPa Propylene With $B(C_6F_5)_3$ Cocatalyst In the drybox, the nickel complex was placed in a vessel and dissolved in ~20 mL of $CH_2Cl_2$. Two equiv of $B(C_6F_5)_3$ were dissolved in ~10 mL of $CH_2Cl_2$ and placed in a separate vessel. Both vessels were sealed and removed from the drybox. The solution of the nickel complex was transferred to a 100 mL Parr reactor under vacuum and the solution of $B(C_6F_5)_3$ was transferred to the addition port of the same reactor. The $B(C_6F_5)_3$ solution was forced into the reactor ~600 kPa of propylene. The reactor pressure was maintained at 600 kPa and the reaction mixture was stirred for 3 h. Next, the reaction mixture was quenched with ~10 mL of a solution of concentrated HCl in methanol (10:90 volume percent solution). If polymer was present, it was collected on a frit, washed with methanol and then acetone and then dried in vacuo overnight. Oligomers were characterized by GC analysis.

TABLE 1

Reaction Conditions Used in Ethylene and Propylene Polymerizations[a]

A  5 mL $C_6D_6$, rt, 18 h, 6.9 MPa E, 2 equiv $BPh_3$
B  5 mL $CDCl_3$, 80° C., 18 h, 6.9 MPa E, 1 equiv $B(C_6F_5)_3$
C  5 mL $C_6D_6$, 80° C., 18 h, 6.9 MPa E, 2 equiv $BPh_3$
D  5 mL $C_6D_6$, rt, 18 h, 6.9 MPa E, 1 equiv $B(C_6F_5)_3$
E  5 mL $C_6D_6$, 80° C., 18 h, 6.9 MPa E, 2 equiv $B[3,5-C_6H_3—(CF_3)_2]_3$
F  5 mL $CDCl_3$, rt, 18 h, 6.9 MPa E, 2 equiv $B[3,5-C_6H_3—(CF_3)_2]_3$
G  5 mL $CDCl_3$, rt, 18 h, 6.9 MPa E, 2 equiv $B(C_6F_5)_3$
H  5 mL $CDCl_3$, 80° C., 18 h, 6.9 MPa E, 2 equiv $B(C_6F_5)_3$
I  20 mL toluene, rt, overnight, 28–35 kPa E, excess PMAO
J  10 mL toluene, rt, overnight, 48 kPa P, excess PMAO
K  10 mL $CH_2Cl_2$, rt, overnight, 48 kPa P, 2 equiv $B(C_6F_5)_3$
L  30 ml $CH_2Cl_2$, rt, 3 h, 600 kPa P, 2 equiv $B(C_6F_5)_3$

[a]Abbreviations. E: Ethylene; P: Propylene; PMAO: Polymethylaluminoxane.

TABLE 2

Polymerization of Ethylene by Compounds 1–20 at 6.9 MPa Ethylene

| | Conditions A (5 mL $C_6D_6$, rt, 18 h, 2 equiv $BPh_3$) | | | Conditions B (5 mL $CDCl_3$, 80° C., 18 h, 1 equiv $B(C_6F_5)_3$) | | |
|---|---|---|---|---|---|---|
| Ex. | Cmpd[b] | PE (g)[c] | TO[d] | Ex. | Cmpd[b] | PE (g)[c] | TO[d] |
| 41 | 1a | 0.43[e] | 260 | 61 | 1a | 0.40[f] | 240 |
| 42 | 2a | [a] | [a] | 62 | 2a | 1.2 | 730 |
| 43 | 3a | 4.1 | 2400 | 63 | 3a | [a] | [a] |
| 44 | 4a | 12.7 | 7500 | 64 | 4a | [a] | [a] |
| 45 | 5a | 5.1 | 3000 | 65 | 5a | [a] | [a] |
| 46 | 6a | 1.3[g] | 590 | 66 | 6a | 1.09 | 650 |
| 47 | 7a | [a] | [a] | 67 | 7a | 0.14 | 81 |
| 48 | 8a | 0.29 | 170 | 68 | 8a | 2.65 | 1600 |
| 49 | 9a | 0.70 | 410 | 69 | 9a | 2.5 | 1500 |
| 50 | 10a | 0.33 | 200 | 70 | 10a | [a] | [a] |
| 51 | 11a | [a] | [a] | 71 | 11a | 0.24 | 140 |
| 52 | 12a | 0.15 | 87 | 72 | 12a | 0.16 | 95 |
| 53 | 13a | [a] | [a] | 73 | 13a | 0.66 | 390 |
| 54 | 14a | 1.1 | 640 | 74 | 14a | 1.2 | 730 |
| 55 | 15a | 0.14 | 80 | 75 | 15a | 0.21 | 120 |

TABLE 2-continued

Polymerization of Ethylene by Compounds 1–20 at 6.9 MPa Ethylene

| | Conditions A (5 mL $C_6D_6$, rt, 18 h, 2 equiv $BPh_3$) | | | | Conditions B (5 mL $CDCl_3$, 80° C., 18 h, 1 equiv $B(C_6F_5)_3$) | | |
|---|---|---|---|---|---|---|---|
| Ex. | Cmpd[b] | PE (g)[c] | TO[d] | Ex. | Cmpd[b] | PE (g)[c] | TO[d] |
| 56 | 16a | a | a | 76 | 16a | 2.3 | 1400 |
| 57 | 17a | 0.52 | 310 | 77 | 17a | 1.33 | 780 |
| 58 | 18a | 0.35 | 590 | 78 | 18a | a | a |
| 59 | 19a | 0.53 | 310 | 79 | 19a | a | a |
| 60 | 20a | 0.14 | 81 | 80 | 20a | a | a |

[a]Less that 0.1 g of polyethylene was isolated.
[b]0.06 mmol
[c]PE: Polyethylene.
[d]TO: number of turnovers per metal center = (moles ethylene consumed, as determined by the weight of the isolated polymer or oligomers) divided by (moles catalyst).
[e]1 equiv of $B(C_6F_5)_3$ was used (Conditions D in Table 1).
[f]5 mL $C_6D_6$ and 2 equiv $BPh_3$ were used (Conditions C in Table 1).
[g]1 equiv $BPh_3$ was used.

TABLE 4

Polyethylene Yields: Demonstration of Effects of Reaction Conditions and Reproducibility of Yields Using Rapid Screening Techniques with Compound 6

| | | Polyethylene Yield (g) | | | | |
|---|---|---|---|---|---|---|
| Ex. | Reaction Conditions[b] | Run 1 | Run 2 | Run 3 | Run 4 | Run 5 |
| 109–113 | A: 5 mL $C_6D_6$, rt, 18 h, 6.9 MPa E, 2 equiv $BPh_3$ | a | 0.10 | 0.10 | a | 1.3[c] |
| 114–115 | B: 5 mL $CDCl_3$, 80° C., 18 h, 6.9 MPa E, 1 equiv $B(C_6F_5)_3$ | 0.10 | 0.28 | | | |
| 116–118 | C: 5 mL $C_6D_6$, 80° C., 18 h, 6.9 MPa E, 2 equiv $BPh_3$ | 9.50 | 9.55 | 0.49[d] | | |
| 119–121 | G: 5 mL $CDCl_3$, rt, 18 h, 6.9 MPa E, 2 equiv $B(C_6F_5)_3$ | a | 0.65 | 7.78 | | |
| 122–123 | H: 5 mL $CDCl_3$, 80° C., 18 h, 6.9 MPa E, 2 equiv $B(C_6F_5)_3$ | 1.09 | 1.09 | | | |

[a]Less than 0.1 g of polyethylene was isolated.
[b]E: Ethylene; $H^2(CO_2Me)CH_2$ initiator was used unless otherwise noted.
[c]1 equiv of $BPh_3$ was used.
[d]$H_2CCHCHCl$ allyl initiator was used.

TABLE 3

Characterization of Polyethylenes Produced by Complexes 1–20

| Ex. | Cmpd (Conds) | Mw | Mn | PDI | Tm (° C.) | NMR Analysis (Branching per 1000 $CH_2$) |
|---|---|---|---|---|---|---|
| 81 | 1a(C) | 703000 | 6640 | 106 | | $^1$H NMR: 16.5 Total Methyls |
| 82 | 1a(D) | 1320000 | 16100 | 81.6 | | $^{13}$C NMR: 74.0 Total Methyls; Branch Lengths: Methyl (38.7), Ethyl (11.0), Propyl (5.3), Butyl (5.9), Amyl (3), ≧Hex[b] (4.5), ≧Am[b] (11.3), ≧Bu[b] (21.4) |
| 83 | 1a(E) | 259000 | 6550 | 39.5 | 68[c] 110 | $^1$H NMR: 54.9 Total Methyls |
| 84 | 2a(B) | 21100 | 2840 | 7.44 | 101 | $^{13}$C NMR: 58.4 Total Methyls; Branch Lengths: Methyl (37.5), Ethyl (4.3), Propyl (2.3), Butyl (2), Amyl (2.4), ≧Hex[b] (9.9), ≧Am[b] (11.8), ≧Bu[b] (14.4) |
| 85 | 3a(A) | | | | 120 | $^{13}$C NMR: 27.9 Total Methyls; Branch Lengths: Methyl (21.7), Ethyl (2.4), Propyl (0.5), Butyl (0.7), Amyl (0.4), ≧Hex[b] (2.6), ≧Am[b] (2.5), ≧Bu[b] (3.3) |
| 86 | 4a(A) | | | | | $^{13}$C NMR: 52.0 Total Methyls; Branch Lengths: Methyl (38.0), Ethyl (2.3), Propyl (2.5), Butyl (2.9), Amyl (2.5), ≧Hex[b] (3.0), ≧Am[b] (6.0), ≧Bu[b] (5.4) |
| 87 | 5a(A) | 88600 | 11100 | 7.95 | | $^{13}$C NMR: 94.7 Total Methyls; Branch Lengths: Methyl (66.7), Ethyl (12.5), Propyl (0.5), Butyl (3.0), Amyl (3.3), ≧Hex[b] (6.0), ≧Am[b] (10.0), ≧Bu[b] (9.8) |
| 88 | 6a(A) | d | d | d | | $^{13}$C NMR: 6.4 Total Methyls; Branch Lengths: Methyl (5.5) |
| 89 | 6a(C-1) | 19,600 | 7580 | 2.58 | | $^1$H NMR: 30.2 Total Methyls |
| 90 | 6a(C-2) | 12,700 | 3680 | 3.45 | 108 | $^{13}$C NMR: 38.8 Total Methyls; Branch Lengths: Methyl (23.1), Ethyl (4.0), Propyl (1.8), Butyl (0), Amyl (0.9), ≧Hex[b] (2.6), ≧Am[b] (5.7), ≧Bu[b] (9.6) |
| 91 | 6a(E) | 10800 | 2910 | 3.71 | 101 | $^1$H NMR: 42.8 Total Methyls |
| 92 | 6a(F) | 128000 | 9040 | 14.1 | 131 | $^1$H NMR: 3.1 Total Methyls |
| 93 | 7a(B) | 22300 | 6170 | 3.62 | 127 | |
| 94 | 8a(A) | d | d | d | 130 | |
| 95 | 8a(B) | 8770 | 1600 | 5.47 | 80 | $^{13}$C NMR: 68.0 Total Methyls; Branch Lengths: Methyl (41.1), Ethyl (8.8), Propyl (0.5), Butyl (2.6), Amyl (5.6), ≧Hex[b] (9.9), ≧Am[b] (14.7), ≧Bu[b] (16.8) |
| 96 | 9a(A) | d | d | d | 130 | $^{13}$C NMR: 18.7 Total Methyls; Branch Lengths: Methyl (16.0) |
| 97 | 9a(B) | 60800 | 590 | 103 | 124 | $^{13}$C NMR: 119.0 Total Methyls; Branch Lengths: Methyl (66.0), Ethyl (22.5), Propyl (5.0), Butyl (8.7), Amyl (7.5), ≧Hex[b] (15.5), ≧Am[b] (23.9), ≧Bu[b] (28.4) |
| 98 | 10a(A) | 25600 | 6180 | 4.14 | 128 | $^1$H NMR: 11.4 Total Methyls |
| 99 | 11a(B) | 77500 | 3090 | 25.1 | 119 | |
| 100 | 13a(B) | 15500 | 3580 | 4.33 | 97 | |
| 101 | 14a(A) | d | d | d | 129 | |
| 102 | 14a(B) | 68900 | 3070 | 22.4 | 78 | |
| 103 | 15a(B) | 23800 | 7560 | 3.15 | 129 | $^1$H NMR: 57.8 Total Methyls |
| 104 | 16a(B) | 69400 | 885 | 78.4 | 117 | $^{13}$C NMR: 48 Total Methyls; Branch Lengths: Methyl (24.8), Ethyl (5.9), Propyl (1), Butyl (2.6), Amyl (6), ≧Hex[b] (11.8), ≧Am[b] (14.2), ≧Bu[b] (16.3) |
| 105 | 17a(A) | d | d | d | 132 | $^1$H NMR: 19.5 Total Methyls |
| 106 | 17a(B) | 325000 | 2080 | 156 | 128 | $^{13}$C NMR: 25.2 Total Methyls; Branch Lengths: Methyl (17.9), Ethyl (4.3), Propyl (1.3), Butyl (1.9), Amyl (2.5), ≧Hex[b] (3.7), ≧Am[b] (4.4), ≧Bu[b] (0.8) |
| 107 | 18a(A) | 24800 | 8730 | 2.84 | | $^1$H NMR: 22.8 Total Methyls |
| 108 | 19a(A) | 90600 | 1630 | 55.7 | 123 | $^{13}$C NMR: 47.4 Total Methyls; Branch Lengths: Methyl (23.7), Ethyl (5.6), Propyl (1.4), Butyl (2.1), Amyl (6.6), ≧Hex[b] (12.7), ≧Am[b] (14.8), ≧Bu[b] (16.7) |

[a]Reaction conditions are given in Table 1.
[b]Includes ends of chains.
[c]Heterogeneous conditions in the glass insert during mixing can account for the observation of two Tm's.
[d]GPC could not be performed due to the insolubility of the sample.

TABLE 5

Polymerization of Ethylene and Propylene at Low Pressures

| Ex. | Cmpd (mmol) | Conds[a] | Gas (kPa)[b] | Polymer (g) | TO[c] | $T_m$ (° C.) |
|---|---|---|---|---|---|---|
| 124 | 1a(0.11) | I | E(27–35) | 2.91 | 970 | d |
| 125 | 6a(0.12) | I | E(27–35) | 0.42 | 128 | 125 |
| 126 | 15a(0.15) | I | E(27–35) | 0.11 | 27 | 121[e] |
| 127 | 20a(0.11) | I | E(27–35) | 0.27 | 88 | f |
| 128 | 1a(0.06) | J | P(48) | 1.84 | 730 | g |
| 129 | 1a(0.06) | K | P(48) | 0.21 | 81 | h |
| 130 | 6a(0.06) | L | P(600) | 11.2[i] | 4400[i] | j |

[a]Reaction conditions are defined in Table 1.
[b]E: Ethylene. P: Propylene.
[c]TO: number of turnovers per catalyst center = (moles monomer consumed, as determined by the weight of the isolated polymer or oligomers) divided by (moles catalyst).
[d]Clear, rubbery amorphous PE.
[e]White, rubbery PE.
[f]White, crystalline PE.
[g]Clear rubbery PP.
[h]Clear sticky PP.
[i]14 mL of liquid oligomers were isolated. A density of 0.8 g/mL was assumed.
[j]GC analysis indicates that pentamers, hexamers and heptamers predominate.

EXAMPLES 131–136

Styrene and Norbornene Homo- and Copolymerizations

In the subsequent examples describing polymerizations of styrene and norbornene, all 5 manipulations were carried out in a nitrogen-purged drybox. Anhydrous solvents were used. The styrene (99+%, Aldrich, inhibited with 4-tert-butylcatechol) was degassed, filtered through basic alumina and inhibited with phenothiazine (98+%, Aldrich, 50 ppm) before use. The norbornene was purified by vacuum sublimation. Tacticities of polystyrenes were measured according to the following reference: T. Kawamura et al., *Macromol. Rapid Commun.* 1994, 15, 479–486.

General Procedure for Styrene Polymerizations. The nickel complex (0.03 mmol) was slurried in dry toluene (6 mL) and styrene (1.3 mL, 1.18 g, 11.3 mmol) was added. Two equiv of $B(C_6F_5)_3$ were then added with vigorous stirring. The resulting mixture was shaken at rt in the dark for 16 h after which time the sample was removed from the drybox and MeOH was added to precipitate the polymer. The solid polymer was isolated, redissolved in $CHCl_3$ and reprecipitated with MeOH to remove catalyst impurities. The product was then collected on a frit, washed with MeOH and finally with a MeOH/acetone/Irganox® 1010 solution.

General Procedure for Norbornene Polymerizations. The nickel complex (0.03 mmol) was slurried in dry toluene (6 mL) and norbornene (1.6 g, 17.0 mmol) was added. Two equiv of $B(C_6F_5)_3$ were then added with vigorous stirring. The resulting mixture was shaken at rt. After 16 h, the sample was removed from the drybox and MeOH was added to precipitate the polymer. The solid polymer was isolated. The polymer was redissolved or swollen with solvent in order to remove catalyst impurities and then reprecipitated with MeOH. The product was then collected on a frit, washed with MeOH and finally with an acetone/2% Irganox® 1010 solution.

General Procedure for Styrene/Norbornene Copolymerizations. The nickel complex (0.03 mmol) was slurried in dry toluene (5 mL) and a mixture of norbornene (1.17 g, 12.4 mmol) and styrene (1.4 mL, 1.27 g, 12.2 mmol) in toluene (3 mL) was added. Two equiv of $B(C_6F_5)_3$ were then added with vigorous stirring. The resulting mixture was shaken at rt in the dark for 5 h. The sample was then removed from the drybox and MeOH was added to precipitate the polymer. The isolated polymer was dissolved ($CHCl_3$) and reprecipitated (MeOH) to remove the catalyst residue. The product was stirred overnight in acetone to remove polystyrene and then filtered, washed with MeOH and finally with an acetone/2% Irganox® 1010 solution.

TABLE 6

Styrene (S) and Norbornene (N) Homo- and Copolymerizations

| Ex. | Cmpd | Monomers | Yield (%) | TO[a] S | TO[a] N | $M_n$[b] | PDI | % S |
|---|---|---|---|---|---|---|---|---|
| 131 | 3a | S | 79 | 300 | — | 2140 | 1.9 | 100[c] |
| 132 | 6a | S | 54 | 200 | — | 3390 | 1.8 | 100[c] |
| 133 | 3a | N | >95 | — | 570 | d | d | N |
| 134 | 6a | N | >95 | — | 570 | d | d | N |
| 135 | 3a | S, N | 21 | 13 | 170 | 9580 | 2.5 | 8 |
| 136 | 6a | S, N | 7 | 4 | 56 | 15500 | 2.0 | 7 |

[a]Number of turnovers: TO = (moles monomer consumed, as determined by the weight of the isolated polymer) divided by (moles catalyst).
[b]$M_n$ (GPC, TCB 120° C., polystyrene standards).
[c]$^{13}C$ NMR spectroscopy ($CDCl_3$) indicates enrichment in meso diad units relative to atactic polystyrene.
[d]Within 30 min the reaction mixture completely solidified and attempts to redissolve the polymer were unsuccessful. The insolubility of the polymer product indicates that an addition polymer of norbornene was formed.

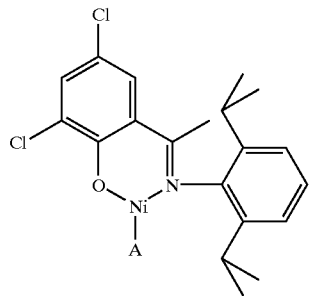

21

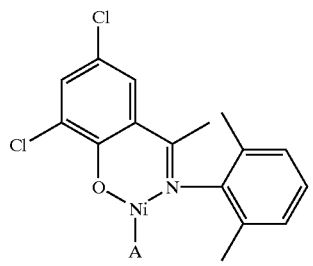

22

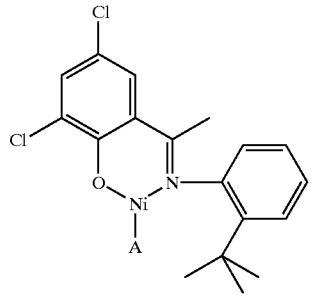

23

-continued

-continued
34
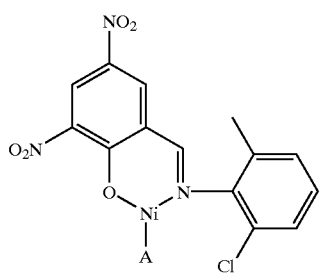
35
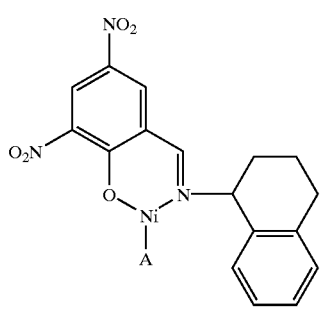
36
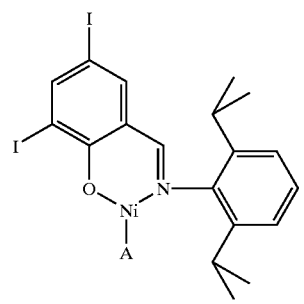
37
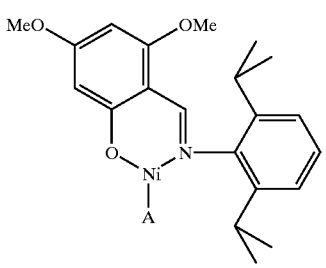
38
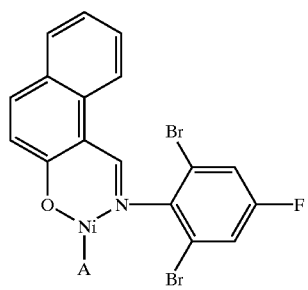
-continued
39
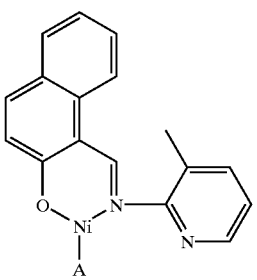
40
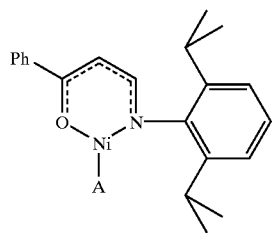
41
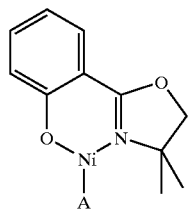
42
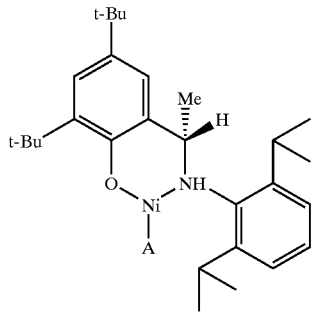
43
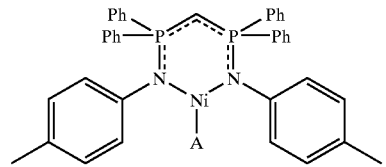
44
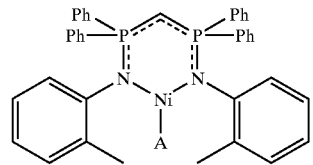
45
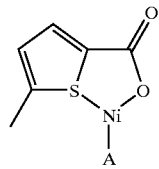

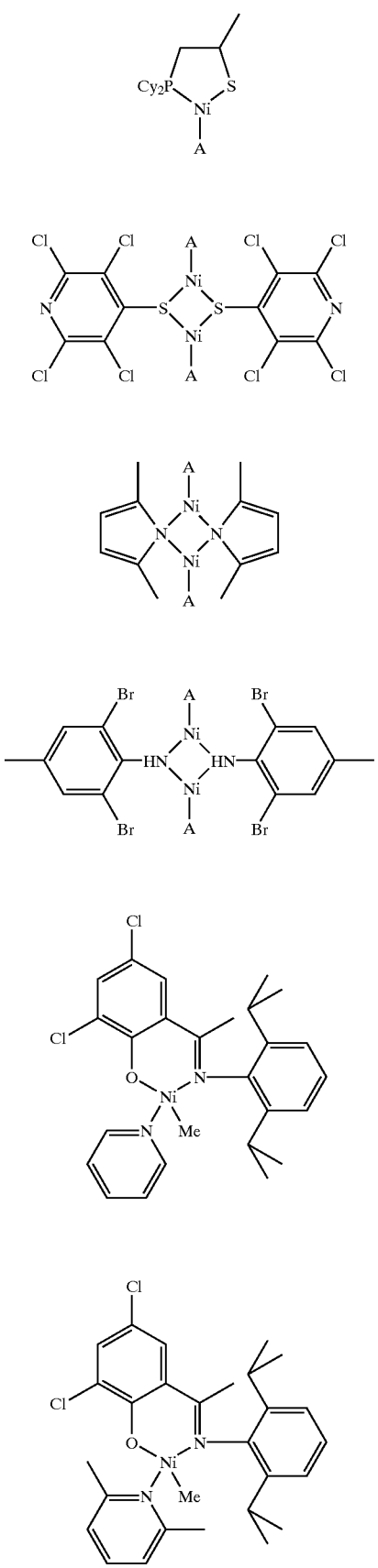
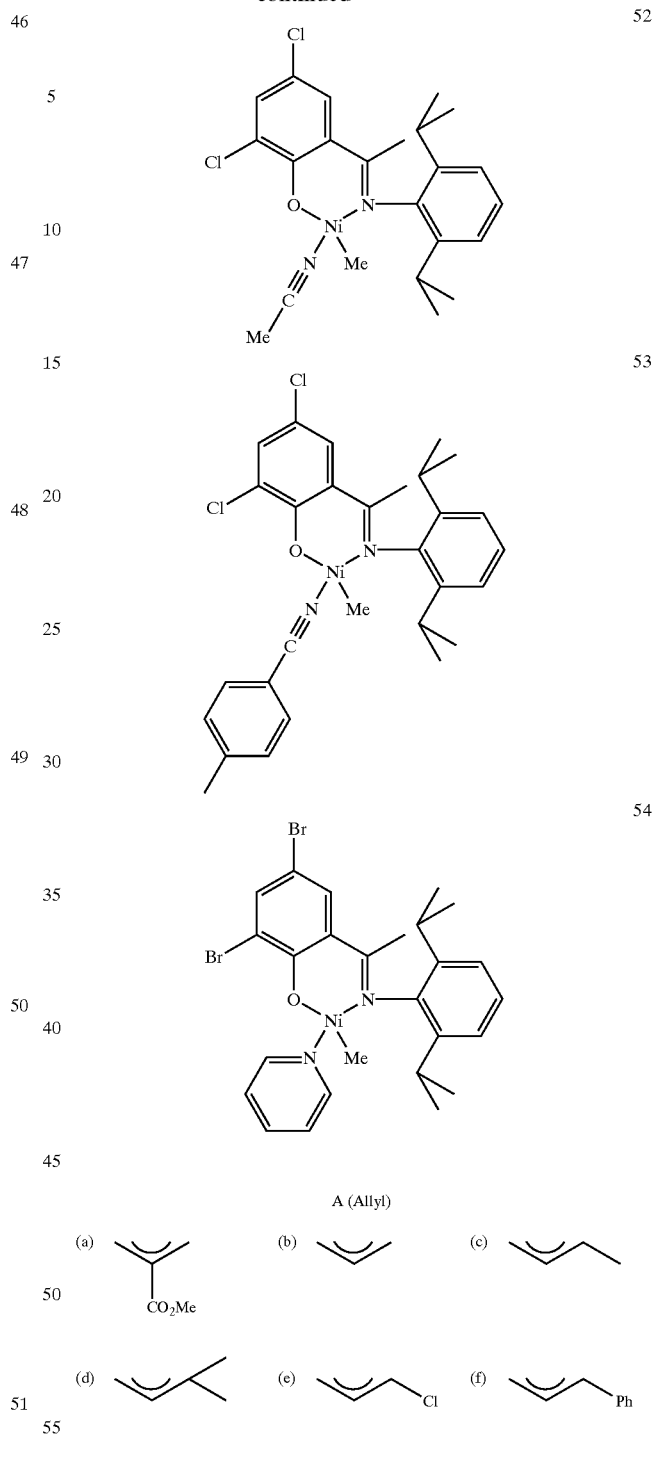

Compounds 21–54. The syntheses and characterization of compounds 21–60 and their ligand precursors are reported in Examples 467 to 498. These compounds are used in the following Examples.

EXAMPLES 137–187

Styrene Homopolymerizations and Styrene/Norbornene Copolymerizations

In the subsequent examples describing polymerizations of styrene and norbornene, all manipulations were carried out in a nitrogen-purged drybox. Anhydrous solvents were used. The styrene (99+%, Aldrich, inhibited with 4-tert-butylcatechol) was degassed, filtered through basic alumina and inhibited with phenothiazine (98+%, Aldrich, 50 ppm) before use. The norbornene was purified by vacuum sublimation. Tacticities of polystyrenes were measured according to the following reference: T Kawamura et al., *Macromol. Rapid Commun.* 1994, 15, 479–486.

General Procedure for Styrene Polymerizations (Table 7). The nickel complex (0.03 mmol) was slurried in dry toluene (6 mL) and styrene (1.6 mL, 14 mmol) was added. Two equiv of $B(C_6F_5)_3$ were then added with vigorous stirring. The resulting mixture was shaken at rt in the dark for 5 h after which time the sample was removed from the drybox and MeOH was added to precipitate the polymer. The solid polymer was isolated, redissolved in $CHCl_3$ and reprecipitated with MeOH to remove catalyst impurities. The product was then collected on a frit, washed with MeOH and finally with a MeOH/acetone/Irganox® 1010 solution. The polymer was then dried under vacuum.

General Procedure for Styrene/Norbornene Copolymerizations (Table 8). The nickel complex (0.03 mmol) was slurried in dry toluene (5 mL) and a mixture of norbornene (1.41 g, 15 mmol) and styrene (1.7 mL, 15 mmol) in toluene (3 mL) was added. Two equiv of $B(C_6F_5)_3$ were then added with vigorous stirring. The resulting mixture was shaken at rt in the dark overnight. The sample was then removed from the drybox and added to MeOH to precipitate the polymer. The product was stirred overnight in acetone to remove polystyrene and then filtered, washed with MeOH and finally with an acetone/2% Irganox 1010 solution. The was then dried under vacuum.

TABLE 7

Styrene Homopolymerizations

| Ex. | Cmpd | Yield (%) | TO[a] | $M_n$[b] | PDI | Tacticity |
|---|---|---|---|---|---|---|
| 137 | 1a | e | e | | | |
| 138 | 2a | e | e | | | |
| 139 | 4a | 41 | 192 | 16,000 | 2.0 | enriched in meso diads[c] |
| 140 | 5a | 61 | 282 | 14,900 | 2.1 | enriched in meso diads[c] |
| 141 | 8a | 15 | 70 | 2,390 | 3.8 | enriched in meso diads[c] |
| 142 | 9a | 0.7 | 3.2 | | | |
| 143 | 14a | 36 | 170 | 2,010 | 5.4 | enriched in meso diads[c] |
| 144 | 15a | 31 | 144 | 1,350 | 2.4 | enriched in meso diads[c] |
| 145 | 16a | e | e | | | |
| 146 | 17a | 9 | 42 | 5,800 | 2.2 | enriched in meso diads[c] |
| 147 | 21a | 72 | 336 | 770 | 2.7 | enriched in meso diads[c] |
| 148 | 22a | 66 | 304 | 760 | 2.7 | enriched in meso diads[c] |
| 149 | 24a | 73 | 340 | 1,010 | 2.9 | enriched in meso diads[c] |
| 150 | 28a | 48 | 221 | 730 | 2.9 | enriched in meso diads[c] |
| 151 | 31a | 57 | 265 | 2,230 | 1.8 | enriched in meso diads[c] |
| 152 | 32a | 78 | 362 | 14,900 | 2.1 | enriched in meso diads[c] |
| 153 | 33a | 26 | 122 | 830 | 2.3 | enriched in meso diads[c] |
| 154 | 35a | 6 | 29 | 18,800 | 5.1 | highly isotactic |
| 155 | 35a[d] | 29 | 134 | 4,150 | 6.8 | highly isotactic |
| 156 | 39a | 4.1 | 19 | | | enriched in r diads[c] |
| 157 | 40a | 58 | 269 | 785 | 3.5 | enriched in meso diads[c] |
| 158 | 42a | 57 | 265 | 800 | 2.8 | enriched in meso diads[c] |
| 159 | 46a | 6 | 29 | 1,980 | 1.4 | highly isotactic |
| 160 | 47b | 15 | 70 | 1,200 | 6.3 | enriched in meso diads[c] |
| 161 | 48a | 48 | 221 | 1,660 | 8.3 | enriched in meso diads[c] |
| 162 | 49a | 9 | 42 | 12,200 | 2.6 | enriched in meso diads[c] |

[a]Number of turnovers: TO = (moles styrene consumed, as determined by the weight of the isolated polymer) divided by (moles catalyst).
[b]$M_n$ (GPC, TCB, 120° C., polystyrene standards).
[c]According to $^{13}C$ NMR spectroscopy ($CDCl_3$) and relative to atactic polystyrene.
[d]60° C.
[e]No polymer was isolated.

TABLE 8

Styrene (S) and Norbornene (N) Copolymerizations

| | | | TO[a] | | | | |
|---|---|---|---|---|---|---|---|
| Ex. | Cmpd | Yield (%) | S | N | $M_n$[b] | PDI | % S |
| 163 | 1a | 4.7 | c | 47 | 5,330 | 5 | <5 |
| 164 | 2a | 40 | c | 400 | 11,000 | 3.9 | <5 |
| 165 | 4a | 43 | 44 | 390 | 7,630 | 3.3 | 11 |
| 166 | 5a | 27 | 15 | 251 | 5,430 | 2.3 | 6.7 |
| 167 | 8a | 14 | c | 141 | 14,300 | 2.7 | <5 |
| 168 | 9a | 8.5 | c | 84 | 8,100 | 2.3 | <5 |
| 169 | 14a | 32 | 17 | 303 | 7,290 | 3.4 | 5.8 |
| 170 | 15a | 36 | 29 | 329 | 7,140 | 3.0 | 9 |
| 171 | 16a | 8.8 | c | 92 | 6,920 | 2.6 | <5 |
| 172 | 17a | 7.8 | c | 78 | 7,060 | 2.3 | <5 |
| 173 | 21a | 44 | 41 | 400 | 2,730 | 3.8 | 10.2 |
| 174 | 22a | 47 | 45 | 425 | 3,340 | 3.3 | 10.5 |
| 175 | 24a | 15 | 5 | 142 | 5,800 | 3.0 | 3.7 |
| 176 | 28a | 45 | 47 | 415 | 2,680 | 3.9 | 11.2 |
| 177 | 31a | 30 | c | 300 | 4,700 | 2.4 | <5 |
| 178 | 32a | 26 | 19 | 236 | 5,670 | 2.2 | 7.5 |
| 179 | 33a | 31 | 13 | 300 | 5,940 | 2.6 | 4.5 |
| 180 | 35a | 7.4 | c | 74 | 20,500 | 2.4 | <5 |
| 181 | 39a | 3.0 | c | 262 | 5,054 | 2.9 | <5 |
| 182 | 40a | 18 | 5 | 172 | 5,960 | 2.9 | 3.0 |
| 183 | 42a | 43 | 31 | 398 | 2,470 | 4.4 | 8.7 |
| 184 | 46a | 38 | c | 379 | 14,800 | 2.8 | <5 |
| 185 | 47b | 17 | c | 170 | 4,570 | 6.2 | <5 |
| 186 | 48a | 8 | c | 78 | 17,600 | 2.5 | <5 |
| 187 | 49a | 15 | c | 145 | 7,500 | 2.3 | <5 |

[a]Number of turnovers: TO = (moles monomer consumed, as determined by the weight of the isolated polymer) divided by (moles catalyst).
[b]$M_n$ (GPC, TCB, 120° C., polystyrene standards).
[c]Low styrene incorporation (<5%) precluded calculation of the styrene turnover numbers.

EXAMPLES 188–194

Norbornene Homopolymerizations and Norbornene/Functionalized-Norbornene Copolymerizations

EXAMPLE 188

Norbornene Homopolymerization Catalyzed by 52/$B(C_6F_5)_3$

In a 20 mL scintillation vial under nitrogen, compound 52 (0.010 g, 0.021 mmol) and norbornene (1.00 g, 10.62 mmol) were dissolved in 5 mL of toluene to give an orange solution. To this was added $B(CEF_5)_3$ (0.011 g, 0.022 mmol). After 30 min at ambient temperature, more $B(C_6F_5)_3$ was added to the reaction mixture (0.110 g, 0.214 mmol). An extremely viscous, yellow suspension formed very rapidly and within minutes the reaction mixture could no longer be stirred. Twenty-three h after the initial addition of $B(C_6F_5)_3$, the reaction mixture was quenched by addition of methanol under air. Further workup afforded 0.93 g of polymer. $^1H$ NMR (1,1,2,2-tetrachloroethane-$d_2$, 120° C.) indicated that the polymer was the addition polymer of norbornene formed without double bond ring-opening.

EXAMPLE 189

Copolymerization of Norbornene With the Dimethyl Ester of Endo-5-norbornene-2,3-Dicarboxylic Acid Catalyzed by 21a/$B(C_6F_5)_3$ (Copolymer: ~30 Mole % Dimethyl Ester)

In a 20 mL scintillation vial under nitrogen, compound 21a (0.015 g, 0.029 mmol), norbornene (0.500 g, 5.31 mmol), and the dimethyl ester of 5-norbornene-2,3- dicarboxylic acid (1.00 g, 4.76 mmol) were dissolved in 10 mL of toluene. To this solution was added solid $B(C_6F_5)_3$ (0.029 g, 0.058 mmol). The resulting solution was stirred initially at ambient temperature by means of a magnetic stirbar; however, after several minutes the reaction mixture consisted of a viscous, solvent-swollen polymer that could not be stirred. Twenty-seven h after the addition of $B(C_6F_5)_3$, the reaction mixture was quenched by addition of the solvent-swollen reaction mixture to methanol under air. The precipitated polymer was filtered off, washed with methanol, and dried to afford 0.810 g of addition copolymer. $^1H$ NMR ($CD_2Cl_2$, 25° C.) indicated the following composition: norbornene (74 mole %), dimethyl ester (26 mole %). Quantitative $^{13}C$ NMR (tr4chlorobenzene-$d_3$, 100° C.) indicated the following composition: norbornene (70.8 mole %), dimethyl ester (29.2 mole %).

EXAMPLE 190

Copolymerization of Norbornene With the Dimethyl Ester of Endo-5-norbornene-2,3-Dicarboxylic Acid Catalyzed by 21a/$B(C_6F_5)_3$ (Copolymer: 22 Mole % Dimethyl Ester)

A reaction identical to that above in Example 189, but run in $CH_2Cl_2$ instead of toluene gave the following results: Yield=0.63 g. $^1H$ NMR ($CDCl_3$, 25° C.) indicated the following composition: norbornene (81%), dimethyl ester (19%). Quantitative $^{13}C$ NMR (trichlorobenzene-$d_3$, 100° C.): norbornene (78.11 mole %), dimethyl ester (21.89 mole %).

EXAMPLE 191

Copolymerization of Norbornene with the Dimethyl Ester of Endo-5-norbornene-2,3-Dicarboxylic Acid Catalyzed by 21a/$B(C_6F_5)_3$ (Copolymer: ~11 mole % Dimethyl Ester)

In a 20 mL scintillation vial under nitrogen, compound 21a (0.015 g, 0.029 mmol), norbornene (3.00 g, 31.86 mmol), the dimethyl ester of 5-norbornene-2,3-dicarboxylic acid (1.00 g, 4.76 mmol), and $B(C_6F_5)_3$ (0.029 g, 0.058 mmol) were dissolved in 10 mL of toluene. The resulting yellow solution was stirred initially at ambient temperature by means of a magnetic stirbar; however, within 15 minutes an extremely rapid, highly exothermic reaction ensued. The reaction mixture setup and could not be stirred after this point. Three h after the addition of $B(C_6F_5)_3$, the reaction mixture was quenched by addition of the solvent-swollen reaction mixture to methanol under air. Further workup afforded 3.75 g of addition copolymer. $^1H$ NMR ($CDCl_3$, 25° C.) indicated the following composition: norbornene (90 mole %), dimethyl ester (10 mole %). Quantitative 13C NMR (trichlorobenzene-$d_3$, 100° C.) indicated the following composition: norbornene (89.05 mole %), dimethyl ester (10.95 mole %).

EXAMPLE 192

Copolymerization of Norbornene With the Dimethyl Ester of Endo-5-norbornene-2,3-Dicarboxylic Acid Catalyzed by 21a/$B(C_6F_5)_3$ (Copolymer: 6 mole % Dimethyl Ester)

A reaction identical to that above in Example 191, but run in $CH_2Cl_2$ instead of toluene gave the following results: Yield=3.12 g. $^1H$ NMR ($CDCl_3$, 25° C.) indicated the following composition: norbornene (96 mole %), dimethyl ester (4 mole %). Quantitative $^{13}C$ NMR (trichlorobenzene-$d_3$, 100° C.): norbornene (94.19 mole %), dimethyl ester (5.81 mole %).

EXAMPLE 193

Copolymerization of Norbornene With the t-Bu Ester of 5-Norbornene-2-Carboxylic Acid Catalyzed by 50/$B(C_6F_5)_3$ (Copolymer: ~30 mole % t-Bu Ester)

In a 20 mL scintillation vial under nitrogen, compound 50 (0.010 g, 0.020 mmol), norbornene (0.500 g, 5.31 mmol), and the t-Bu ester of 5-norbornene-2-carboxylic acid (1.00 g, 5.15 mmol) were dissolved in 5 mL toluene. To this solution was added $B(C_6F_5)_3$ (0.102 g, 0.200 mmol). The resulting yellow solution was stirred at ambient temperature for 16 h. The reaction mixture was quenched and the copolymer precipitated by addition of methanol under air. Further workup afforded 0.664 g of addition copolymer. Quantitative $^{13}C$ NMR (trichlorobenzene-$d_3$, 100° C.) indicated the following composition: norbornene (70.4 mole %), t-Bu ester (29.6 mole %).

EXAMPLE 194

Copolymerization of Norbornene With the Dimethyl Ester of Endo-5-norbornene-2,3-Dicarboxylic Acid Catalyzed by 52/$B(C_6F_5)_3$ (Copolymer: ~32 mole % Dimethyl Ester)

In a 20 mL scintillation vial under nitrogen, compound 52 (0.010 g, 0.021 mmol), norbornene (0.500 g, 5.31 mmol), and the dimethyl ester of 5-norbornene-2,3-dicarboxylic acid (1.00 g, 4.76 mmol) were dissolved in 5 mL of toluene. To this solution was added a suspension of $B(C_6F_5)_3$ (0.029 g, 0.058 mmol) in 5 mL of toluene. The resulting orange solution was stirred initially at ambient temperature by means of a magnetic stirbar; however, after several minutes the reaction mixture consisted of a viscous, solvent-swollen polymer that could not be stirred. Twenty-two h after the addition of $B(C_6F_5)_3$, the reaction mixture was quenched by addition of the solvent-swollen reaction mixture to methanol under air. The precipitated polymer was filtered off, washed with methanol, and dried to afford 0.930 g of addition copolymer. $^1H$ NMR ($CDCl_3$, 25° C.) indicated the following composition: norbornene (68 mole %), dimethyl ester (32 mole %).

EXAMPLES 195–366

Ethylene Polymerizations

General Procedure for Ethylene Polymerizations of Table 9 Pressure Tube Loaded Outside of the Drybox Under a Nitrogen Purge (In the ethylene polymerization reactions of Tables 2, 3, and 4, the glass inserts were also loaded in the pressure reactor tube outside of the drybox under a nitrogen purge.) Procedure. In the drybox, a glass insert was loaded with the isolated allyl initiator (0.06 mmol). The insert was cooled to −35° C. in the drybox freezer, 5 mL of $C_6D_6$ was added to the cold insert, and the insert was cooled again. A Lewis acid cocatalyst [typically $BPh_3$ or $B(C_6F_5)_3$] was added to the cold solution, and the insert was then capped and sealed. Outside of the drybox, the cold insert was placed under a nitrogen purge into the pressure tube. The pressure tube was sealed, placed under ethylene (6.9 MPa), and allowed to warm to rt as it was shaken mechanically for approximately 18 h. An aliquot of the solution was used to acquire a $^1H$ NMR spectrum. The remaining portion was added to ~20 mL of MeOH in order to precipitate the polymer. The polyethylene was isolated and dried under vacuum.

General Procedure for Ethylene Polymerizations of Tables 10–14

Pressure Tube Loaded and Sealed in the Drybox Under a Nitrogen Atmosphere

Procedure. In the drybox, a glass insert was loaded with the nickel compound. Often, a Lewis acid (typically $BPh_3$ or $B(C_6F_5)_3$) was also added to the glass insert. Next, 5 mL of a solvent (typically 1,2,4-trichlorobenzene although p-xylene, cyclohexane, etc. were also used at times) was added to the glass insert and the insert was capped. The glass insert was then loaded in the pressure tube inside the drybox. The pressure tube containing the glass insert was then sealed inside of the drybox, brought outside of the drybox, connected to the pressure reactor, placed under the desired ethylene pressure and shaken mechanically. After the stated reaction time, the ethylene pressure was released and the glass insert was removed from the pressure tube. The polymer was precipitated by the addition of MeOH (~20 mL) and concentrated HCl (~1–3 mL). The polymer was then collected on a frit and rinsed with HCl, MeOH, and acetone. The polymer was transferred to a pre-weighed vial and dried under vacuum overnight. The polymer yield and characterization were then obtained.

TABLE 9

Ethylene Polymerization (6.9 MPa, $C_6D_6$ (5 mL), 0.06 mmol Cmpd, 18 h)

| Ex. | Cmpd | Temp (° C.) | Lewis Acid[a] | PE(g) | PE(TO)[b] | M.W.[c] (MI, GPC, and/or $^1$H NMR) | Total Me[d] |
|---|---|---|---|---|---|---|---|
| 195 | 21a | 25 | $BPh_3$ | 3.34 | 2,000 | MI: 79.5; $M_n$($^1$H): 3,670 | 36.9 |
| 196 | 21a | 80 | $B(C_6F_5)_3$ | e | e | | |
| 197 | 22a | 25 | $BPh_3$ | 4.41 | 2,600 | MI > 200; $M_n$($^1$H): 1,890 | 85.5 |
| 198 | 22a | 80 | $B(C_6F_5)_3$ | 0.04 | 20 | | |
| 199 | 24a | 25 | $BPh_3$ | 15.3 | 9,100 | MI < 0.01; $M_n$($^1$H): no olefins | 4.5 |
| 200 | 24a | 80 | $B(C_6F_5)_3$ | 0.15 | 91 | | |
| 201 | 28a | 25 | $BPh_3$ | 0.30 | 180 | $M_n$($^1$H): 18,900 | 67.1 |
| 202 | 28a | 80 | $B(C_6F_5)_3$ | 0.04 | 24 | | |
| 203 | 31a | 25 | $BPh_3$ | f | f | | |
| 204 | 31a | 80 | $B(C_6F_5)_3$ | f | f | | |
| 205 | 32a | 25 | $BPh_3$ | 0.01[e] | 7[e] | | |
| 206 | 32a | 80 | $B(C_6F_5)_3$ | e | e | | |
| 207 | 33a | 25 | $BPh_3$ | 0.21 | 120 | | |
| 208 | 33a | 80 | $B(C_6F_5)_3$ | 1.60 | 950 | MI: 79.5; $M_n$($^1$H): 1,390 | 51.2 |
| 209 | 35a | 25 | $BPh_3$ | 0.19[e] | 110[e] | | |
| 210 | 35a | 80 | $B(C_6F_5)_3$ | 0.11[e] | 68[e] | | |
| 211 | 37a | 25 | $BPh_3$ | 0.02[e] | 10[e] | | |
| 212 | 38a | 80 | $B(C_6F_5)_3$ | 0.07[e] | 42[e] | | |
| 213 | 39a | 25 | $BPh_3$ | f | f | | |
| 214 | 39a | 80 | $B(C_6F_5)_3$ | 2.11 | 1,300 | MI: 105; $M_n$($^1$H): 5,200 | 21.5 |
| 215 | 40a | 25 | $BPh_3$ | 0.08[e] | 50[e] | | |
| 216 | 40a | 80 | $B(C_6F_5)_3$ | e | e | | |
| 217 | 42a | 25 | $BPh_3$ | e | e | | |
| 218 | 42a | 80 | $B(C_6F_5)_3$ | e | e | | |
| 219 | 46a | 25 | $BPh_3$ | f | f | | |
| 220 | 46a | 80 | $B(C_6F_5)_3$ | 0.11 | 65 | | |
| 221 | 47b | 25 | $BPh_3$ | 0.12[e] | 71[e] | | |
| 222 | 47b | 80 | $B(C_6F_5)_3$ | e | e | | |
| 223 | 47b | 25 | $BPh_3$ | 0.15 | 91 | | |
| 224 | 47b | 80 | $B(C_6F_5)_3$ | 0.09 | 52 | | |
| 225 | 48a | 25 | $BPh_3$ | 0.07 | 43 | | |
| 226 | 48a | 80 | $B(C_6F_5)_3$ | 0.22 | 132[e] | | |
| 227 | 49a | 25 | $BPh_3$ | 0.10 | 59 | | |
| 228 | 49a | 80 | $B(C_6F_5)_3$ | 0.06[e] | 34[e] | | |

[a]Two equiv.
[b]TO: number of turnovers per metal center = (moles ethylene consumed, as determined by the weight of the isolated polymer or oligomers) divided by (moles catalyst).
[c]M.W.: Molecular weight of the polymer or oligomers as determined by melt index (MI: g/10 min at 190° C.), GPC (molecular weights are reported versus polystyrene standards; conditions: Waters 150C, trichlorobenzene at 150° C., Shodex columns at –806MS 4G 734/602005, RI detector), and/or $^1$H NMR (olefin end group analysis).
[d]Total number of methyl groups per 1000 methylene groups determined by $^1$H NMR analysis.
[e]$^1$H NMR: oligomers and/or $(CH_2)_n$ peak observed.
[f]PE was not obtained in isolable quantities.
[g]The general procedure for the screening of ethylene polymerizations by nickel allyl initiators at 6.9 MPa ethylene (see above) was followed.

TABLE 10

Ethylene Polymerizations at 6.9 MPa: Pressure Tube Loaded in the Drybox under
N₂ Atmosphere (Trichlorobenzene (5 mL), 18 h)

| Ex. | Cmpd[f] | Temp (° C.) | Lewis Acid[a] | PE(g) | PE(TO)[b] | M.W.[c] (MI, GPC, and/or $^1$H NMR) | Total Me[d] |
|---|---|---|---|---|---|---|---|
| 229 | 3a | 25 | BPh₃ | 8.31 | 12,900 | MI: 5.5; $M_n$($^1$H): 18,100 | 36.9 |
| 230 | 3a[g] | 25 | BPh₃ | 1.54 | 3,660 | MI: 40; $M_n$($^1$H): no olefins | 20.0 |
| 231 | 3a[g] | 25 | B(C₆F₅)₃ | 0.701 | 1,460 | MI: 22.9; $M_n$($^1$H): 99,900 | 22.9 |
| 232 | 3a | 80 | BPh₃ | 4.29 | 6,640 | MI > 200; $M_n$($^1$H): 4,770 | 56.2 |
| 233 | 3a | 80 | B(C₆F₅)₃ | 0.203 | 359 | Mn($^1$H): 2,500 | 47.7 |
| 234 | 4a | 25 | BPh₃ | 2.44 | 4,630 | MI: 126; $M_n$($^1$H): 10,300 | 43.5 |
| 235 | 4a | 80 | BPh₃ | 2.19 | 3,640 | MI > 200; $M_n$($^1$H): 2,270 | 75.5 |
| 236 | 4a | 80 | B(C₆F₅)₃ | 0.096 | 190 | Mn($^1$H): 3,260 | 29.3 |
| 237 | 5a | 25 | BPh₃ | 4.98 | 8,630 | $M_w$(GPC): 14,100; PDI: 6.7 | 93.2 |
| 238 | 5a | 80 | BPh₃ | 2.72 | 4,710 | $M_n$(GPC): 2,850; PDI: 3.7 | 137.3 |
| 239 | 6a | 25 | BPh₃ | 4.44 | 7,730 | MI: 0.85 | |
| 240 | 6a[i] | 25 | B(C₆F₅)₃ | 6.18 | 5,490 | MI: 1.2; $M_n$($^1$H): 9,620 | 28.5 |
| 241 | 6a[g] | 80 | BPh₃ | 4.13 | 10,500 | MI: 21; $M_n$($^1$H): 12,200 | 28.4 |
| 242 | 6a[h] | 80 | BPh₃ | 13.1 | 7,800 | MI > 200; $M_n$($^1$H): 3,030 | 79.0 |
| 243 | 6a | 80 | B(C₆F₅)₃ | 3.31 | 5,990 | MI: 81; $M_n$($^1$H): 5,920 | 34.7 |
| 244 | 6a[g] | 80 | B(C₆F₅)₃ | 3.14 | 7,300 | MI: 45 | |
| 245 | 6a[h] | 80 | B(C₆F₅)₃ | 8.92 | 5,300 | MI > 200; $M_n$($^1$H): 1,420 | 89.1 |
| 246 | 7a | 25 | BPh₃ | 0.93 | 1,350 | MI < 0.01; $M_n$($^1$H): no olefins | 2.1 |
| 247 | 7a | 25 | B(C₆F₅)₃ | 2.19 | 3,790 | $M_n$($^1$H): 4,160 | 11.6 |
| 248 | 7a | 80 | B(C₆F₅)₃ | 1.36 | 2,030 | MI: 35; $M_n$($^1$H): 1,370 | 35.7 |
| 249 | 8a | 25 | BPh₃ | 3.88 | 6,400 | MI: 120; $M_n$($^1$H): 2,990 | 57.2 |
| 250 | 8a | 25 | B(C₆F₅)₃ | 6.95 | 11,800 | MI: 2.6; $M_n$($^1$H): 6,770 | 57.5 |
| 251 | 8a | 80 | B(C₆F₅)₃ | 3.99 | 7,220 | MI: 132 | |
| 252 | 9a | 25 | BPh₃ | 6.35 | 11,200 | MI > 200; $M_n$($^1$H): 4,910 | 64.9 |
| 253 | 9a | 25 | B(C₆F₅)₃ | 6.32 | 9,900 | MI: 102; $M_n$($^1$H): 5,380 | 91.3 |
| 254 | 9a | 80 | B(C₆F₅)₃ | 4.8 | 8,000 | $M_n$($^1$H): 1,410 | 134.6 |
| 255 | 10a | 25 | BPh₃ | 0.18 | 320 | | |
| 256 | 10a | 80 | BPh₃ | 1.33 | 2,140 | MI: 63; $M_n$($^1$H): 11,100 | 38.3 |
| 257 | 10a | 80 | B(C₆F₅)₃ | 0.097 | 170 | $M_n$($^1$H): 2,010 | 30.4 |
| 258 | 11a | 25 | BPh₃ | 0.11 | 190 | | |
| 259 | 11a | 80 | BPh₃ | 1.33 | 2,140 | MI: 160; $M_n$($^1$H): 7,990 | 40.5 |
| 260 | 12a | 25 | BPh₃ | 3.68 | 6,040 | MI < 0.01 | |
| 261 | 12a | 80 | BPh₃ | 4.22 | 7,260 | MI: 74; $M_n$($^1$H): 9,260 | 33.0 |
| 262 | 12a | 80 | B(C₆F₅)₃ | 1.61 | 2,870 | MI: 30; $M_n$($^1$H): 12,700 | 19.3 |
| 263 | 13a | 25 | BPh₃ | 0.99 | 1,690 | MI: 0.04; $M_n$($^1$H): 23,400 | 20.5 |
| 264 | 13a | 80 | BPh₃ | 3.73 | 6,580 | MI: 147; $M_n$($^1$H): 4,890 | 40.2 |
| 265 | 13a | 80 | B(C₆F₅)₃ | 0.93 | 1,560 | MI > 200; $M_n$($^1$H): 4,520 | 36.5 |
| 266 | 14a | 25 | BPh₃ | 1.68 | 3,120 | MI: 0.3; $M_n$($^1$H): 18,300 | 24.2 |
| 267 | 14a | 25 | B(C₆F₅)₃ | 4.28 | 7,010 | MI: 6; $M_n$($^1$H): 5,820 | 42.6 |
| 268 | 14a | 80 | B(C₆F₅)₃ | 1.52 | 2,760 | MI: 117; $M_n$($^1$H): 3,080 | 54.0 |
| 269 | 15a | 25 | BPh₃ | 0.265 | 468 | | |
| 270 | 15a | 25 | BPh₃ | 1.75 | 3,060 | MI: 0.1; $M_n$($^1$H): 1,900 | 30.7 |
| 271 | 15a | 80 | B(C₆F₅)₃ | 0.399 | 705 | $M_n$($^1$H): 1,700 | 43.7 |
| 272 | 17a | 25 | BPh₃ | 0.191 | 346 | $M_n$($^1$H): 23,500 | |
| 273 | 17a | 25 | B(C₆F₅)₃ | 5.69 | 10,100 | MI < 0.01; $M_n$($^1$H): 24,600 | 10.4 |
| 274 | 17a | 80 | B(C₆F₅)₃ | 1.59 | 2,540 | MI: 0.08; $M_n$($^1$H): 7,130 | 24.1 |
| 275 | 18a | 25 | BPh₃ | e | e | | |
| 276 | 18a | 80 | B(C₆F₅)₃ | 0.046 | 76 | $M_n$($^1$H): 4,690 | 27.4 |
| 277 | 19a | 25 | BPh₃ | 0.289 | 544 | $M_n$($^1$H): 4,450 | 36.2 |
| 278 | 19a | 25 | B(C₆F₅)₃ | 0.223 | 399 | $M_n$($^1$H): 1,660 | 27.8 |
| 279 | 19a | 80 | BPh₃ | 0.077 | 128 | $M_n$($^1$H): 2,550 | 39.3 |
| 280 | 19a | 80 | B(C₆F₅)₃ | 0.224 | 399 | $M_n$($^1$H): 839 | 52.5 |
| 281 | 21a | 25 | BPh₃ | 6.48 | 10,700 | MI: 42; $M_n$($^1$H): 21,400 | 24.9 |
| 282 | 21a | 80 | BPh₃ | 3.44 | 6,090 | MI > 200; $M_n$($^1$H): 4,010 | 52.5 |
| 283 | 21a | 80 | B(C₆F₅)₃ | 0.123 | 226 | | |
| 284 | 21b | 25 | BPh₃ | 4.15 | 6,060 | MI: 16.5; $M_n$($^1$H): 21,600 | 19.9 |
| 285 | 21b | 25 | B(C₆F₅)₃ | 0.024 | 31 | $M_n$($^1$H): 1,570 | 34.2 |
| 286 | 21b | 80 | BPh₃ | 3.39 | 5,640 | MI > 200; $M_n$($^1$H): 3,730 | 55.2 |
| 287 | 21b | 80 | B(C₆F₅)₃ | 0.030 | 48 | $M_n$($^1$H): 2,190 | 38.7 |
| 288 | 22a | 25 | BPh₃ | 10.1 | 17,900 | MI > 200; $M_n$($^1$H): 2,600 | 85.1 |
| 289 | 22a | 80 | BPh₃ | 4.11 | 7,120 | Mn($^1$H): 1,630 | 92.6 |
| 290 | 22a | 80 | B(C₆F₅)₃ | 0.15 | 260 | Mn($^1$H): no olefins | 23.7 |
| 291 | 23a | 25 | BPh₃ | 2.93 | 4,770 | MI > 200; $M_n$($^1$H): 7,220 | 59.1 |
| 292 | 23a | 25 | BPh₃ | 2.90 | 4,960 | MI: 120; $M_n$($^1$H): 8,950 | 56.5 |
| 293 | 23a | 80 | B(C₆F₅)₃ | e | e | | |
| 294 | 24a | 25 | BPh₃ | 1.73 | 3,250 | MI < 0.01; $M_n$($^1$H): no olefins | 8.6 |
| 295 | 24a | 80 | BPh₃ | 1.95 | 3,340 | MI: 29; $M_n$($^1$H): 8,110 | 28.6 |
| 296 | 24a | 80 | B(C₆F₅)₃ | 1.16 | 2,060 | MI: 70; $M_n$($^1$H): 8,540 | 23.0 |
| 297 | 25a | 25 | BPh₃ | 9.07 | 17,000 | MI: 1.4 | |
| 298 | 25a | 80 | BPh₃ | 3.64 | 6,450 | MI > 200; $M_n$($^1$H): 3,310 | 54.2 |
| 299 | 25a | 80 | B(C₆F₅)₃ | 0.025 | 47 | $M_n$($^1$H): 3,140 | 31.6 |
| 300 | 26a | 25 | BPh₃ | 7.89 | 13,700 | MI > 200; $M_n$($^1$H): 3,250 | 69.2 |
| 301 | 26a | 25 | BPh₃ | 11.7 | 17,900 | MI > 200; $M_n$($^1$H): 3,930 | 66.6 |

TABLE 10-continued

Ethylene Polymerizations at 6.9 MPa: Pressure Tube Loaded in the Drybox under $N_2$ Atmosphere (Trichlorobenzene (5 mL), 18 h)

| Ex. | Cmpd[f] | Temp (° C.) | Lewis Acid[a] | PE(g) | PE(TO)[b] | M.W.[c] (MI, GPC, and/or $^1$H NMR) | Total Me[d] |
|---|---|---|---|---|---|---|---|
| 302 | 26a | 80 | $B(C_6F_5)_3$ | e | e | | |
| 303 | 27a | 25 | $BPh_3$ | 4.47 | 7,800 | MI: 210; $M_n(^1H)$: 8,040 | 52.7 |
| 304 | 27a | 25 | $BPh_3$ | 7.03 | 11,500 | MI: 108; $M_n(^1H)$: 8,230 | 50.9 |
| 305 | 27a | 80 | $B(C_6F_5)_3$ | 0.009 | 17 | $M_n(^1H)$: 5,070 | 27.9 |
| 306 | 28a | 25 | $BPh_3$ | 0.761 | 1,300 | MI: 60; $M_n(^1H)$: 19,900 | 37.1 |
| 307 | 28a | 25 | $BPh_3$ | 0.271 | 481 | $M_n(^1H)$: 26,700 | 31.3 |
| 308 | 28a | 80 | $B(C_6F_5)_3$ | 0.006 | 10 | $M_n(^1H)$: 6,630 | 19.8 |
| 309 | 29a | 25 | $B(C_6F_5)_3$ | 0.573 | 994 | MI: 0.12; $M_n(^1H)$: 4,010 | 16.2 |
| 310 | 29a | 25 | $BPh_3$ | e | e | | |
| 311 | 29a | 80 | $B(C_6F_5)_3$ | 0.199 | 360 | $M_n(^1H)$: 1,650 | 35.3 |
| 312 | 30a | 25 | $B(C_6F_5)_3$ | 2.45 | 4,160 | MI < 0.01; $M_n(^1H)$: 8,300 | 8.1 |
| 313 | 30a | 25 | $BPh_3$ | e | e | | |
| 314 | 30a | 80 | $B(C_6F_5)_3$ | 1.64 | 2,610 | MI: 17; $M_n(^1H)$: 3,600 | 23.0 |
| 315 | 33a | 25 | $BPh_3$ | 0.431 | 768 | $M_n(^1H)$: 21,300 | 3.4 |
| 316 | 33a | 25 | $B(C_6F_5)_3$ | 2.35 | 4,070 | MI: 0.13; $M_n(^1H)$: 4,270 | 37.1 |
| 317 | 33a | 80 | $B(C_6F_5)_3$ | 0.915 | 1,540 | MI: 36.8; $M_n(^1H)$: 1,860 | 36.1 |
| 318 | 34a | 25 | $B(C_6F_5)_3$ | 7.53 | 11,600 | $Mn(^1H)$: 3,450 | 72.4 |
| 319 | 34a | 80 | $B(C_6F_5)_3$ | 5.35 | 7,570 | $M_w$(GPC): 29,100; PDI: 46 | 113.2 |
| 320 | 36a | 25 | $BPh_3$ | 9.31 | 15,300 | $M_n$(GPC): 461,000; PDI: 3.3 | 8.0 |
| 321 | 36a | 80 | $BPh_3$ | 0.353 | 564 | $M_n$(GPC): 30,000; PDI: 4.0 | 25.8 |
| 322 | 37a | 25 | $BPh_3$ | 0.919 | 1,650 | MI: 0.06; $M_n(^1H)$: no olefins | 14.4 |
| 323 | 37a | 25 | $BPh_3$ | 0.299 | 434 | $M_n(^1H)$: 31,100 | 15.0 |
| 324 | 37a | 80 | $B(C_6F_5)_3$ | 0.269 | 434 | $M_n(^1H)$: 5,200 | 40.4 |
| 325 | 38a | 25 | $BPh_3$ | 1.43 | 2,470 | MI: 111; $M_n(^1H)$: 6,150 | 65.8 |
| 326 | 38a | 80 | $BPh_3$ | 1.55 | 2,580 | MI > 200; $M_n(^1H)$: 2,780 | 99.2 |
| 327 | 39a | 25 | $B(C_6F_5)_3$ | 0.414 | 814 | $M_n(^1H)$: 10,700 | 7.7 |
| 328 | 39a | 25 | $BPh_3$ | e | e | | |
| 329 | 39a | 25 | $BPh_3$ | e | e | | |
| 330 | 39a | 80 | $B(C_6F_5)_3$ | 0.758 | 1,290 | MI: 80; $M_n(^1H)$: 5,190 | 20.1 |
| 331 | 41a | 25 | $BPh_3$ | 0.316 | 586 | $M_n(^1H)$: no olefins | 11.5 |
| 332 | 41a | 25 | $B(C_6F_5)_3$ | 4.08 | 6,690 | MI < 0.01; $Mn(^1H)$: 30,700 | 30.9 |
| 333 | 41a | 80 | $B(C_6F_5)_3$ | 2.26 | 3,730 | MI: 180; $M_n(^1H)$: 9,960 | 36.9 |
| 334 | 43a | 25 | $BPh_3$ | e | e | | |
| 335 | 43a | 25 | $BPh_3$ | 0.53 | 918 | $M_n(^1H)$: 3,600 | 36.6 |
| 336 | 43a | 80 | $BPh_3$ | e | e | | |
| 337 | 43a | 80 | $B(C_6F_5)_3$ | 0.054 | 93 | $M_n(^1H)$: 2,960 | 32.0 |
| 338 | 44a | 25 | $B(C_6F_5)_3$ | 0.167 | 291 | $M_n$(GPC): 136,000; PDI: 18 | 25.4 |
| 339 | 44a | 80 | $B(C_6F_5)_3$ | 0.019 | 34 | $Mn(^1H)$: 5,150 | 43.3 |
| 340 | 45a | 25 | $B(C_6F_5)_3$ | 0.026 | 43 | $M_n(^1H)$: 5,150 | 8.6 |
| 341 | 45a | 80 | $B(C_6F_5)_3$ | trace | trace | $M_n(^1H)$: 6,310 | 14.2 |

[a]Two equiv.
[b]TO: number of turnovers per metal center = (moles ethylene consumed, as determined by the weight of the isolated polymer or oligomers) divided by (moles catalyst). Calculations are based upon the exact amount of catalyst used.
[c]M.W.: Molecular weight of the polymer or oligomers as determined by melt index (MI: g/10 min at 190° C.), GPC (molecular weights are reported versus polystyrene standards; conditions: Waters 150C, trichlorobenzene at 150° C., Shodex columns at −806MS 4G 734/602005, RI detector), and/or $^1$H NMR (olefin end group analysis).
[d]Total number of methyl groups per 1000 methylene groups as determined by $^1$H NMR analysis.
[e]PE was not obtained in isolable quantities.
[f]0.02 mmol unless noted otherwise.
[g]0.015 mmol.
[h]0.06 mmol.
[i]0.04 mmol.

TABLE 11

Ethylene Polymerizations at 6.9 MPa Pressure Tube Loaded in the Drybox under $N_2$ Atmosphere (p-Xylene, (5 mL), 18 h)

| Ex. | Cmpd[f] | Temp (° C.) | Lewis Acid[a] | PE(g) | PE(TO)[b] | M.W.[c] (MI, GPC, and/or $^1$H NMR) | Total Me[d] |
|---|---|---|---|---|---|---|---|
| 342 | 3a[h] | 25 | $BPh_3$ | 20.2 | 12,000 | MI: 2.6 | |
| 343 | 3a[g] | 25 | $BPh_3$ | 0.19 | 366 | | |
| 344 | 3a[g] | 25 | $B(C_6F_5)_3$ | 0.48 | 1,160 | $M_n(^1H)$: 27,100 | 24.4 |
| 345 | 6a[h] | 80 | $BPh_3$ | 11.1 | 6,610 | MI: 105; $M_n(^1H)$: 9,090 | 31.1 |

TABLE 11-continued

Ethylene Polymerizations at 6.9 MPa Pressure Tube Loaded in the Drybox under $N_2$ Atmosphere (p-Xylene, (5 mL), 18 h)

| Ex. | Cmpd[f] | Temp (° C.) | Lewis Acid[a] | PE(g) | PE(TO)[b] | M.W.[c] (MI, GPC, and/or $^1$H NMR) | Total Me[d] |
|---|---|---|---|---|---|---|---|
| 346 | 6a[h] | 80 | $B(C_6F_5)_3$ | 6.90 | 4,100 | MI: > 200; $M_n(^1H)$: 3,170 | 63.4 |
| 347 | 6a[g] | 80 | $B(C_6F_5)_3$ | 3.47 | 8,470 | MI: 58.8; $M_n(^1H)$: 6,880 | 34.5 |

[a]Two equiv.
[b]TO: number of turnovers per metal center = (moles ethylene consumed, as determined by the weight of the isolated polymer or oligomers) divided by (moles catalyst). Calculations are based upon the exact amount of catalyst used.
[c]M.W.: Molecular weight of the polymer or oligomers as determined by melt index (MI: g/10 min at 190° C.), GPC (molecular weights are reported versus polystyrene standards; conditions: Waters 150C, trichlorobenzene at 150° C., Shodex columns at −806MS 4G 734/602005, RI detector), and/or $^1$H NMR (olefin group analysis).
[d]Total number of methyl groups per 1000 methylene groups as determined by $^1$H NMR analysis.
[e]PE was not obtained in isolable quantities.
[f]0.02 mmol unless noted otherwise.
[g]0.015 mmol.
[h]0.06 mmol.

TABLE 12

Ethylene Polymerizations at 6.9 MPa Pressure Tube Loaded in the Drybox under $N_2$ Atmosphere (Cyclohexane, (5 mL), 18 h)

| Ex. | Cmpd[f] | Temp (° C.) | Lewis Acid[a] | PE(g) | PE(TO)[b] | M.W.[c] (MI, GPC, and/or $^1$H NMR) | Total Me[d] |
|---|---|---|---|---|---|---|---|
| 348 | 3a[g] | 25 | $BPh_3$ | 0.52 | 1,160 | | |
| 349 | 6a[h] | 80 | $BPh_3$ | 10.6 | 6,270 | MI: 135; $M_n(^1H)$: 7,410 | 33.8 |
| 350 | 6a[g] | 80 | $BPh_3$ | 7.07 | 16,810 | MI: 129; $M_n(^1H)$: 8,800 | 27.7 |

[a]Two equiv.
[b]TO: number of turnovers per metal center = (moles ethylene consumed, as determined by the weight of the isolated polymer or oligomers) divided by (moles catalyst). Calculations are based upon the exact amount of catalyst used.
[c]M.W.: Molecular weight of the polymer or oligomers as determined by melt index (MI: g/10 min at 190° C.), GPC (molecular weights are reported versus polystyrene standards; conditions: Waters 150C, trichlorobenzene at 150° C., Shodex columns at −806MS 4G 734/602005, RI detector), and/or $^1$H NMR (olefin end group analysis).
[d]Total number of methyl groups per 1000 methylene groups as determined by $^1$H NMR analysis.
[e]PE was not obtained in isolable quantities.
[f]0.02 mmol unless noted otherwise.
[g]0.015 mmol.
[h]0.06 mmol.

TABLE 13

Ethylene Polymerizations at 1.4 MPa Pressure Tube Loaded in the Drybox under $N_2$ Atmosphere (Trichlorobenzene (5 mL) 0.02 mmol Cmpd, 18 h)

| Ex. | Cmpd | Temp (° C.) | Lewis Acid[a] | PE(g) | PE(TO)[b] | M.W.[c] (MI, GPC, and/or $^1$H NMR) | Total Me[d] |
|---|---|---|---|---|---|---|---|
| 351 | 3a | 25 | $BPh_3$ | 1.71 | 2,540 | MI: 0.26; $M_n(^1H)$: 64,600 | 17.3 |
| 352 | 4a | 25 | $BPh_3$ | 2.87 | 5,000 | MI: 92; $M_n(^1H)$: 15,300 | 40.3 |
| 353 | 6a | 25 | $B(C_6F_5)_3$ | 2.31 | 3,760 | MI: 1; $M_n(^1H)$: 11,700 | 55.0 |
| 354 | 8a | 25 | $B(C_6F_5)_3$ | 2.10 | 3,440 | MI: 123; $M_n(^1H)$: 5,570 | 81.5 |
| 355 | 9a | 25 | $B(C_6F_5)_3$ | 1.53 | 2,730 | $M_n(^1H)$: 4,850 | 112.3 |
| 356 | 14a | 25 | $B(C_6F_5)_3$ | 1.18 | 2,080 | MI: 7.5; $M_n(^1H)$: 4,730 | 53.3 |
| 357 | 21a | 25 | $BPh_3$ | 1.58 | 2,670 | MI: 1.5; $M_n(^1H)$: 14,700 | 39.9 |
| 358 | 22a | 25 | $BPh_3$ | 2.94 | 4740 | MI > 200; $M_n(^1H)$: 4,580 | 73.7 |

TABLE 13-continued

Ethylene Polymerizations at 1.4 MPa
Pressure Tube Loaded in the Drybox under $N_2$ Atmosphere
(Trichlorobenzene (5 mL) 0.02 mmol Cmpd, 18 h)

| Ex. | Cmpd | Temp (° C.) | Lewis Acid[a] | PE(g) | PE(TO)[b] | M.W.[c] (MI, GPC, and/or $^1$H NMR) | Total Me[d] |
|---|---|---|---|---|---|---|---|
| 359 | 25a | 25 | BPh$_3$ | 1.18 | 2,060 | MI: 6.6; $M_n$($^1$H): 5,020 | 110.6 |
| 360 | 26a | 25 | BPh$_3$ | 2.41 | 4,040 | MI > 200; $M_n$($^1$H): 3,870 | 73.6 |

[a]Two equiv.
[b]TO: number of turnovers per metal center = (moles ethylene consumed, as determined by the weight of the isolated polymer or oligomers) divided by (moles catalyst). Calculations are based upon the exact amount of catalyst used.
[c]M.W.: Molecular weight of the polymer or oligomers as determined by melt index (MI: g/10 min at 190° C.), GPC (molecular weights are reported versus polystyrene standards; conditions: Waters 150C, trichlorobenzene at 150° C., Shodex columns at −806MS 4G 734/602005, RI detector), and/or $^1$H NMR (olefin end group analysis).
[d]Total number of methyl groups per 1000 methylene groups as determined $^1$H NMR analysis.
[e]PE was not obtained in isolable quantities.

TABLE 14

Ethylene Polymerizations Using Nickel Methyl Initiators:
Effect of Lewis Acid on Initiation/Productivity
(6.9 MPa, 0.02 mmol Cmpd. Trichlorobenzene (5 mL), 18 h)

| Ex. | Cmpd | Temp (° C.) | Lewis Acid (equiv) | PE(g) | PE(TO)[a] | M.W.[b] (MI, GPC, and/or $^1$H NMR) | Total Me[c] |
|---|---|---|---|---|---|---|---|
| 361 | 50[d] | 25 | none | trace | trace | | |
| 362 | 50[d] | 80 | none | 0.189 | 307 | $M_n$($^1$H): 5,840 | 39.4 |
| 363 | 50 | 25 | BPh$_3$ (2) | 0.126 | 201 | | |
| 364 | 50 | 80 | B(C$_6$F$_5$)$_3$ (2) | 0.074 | 124 | | |
| 365 | 50 | 25 | BPh$_3$ (10) | 4.41 | 7,590 | | |
| 366 | 50 | 80 | BPh$_3$ (10) | 3.01 | 5,220 | $M_w$(GPC): 17,900; PDI: 6 | |

[a]TO: number of turnovers per metal center = (moles ethylene consumed, as determined by the weight of the isolated polymer or oligomers) divided by (moles catalyst). Calculations are based upon the exact amount of catalyst used.
[b]M.W.: Molecular weight of the polymer or oligomers as determined by melt index (MI: g/10 min at 190° C.), GPC (molecular weights are reported versus polystyrene standards; conditions: Waters 150C, trichlorobenzene at 150° C., Shodex columns at −806MS 4G 734/602005, RI detector), and/or $^1$H NMR (olefin end group analysis).
[c]Total number of methyl groups per 1000 methylene groups as determined by $^1$H NMR analysis.
[d]Under the same reaction conditions (e.g., no Lewis acid present), nickel compounds 51–54 gave analogous results: no polymer was isolated, but the $^1$H NMR spectra showed a —(CH$_2$)$_n$— resonance.

EXAMPLES 367–369

Cyclopentene Oligomerizations

General Procedure for Cyclopentene Oligomerizations. In the drybox under a nitrogen atmosphere, the nickel compound (0.03 mmol) was placed in a vial. Next, 5 mL of toluene was added to the vial followed by 1.3 mL of cyclopentene. B(C$_6$F$_5$)$_3$ (40 mg) was then added to the vial. The reaction mixture was mixed for 3 d on a vortexer and then removed from the drybox and added to 100 mL of stirring methanol. No polymer precipitated. GC analysis was carried out on the organic layer. The results are reported in Table 15 below.

TABLE 15

Cyclopentene Oligomerizations

| Ex. | Cmpd | GC Analysis |
|---|---|---|
| 367 | 31a | dimers through heptamers observed |
| 368 | 32a | dimers through heptamers observed |
| 369 | 47b | dimers through heptamers observed |

EXAMPLES 370–375

Ethylene/Ethyl 4-Pentenoate Polymerizations

General Procedure for Ethylene/Ethyl 4-Pentenoate Polymerizations. In a nitrogen-filled drybox, the nickel compound (0.06 mmol) and the Lewis acid (5 equiv) were placed together in a glass insert. The insert was cooled to −30° C. in the drybox freezer. 5 mL of cold ethyl 4-pentenoate was added to the cold insert, and the insert was recooled in the drybox freezer. The cold inserts were removed from the drybox and placed under a nitrogen purge in a pressure tube, which was then sealed and pressurized to 6.9 MPa of ethylene and mechanically shaken for 18 h. The pressure was then released and the glass insert was removed from the pressure tube and the polymer was precipitated in MeOH, collected on a frit, and dried in vacuo. Characteristic NMR resonances of the copolymer include the 4.01 OCH$_2$ resonance in the $^1$H NMR and the 59.7 OCH$_2$ resonance and ~172.4 C=O resonances in the $^{13}$C NMR spectrum.

TABLE 16

Ethylene/Ethyl 4-Pentenoate (E-4-P) Polymerizations

| Ex. | Cmpd | Lewis Acid | Temp (° C.) | Polymer (g) | DSC/GPC |
|---|---|---|---|---|---|
| 370 | 3a | BPh$_3$ | 25 | 2.35 | DSC: T$_m$ = 111° C. |
| | | | | | $^{13}$C NMR: 0.59 mole percent E-4-P Incorp.; Branching per 1000 CH$_2$'s: Total methyls (27.3), Methyl (23.7), Ethyl (1.7), Propyl (0), Butyl (0.8), Amyl (2.4), Hex and greater and end of chains (5.4), Am and greater and end of chains (1.9), Bu and greater and end of chains (1.8) |
| 371 | 21a | BPh$_3$ | 25 | 0.586 | DSC: T$_m$ = 115° C. |
| | | | | | $^{13}$C NMR: 0.26 mole percent E-4-P Incorp.; Branching per 1000 CH$_2$'s: Total methyls (25.0), Methyl (19.3), Ethyl (2.1), Propyl (0.0), Butyl (1.2), Amyl (0.3), Hex and greater and end of chains (3.1), Am and greater and end of chains (4.1), Bu and greater and end of chains 3.6) |
| 372 | 8a | B(C$_6$F$_5$)$_3$ | 25 | 0.254 | DSC: T$_m$ = 124° C., 96° C. |
| | | | | | $^{13}$C NMR: 0.64 mole percent E-4-P Incorp.; Branching per 1000 CH$_2$'s: Total methyls (47.8), Methyl (35.8), Ethyl (3.7), Propyl (0.0), Butyl (3.1), Amyl (3.8), Hex and greater and end of chains (8.7), Am and greater and end of chains (10.2), Bu and greater and end of chains (8.3) |
| 373 | 3a | BPh$_3$ | 80 | 0.468 | |
| | | | | | $^{13}$C NMR: 1.94 mole percent E-4-P Incorp.; Branching per 1000 CH$_2$'s: Total methyls (67.0), Methyl (50.7), Ethyl (6.3), Propyl (0.0), Butyl (3.7), Amyl (7.3), Hex and greater and end of chains (18.6), Am and greater and end of chains (8.4), Bu and greater and end of chains (9.9) |
| 374 | 21a | BPh$_3$ | 80 | 0.312 | |
| | | | | | $^{13}$C NMR: 1.67 mole percent E-4-P Incorp.; Branching per 1000 CH$_2$'s: Total methyls (73.9), Methyl (47.9), Ethyl (9.2), Propyl (0.0), Butyl (0.0), Amyl (6.1), Hex and greater and end of chains (16.2), Am and greater and end of chains (15.7), Bu and greater and end of chains (16.8) |
| 375 | 8a | B(C$_6$F$_5$)$_3$ | 80 | 0.232 | GPC (THF, 35° C.): M$_w$ = 5,130, PDI = 1.7; DSC: T$_m$: 117° C., 46° C. |
| | | | | | $^1$H NMR: 1.6 mole percent E-4-P Incorp.; Branching per 1000 CH$_2$'s: Total methyls (94) |

EXAMPLES 376–381

General Procedure for Ethylene Polymerizations of Table 17

Ethylene Polymerizations in the Parr® Reactor

Procedure. Prior to conducting the polymerization, the Parr® reactor flushed with nitrogen, heated under vacuum overnight, and then allowed to cool to room temperature. In the drybox, a glass vial was loaded with the nickel compound, Lewis acid and solvent and then capped with a rubber septum. The solution of the nickel complex and Lewis acid was then transferred to a 100 mL Parr reactor under vacuum, and the reactor was pressurized with ethylene and the reaction mixture was mechanically stirred. After the stated reaction time, the ethylene pressure was released, and the polymer was precipitated by adding the reaction mixture to a solution of MeOH (~100 mL) and concentrated HCl (~1–3 mL). The polymer was then collected on a frit and rinsed with HCl, MeOH, and acetone. The polymer was transferred to a pre-weighed vial and dried under vacuum overnight. The polymer yield and characterization were then obtained.

TABLE 17

Ethylene Polymerizations in the Parr Reactor
(0.02 mmol Cmpd, Trichlorobenzene (35 mL))

| Ex. | Cmpd | Time (h) | Press. (MPa) | Lewis Acid (equiv) | PE(g) | PE(TO)[a] | M.W.[b] (MI, GPC, and/or $^1$H NMR) | Total Me[c] |
|---|---|---|---|---|---|---|---|---|
| 376 | 6a | 9.9 | 5.5 | B(C$_6$F$_5$)$_3$/2 | 7.46 | 12,400 | M$_n$($^1$H):no olefins | 34.4 |
| 377 | 6a | 0.5 | 5.5 | B(C$_6$F$_5$)$_3$/2 | 3.5 | 5,940 | M$_n$($^1$H):no olefins | 40.3 |
| 378 | 6a | 6.5 | 5.5 | B(C$_6$F$_5$)$_3$/2 | 9.30 | 15,500 | M$_n$($^1$H):no olefins | 39.2 |
| 379 | 6a | 4.8 | 1.4 | B(C$_6$F$_5$)$_3$/2 | 0.26 | 394 | M$_n$($^1$H):no olefins | 32.6 |
| 380 | 3a | 6.0 | 3.5 | BPh$_3$/5 | 3.57 | 5,560 | M$_n$($^1$H):no olefins | 19.1 |
| 381 | 6a | 6.6 | 3.5 | B(C$_6$F$_5$)$_3$/5 | 1.52 | 2,480 | M$_n$($^1$H):no olefins | 29.0 |

[a]TO: number of turnovers per metal center = (moles ethylene consumed, as determined by the weight of the isolated polymer or oligomers) divided by (moles catalyst). Calculations are based upon the exact amount of catalyst used.
[b]M.W.: Molecular weight of the polymer or oligomers as determined by melt index (MI: g/10 min at 190° C.), GPC (molecular weights are reported versus polystyrene standards; conditions: Waters 150C, trichlorobenzene at 150° C., Shodex columns at –806MS 4G 734/602005, RI detector), and/or $^1$H NMR (olefin end group analysis).
[c]Total number of methyl groups per 1000 methylene groups as determined by $^1$H NMR analysis.
[d]Under the same reaction conditions (e.g., no Lewis acid present), nickel compounds 51–54 gave analogous results: no polymer was isolated, but the $^1$H NMR spectra showed a —(CH$_2$)$_n$— resonance.

EXAMPLES 382–437

General Procedure for Ethylene (28–35 kPa) Polymerizations of Table 18

Procedure. In the drybox, a glass Schlenk flask was loaded with the nickel compound, Lewis acid, solvent and a stir bar. The flask was then capped with a rubber septum and the stopcock was closed prior to removing the flask from the drybox. The flask was then attached to the ethylene line where it was evacuated and backfilled with ethylene. The reaction mixture was stirred under ethylene for the stated reaction time, the ethylene pressure was then released, and the polymer was precipitated by adding the reaction mixture to a solution of MeOH (~100 mL) and concentrated HCl (~1–3 mL). The polymer was then collected on a frit and rinsed with MeOH. The polymer was transferred to a pre-weighed vial and dried under vacuum overnight. The polymer yield and characterization were then obtained.

TABLE 18

Ethylene Polymerizations at 28–35 kPa Ethylene

| Ex. | Cmpd | Lewis Acid (equiv) | Time (h) | Solvent (mL)[b] | PE(g) | PE(TO) |
|---|---|---|---|---|---|---|
| 382 | 1a | $B(C_6F_5)_3$/20 | 25.0 | Toluene (35) | [a] | [a] |
| 383 | 1a | MAO-IP/90 | 0.5 | Toluene (35) | 0.924 | 1,040 |
| | | Description: White rubbery solid. | | | | |
| 384 | 2a | MAO-IP/86 | 0.5 | Toluene (35) | 0.534 | 577 |
| | | Description: White, soft, slightly rubbery solid. | | | | |
| 385 | 3a | $BPh_3$/5 | 26.3 | Toluene (35) | [a] | [a] |
| 386 | 3a | $BPh_3$/20 | 23.5 | Toluene (35) | 0.662 | 787 |
| | | Description: Slightly sticky, clear, colorless amorphous solid. $^1H$ NMR ($C_6D_6$, rt) 99.6 total Me/1000 $CH_2$ | | | | |
| 387 | 3a | $BPh_3$/50 | 23.5 | Toluene (35) | 0.110 | 131 |
| | | Description: Clear, colorless sticky viscous oil. $^1H$ NMR ($C_6D_6$, rt) 98.6 total Me/1000 $CH_2$ | | | | |
| 388 | 3a | $BPh_3$/100 | 23.5 | Toluene (35) | 0.021 | 25 |
| | | Description: Light yellow, clear amorphous solid/oil. $^1H$ NMR ($C_6D_6$, rt) 102.7 total Me/1000 $CH_2$ | | | | |
| 389 | 3a | $B(C_6F_5)_3$/20 | 32.4 | Toluene (35) | 0.042 | 50 |
| | | Description: White powder. | | | | |
| 390 | 3a | $BF_3 \cdot Et_2O$/50 | 25.5 | Toluene (35) | [a] | [a] |
| 391 | 4a | $BPh_3$/50 | 23.5 | Toluene (35) | 0.261 | 310 |
| | | Description: Clear, amorphous gummy solid. $^1H$ NMR ($C_6D_6$, rt) 107.4 total Me/1000 $CH_2$ | | | | |
| 392 | 4a | $BPh_3$/100 | 37.2 | Toluene (35) | 0.797 | 950 |
| | | Description: Soft, white powder/solid. | | | | |
| 393 | 5a | $BPh_3$/5 | 26.3 | Toluene (35) | [a] | [a] |
| 394 | 5a | $BPh_3$/50 | 23.5 | Toluene (35) | 0.054 | 64 |
| | | Description: White slightly sticky, partially amorphous solid. | | | | |
| 395 | 5a | $BPh_3$/50 | 26.4 | Toluene (35) | 0.065 | 77 |
| | | Description: Clear/white partial powder/partial amorphous solid. | | | | |
| 396 | 6a | $B(C_6F_5)_3$/5 | 26.4 | Toluene (35) | 0.15 | 180 |
| | | Description: Brown sticky amorphous solid. $^1H$ NMR ($C_6D_6$, rt): 105.4 Total Me/1000 $CH_2$ | | | | |
| 397 | 6a | $B(C_6F_5)_3$/20 | 26.4 | Toluene (35) | 7.38 | 8,760 |
| | | Description: White, slightly rubbery or spongy powder. $^{13}C$ NMR: Branching per 1000 $CH_2$'s. Total methyls (59.8), methyl (38.5), ethyl (10.4), propyl (1.6), butyl (2.4), hexyl and greater and end of chains (7.0), amy and greater and end of chains (7.9), butyl and greater and end of chains (9.3). | | | | |
| 398 | 6a | $BPh_3$/100 | 17.0 | Toluene (35) | 0.17 | 200 |
| | | Description: White soft powder. | | | | |
| 399 | 6a | $BF_3 \cdot Et_2O$/50 | 25.5 | Toluene (35) | [a] | [a] |
| 400 | 6a | $Al(O-i-Pr)_3$/20 | 22.4 | Toluene (35) | [a] | [a] |
| 401 | 6a | PMAO-IP/28 | 25.1 | Toluene (35) | [a] | [a] |
| 402 | 7a | $B(C_6F_5)_3$/20 | 24.1 | Toluene (35) | 1.04 | 1,180 |
| | | Description: White powder. | | | | |
| 403 | 8a | $B(C_6F_5)_3$/5 | 25.4 | Toluene (35) | 1.45 | 1,730 |
| | | Soft partial powder/partial amorphous solid. $^1H$ NMR ($C_6D_6$, rt): 118.3 Total Me/1000 $CH_2$ | | | | |
| 404 | 8a | $BPh_3$/100 | 17.0 | Toluene (35) | 0.016 | 19 |
| | | Description: Tan powder. | | | | |
| 405 | 8a | $B(C_6F_5)_3$/20 | 23.1 | Toluene (35) | 2.82 | 3,350 |
| | | Description: Brown amorphous sticky solid. $^1H$ NMR ($C_6D_6$, rt): 143.0 Total Me/1000 $CH_2$ | | | | |
| 406 | 9a | $B(C_6F_5)_3$/5 | 26.4 | Toluene (35) | 0.018 | 21 |
| | | Description: Brown partial oil, partial amorphous solid. | | | | |
| 407 | 9a | $B(C_6F_5)_3$/20 | 23.1 | Toluene (35) | 6.99 | 8,300 |
| | | Description: Brown amorphous sticky solid. $^1H$ NMR ($C_6D_6$, rt): 174.4 Totalt Me/1000 $CH_2$ | | | | |
| 408 | 10a | $BPh_3$/20 | 24.2 | Toluene (35) | 1.43 | 1,700 |
| | | Description: White powder. | | | | |
| 409 | 12a | $BPh_3$/20 | 25.0 | Toluene (35) | 0.749 | 890 |
| | | Description: White powder. | | | | |
| 410 | 12a | $B(C_6F_5)_3$/10 | 22.5 | Toluene (35) | [a] | [a] |
| 411 | 14a | $B(C_6F_5)_3$/20 | 25.5 | Toluene (35) | 0.97 | 1,150 |
| | | Description: White, stringy powder | | | | |
| 412 | 15a | $B(C_6F_5)_3$/10 | 22.5 | Toluene (35) | 0.106 | 126 |
| | | Description: Slightly rubbery off-white solid. | | | | |
| 413 | 17a | $B(C_6F_5)_3$/20 | 25.5 | Toluene (35) | 2.08 | 2,470 |
| | | Description: Soft white powder. | | | | |
| 414 | 21a | $BPh_3$/5 | 25.4 | Toluene (35) | 1.88 | 2,230 |
| | | Description: White, somewhat rubbery powder. | | | | |
| 415 | 21a | $BPh_3$/20 | 26.4 | Toluene (35) | 1.73 | 2,060 |
| | | Description: White powder. | | | | |
| 416 | 21a | $BPh_3$/50 | 26.4 | Toluene (35) | 0.631 | 750 |
| | | Description: White powder. | | | | |
| 417 | 21a | $BPh_3$/100 | 21.4 | 1,2,4-TCB (20) | 0.474 | 563 |
| | | Description: White powder. | | | | |
| 418 | 21b | $BPh_3$/100 | 21.4 | 1,2,4-TCB(20) | 0.156 | 185 |
| 419 | 22a | $BPh_3$/100 | 37.2 | Toluene (35) | 0.777 | 920 |
| | | Description: White powder. | | | | |
| 420 | 23a | $BPh_3$/20 | 26.0 | Toluene (35) | 0.409 | 473 |
| | | Description: Almost clear, sticky amorphous oil/solid. | | | | |
| 421 | 24a | $B(C_6F_5)_3$/10 | 22.5 | Toluene (35) | [a] | [a] |
| 422 | 24a | $BPh_3$/50 | 22.4 | Toluene (35) | 0.374 | 444 |
| | | Description: White powder. | | | | |
| 423 | 25a | $BPh_3$/50 | 24.2 | Toluene (35) | 1.47 | 1,750 |
| | | Description: White, slightly rubbery powder. | | | | |
| 424 | 27a | $BPh_3$/20 | 26.0 | Toluene (35) | 0.856 | 992 |
| | | Description: Amorphous, slightly sticky, waxy, clear solid. $^1H$ NMR ($C_6D_6$, rt) 90.0 total Me/1000 $CH_2$ | | | | |
| 425 | 30a | $B(C_6F_5)_3$/20 | 24.2 | Toluene (25) | 0.65 | 770 |
| | | Description: White powder. | | | | |
| 426 | 34a | $B(C_6F_5)_3$/20 | 23.1 | Toluene (35) | 5.75 | 6,830 |
| | | Description: Tan amorphous solid. $^1H$ NMR ($C_6D_6$, rt) 182.0 Total Me/1000 $CH_2$. Mn~1,980 | | | | |
| 427 | 36a | $BPh_3$/20 | 25.6 | Toluene (35) | 1.32 | 1,570 |
| | | Description: White powder. | | | | |
| 428 | 36a | $B(C_6F_5)_3$/10 | 24.3 | Toluene (35) | 0.11 | 130 |
| | | Description: Tan powder. | | | | |
| 429 | 37a | $BPh_3$/20 | 23.8 | Toluene (35) | 0.486 | 576 |
| 430 | 38a | $BPh_3$/20 | 26.0 | Toluene (35) | 0.024 | 28 |
| | | Description: Clear, amorphous, very slightly sticky solid $^1H$ NMR ($C_6D_6$, rt) 91.2 total Me/1000 $CH_2$ | | | | |
| 431 | 39a | $B(C_6F_5)_3$/20 | 22.6 | Toluene (20) | 0.244 | 290 |
| | | Description: White powder. | | | | |
| 432 | 39a | $BPh_3$/200 | 23.8 | Toluene (35) | [a] | [a] |
| 433 | 41a | $B(C_6F_5)_3$/5 | 25.4 | Toluene (35) | 0.059 | 70 |
| | | Description: White powder. | | | | |
| 434 | 41a | $B(C_6F_5)_3$/20 | 22.4 | Toluene (35) | 1.73 | 2,060 |
| | | Description: White powder. | | | | |
| 435 | 50 | $BPh_3$/100 | 21.4 | 1,2,4-TCB (20) | 1.06 | 1,260 |
| | | Description: White powder. | | | | |
| 436 | 52 | $BPh_3$/100 | 21.4 | 1,2,4-TCB(20) | 1.21 | 1,440 |
| | | Description: White powder. | | | | |
| 437 | 52 | $BPh_3$/100 | 23.1 | Toluene (35) | 1.40 | 1,660 |
| | | Description: White powder. | | | | |

[a]Only a trace of polymer or no polymer was isolated.
[b]1,2,4-Trichlorobenzene is abbreviated as 1,2,4-TCB.

EXAMPLE 438

Ethylene Polymerization Using (acac)Ni(Et)PPh$_3$ Precursor at 6.9 MPa

In the drybox, a glass insert was loaded with (acac)Ni(Et)PPh$_3$ (26.9 mg, 0.06 mmol) and [2-(NaO)-3,5-(t-Bu)$_2$—C$_6$H$_2$—C(Me)=NAr (Ar=2,6-(i-Pr)$_2$—C$_6$H$_3$) 0.5 THF] (25.8 mg, 1 equiv). The insert was cooled to −35° C. in the drybox freezer, 5 mL of C$_6$D$_6$ was added to the cold insert, and the insert was cooled again. BPh$_3$ (29.1 mg, 2 equiv) was added to the cold solution, and the insert was then capped and sealed and cooled again. Outside of the drybox, the cold insert was placed under a nitrogen purge into the pressure tube. The pressure tube was sealed, placed under ethylene (6.9 MPa), and allowed to warm to rt as it was shaken mechanically for approximately 18 h. Polyethylene (16.5 g, 9,820 TO) was isolated as a powder following precipitation from methanol.

EXAMPLE 439

Ethylene Polymerization Using NiBr$_2$ Precursor at 28–35 MPa

The sodium salt of the ligand of Example 1 (1.01 g, 2.23 mmol), e.g.

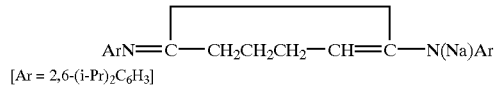
[Ar = 2,6-(i-Pr)$_2$C$_6$H$_3$]

was placed in a round bottom flask in the drybox together with 487 mg (2.23 mmol) of NiBr$_2$. THF (20 mL) was added and the solution was stirred for ~2 months. The THF was removed in vacuo and the product was dissolved in CH$_2$Cl$_2$ and the resulting solution was filtered. The solvent was removed and the product was dried in vacuo. An orange powder (488 mg) was isolated. (In addition to CD$_2$Cl$_2$, the product was also soluble in C$_6$D$_6$. $^1$H NMR spectra in both solvents were complex.)

In the drybox, a glass Schlenk flask was loaded with the resulting orange nickel compound (17 mg, ~0.03 mmol), 35 mL of toluene and a stir bar. The flask was then capped with a rubber septum and the stopcock was closed prior to removing the flask from the drybox. The flask was then attached to the ethylene line where it was evacuated and backfilled with ethylene. MAO-IP (2 mL, ~94 equiv) was added to the flask via cannula. The reaction mixture was stirred under ethylene for 3.5 h, the ethylene pressure was then released, and the polymer was precipitated by adding the reaction mixture to a solution of MeOH (100 mL) and concentrated HCl (~1–3 mL). The polymer was then collected on a frit and rinsed with MeOH. The polymer was transferred to a pre-weighed vial and dried under vacuum overnight. A white polyethylene film (5.09 g, ~6050 TO) was isolated.

EXAMPLES 440–468

Ligand Syntheses

Ligand syntheses and deprotonations were carried out according to the general procedures given below and under Examples 1–16 (see above) unless stated otherwise.

EXAMPLE 440

[2-(OH)-3,5—Cl$_2$—C$_6$H$_2$]—C(Me)=NAr
[Ar=2,6-(i-Pr)$_2$—C$_6$H$_3$]

The general procedure for imine synthesis was followed using 10.03 g (48.9 mmol) of 3', 5'-dichloro-2'-hydroxyacetophenone and 11.27 g (1.30 equiv) of 2,6-diisopropylaniline. A yellow powder (15.35 g, 86.2%) was isolated: $^1$H NMR (CDCl$_3$) δ 7.46 (d, 1, Ar': H), 7.44 (d, 1, Ar': H), 7.14 (m, 3, Ar: H), 2.64 (septet, 2, CHMe$_2$), 2.12 (s, 3, N=C(Me)), 1.08 and 1.04 (d, 6 each, CHMeMe').

The sodium salt was synthesized according to the above general procedure: $^1$H NMR (THF-d$_8$): 0.59 equiv of THF coordinated.

EXAMPLE 441

[2-(OH)-3,5-Cl$_2$—C6H$_2$]—C(Me)=NAr
[Ar=2,6-Me$_2$—C$_6$H$_3$]

The general procedure for imine synthesis was followed using 10.681 g (52.1 mmol) of 3', 5'-dichloro-2'-hydroxyacetophenone and 8.21 g (1.30 equiv) of 2,6-dimethylaniline. A yellow powder (7.61 g, 47.4) was isolated: $^1$H NMR (CDCl$_3$) δ 7.57 (d, 1, Ar': H), 7.52 (d, 1, Ar': H), 7.15 (d, 2, Ar: H$_m$), 7.08 (t, 1, Ar: H$_p$), 2.21 (s, 3, N=CMe), 2.10 (s, 6, Ar: Me).

The sodium salt was synthesized according to the above general procedure: $^1$H NMR (THF-d$_8$): 0.59 equiv of THF coordinated.

EXAMPLE 442

[2-(OH)-3,5—Cl$_2$—C$_6$H$_2$]—C(Me)=NAr
[Ar=2-(t-Bu)—C$_6$H$_4$]

The general procedure for imine synthesis was followed using 10.41 g (50.8 mmol) of 3', 5'-dichloro-2'-hydroxyacetophenone and 9.85 g (1.30 equiv) of 2-t-butylaniline. A yellow powder (15.30 g, 89.6%, 2 crops) was isolated: $^1$H NMR (CDCl$_3$ ) δ 7.55 (d, 1, Ar': H), 7.52 (d, 1, Ar': H), 7.50 (d, 1, Ar: H), 7.25 (t, 1, Ar: H), 7.22 (t, 1, Ar: H), 6.52 (d, 1, Ar: H), 2.31 (s, 3, Me), 1.36 (s, 9, CMe$_3$).

The sodium salt was synthesized according to the above general procedure: $^1$H NMR (THF-d$_8$): 0.16 equiv of THF coordinated.

EXAMPLE 443

[2-(OH)-3,5-Br$_2$—C$_6$H$_2$]—CH=NAr
[Ar=2,6-(i-Pr)$_2$—C$_6$H$_3$]

The general procedure for imine synthesis was followed using 3.23 g (11.5 mmol) of 3,5-dibromosalicylaldehyde and 2.66 g (1.30 equiv) of 2,6-diisopropylaniline. A yellow powder (3.10 g, 61.4%) was isolated: $^1$H NMR (CDCl$_3$) 8.21 (s, 1, N=CH), 7.81 (d, 1, Ar': H), 7.45 (d, 1, Ar': H), 7.22 (s, 3, Ar: H), 2.94 (septet, 2, CHMe$_2$), 1.18 (d, 12, CHMe$_2$).

The sodium salt was synthesized according to the above general procedure: $^1$H NMR (THF-d$_8$): 0.7 equiv of THF coordinated.

EXAMPLE 444

[2-(OH)-3,5-Br$_2$—C$_6$H$_2$]—C(Me)=NAr
[Ar=2,6-(i-Pr)$_2$—C$_6$H$_3$]

The general procedure for imine synthesis was followed using 10.84 g (36.9 mmol) of 3',5'-dibromo-2'-hydroxyacetophenone and 8.50 g (1.30 equiv) of 2,6-diisopropylaniline. A yellow powder (13.16 g, 78.7%) was isolated: $^1$H NMR (CDCl$_3$) δ 7.83 (d, 1, Ar': H), 7.73 (d, 1, Ar': H), 7.26 (m, 3, Ar: H), 2.76 (septet, 2, CHMe$_2$), 2.24 (s, 3, Me), 1.19 and 1.18 (d, 6 each, CHMeMe').

The sodium salt was synthesized according to the above general procedure: $^1$H NMR (THF-d$_8$): 0.54 equiv of THF coordinated.

EXAMPLE 445

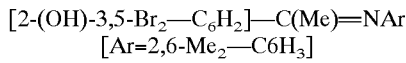
[Ar=2,6-Me$_2$—C6H$_3$]

The general procedure for imine synthesis was followed using 10.43 g (35.5 mmol) of 3',5'-dibromo-2'-hydroxyacetophenone and 5.59 g (1.30 equiv) of 2,6-dimethylaniline. A yellow powder (11.6 g) was isolated. The $^1$H NMR spectrum of the initially isolated product showed that it was contaminated by the hydroxyacetophenone. The product was repurified by washing with more methanol, dissolving in CH$_2$Cl$_2$ and drying over Na$_2$SO$_4$, filtering and evaporating the solvent. A yellow powder (5.60 g) was isolated. The product mixture was now 12.7% of the starting aldehyde. The remainder is the desired imine product: $^1$H NMR (CDCl$_3$) δ 7.78 (d, 1, Ar': H), 7.71 (d, 1, Ar': H), 7.11 (d, 2, Ar: H$_m$), 7.05 (t, 1, Ar: H$_p$), 2.18 (s, 3, N=CMe), 2.05 (s, 6, Ar: Me).

The sodium salt was synthesized according to the above general procedure and is clean and consistent with the desired product (no hydroxyacetophenone impurities present): $^1$H NMR (THF-d$_8$): 0.81 equiv of THF coordinated.

EXAMPLE 446

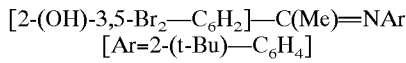
[Ar=2-(t-Bu)—C$_6$H$_4$]

The general procedure for imine synthesis was followed using 10.04 g (34.2 mmol) of 3',5'-dibromo-2'-hydroxyacetophenone and 6.63 g (1.30 eguiv) of 2-t-butylaniline. A yellow powder (12.63 g, 86.9%) was isolated: $^1$H NMR (CDCl$_3$) δ 7.81 (d, 1, Ar': H), 7.72 (d, 1, Ar': H), 7.51 (d, 1, Ar: H), 7.27 (t, 1, Ar: H), 7.22 (t, 1, Ar: H), 6.51 (d, 1, Ar: H), 2.31 (s, 3, N=CMe), 1.37 (s, 9, CMe$_3$).

The sodium salt was synthesized according to the above general procedure: $^1$H NMR (THF-d$_8$): trace THF coordinated.

EXAMPLE 447

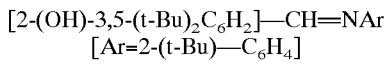
[Ar=2-(t-Bu)—C$_6$H$_4$]

The general procedure for imine synthesis was followed using 4.12 g (17.6 mmol) of 3,5,-di-t-butyl-2-hydroxybenzaldehyde and 3.15 g (1.20 equiv) of 2-t-butylaniline. The desired imine product was isolated as a yellow powder: $^1$H NMR (CDCl$_3$) δ 8.36 (s, 1, N=CH), 7.40 (d, 1, Ar': H), 7.36 (d, 1, Ar: H), 7.18 (t, 1, Ar: H), 7.15 (d, 1, Ar': H), 7.13 (t, 1, Ar: H), 6.80 (d, 1, Ar: H), 1.42, 1.37 and 1.26 (s, 9 each, CMe$_3$, C'Me$_3$, C''Me$_3$).

The sodium salt was synthesized according to the above general procedure: $^1$H NMR (THF-d$_8$): 1 equiv of THF coordinated.

EXAMPLE 448

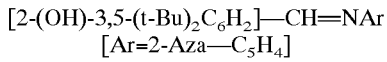
[Ar=2-Aza—C$_5$H$_4$]

The general procedure for imine synthesis was followed using 3.02 g (12.9 mmol) of 3,5-di-t-butyl-2-hydroxybenzaldehyde and 1.46 g (1.20 equiv) of 2-aminopyridine. An orange powder (0.552 g, 13.8%) was isolated: $^1$H NMR (CDCl$_3$) δ 9.47 (s, 1, N=CH), 8.51 (m, 1, Py: H), 7.77 (m, 1, Py: H), 7.48 (d, 1, Ar': H), 7.35 (d, 1, Ar': H), 7.33 (m, 1, Py: H), 7.20 (m, 1, Py: H), 1.48 (s, 9, CMe$_3$), 1.34 (s, 9, C'Me$_3$).

The sodium salt was synthesized according to the above general procedure: $^1$H NMR (THF-d$_8$): 0.2 equiv of THF coordinated.

EXAMPLE 449

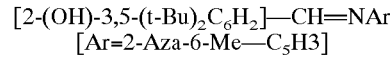
[Ar=2-Aza-6-Me—C$_5$H3]

The general procedure for imine synthesis was followed using 3.46 g (14.7 mmol) of 3,5-di-t-butyl-2-hydroxybenzaldehyde and 1.91 g (1.20 equiv) of 2-amino-3-picoline. The first crop isolated as a precipitate from methanol was an orange powder (1.18 g). This crop was not clean and was discarded, although some of the desired product was present as a minor component. The remaining methanol solution was allowed to slowly evaporate to give orange crystals. The methanol was decanted off of the crystals and the standard work-up procedure was followed. An orange powder (0.813 g) was isolated, and the NMR spectrum of this second crop was clean and consistent with the desired product: $^1$H NMR (CDCl$_3$) δ 9.45 (s,1, N=CH), 8.34 (d, 1, Py: H), 7.60 (d, 1, Py: H), 7.48 (d, 1, Ar': H), 7.38 (d, 1, Ar': H), 7.13 (dd, 1, Py: H), 2.49 (s, 3, Me), 1.5 (s, 9, CMe$_3$), 1.34 (s, 9, C'Me$_3$).

The sodium salt was synthesized according to the above general procedure: $^1$H NMR (THF-d$_8$): 0.4 equiv of THF coordinated.

EXAMPLE 450

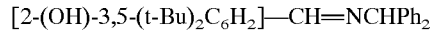

The general procedure for imine synthesis was followed using 3.00 g (12.8 mmol) of 3,5-di-t-butyl-2-hydroxybenzaldehyde and 2.60 g (1.11 equiv) of aminodiphenylmethane. A yellow powder (2.85 g, 55.7%) was isolated: $^1$H NMR (CDCl$_3$) δ 8.50 (s, 1, N=CH), 7.42 (d, 1, Ar': H), 7.40–7.23 (m, 10, CPh$_2$), 7.11 (d, 1, Ar': H), 5.63 (s, 1, CHPh$_2$), 1.48 and 1.32 (s, 9 each, CMe$_3$ and C'Me$_3$).

The sodium salt was synthesized according to the above general procedure: $^1$H NMR (THF-d$_8$): 1 equiv of THF coordinated.

EXAMPLE 451

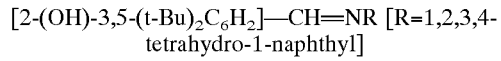
tetrahydro-1-naphthyl]

The general procedure for imine synthesis was followed using 3.08 g (13.1 mmol) of 3,5-di-t-butyl-2-hydroxybenzaldehyde and 2.32 g (1.20 equiv) of 1,2,3,4-tetrahydro-1-naphthylamine. A yellow powder (3.97 g, 83.4%) was isolated: $^1$H NMR (CDCl$_3$) δ 8.45 (s, 1, N=CH), 7.39 (d, 1, Ar': H), 7.22–7.04 (m, 5, Ar: H, Ar': H), 4.53 (m, 1, NCHCH$_2$CH$_2$CH$_2$), 2.88 (m, 2, NCHCH$_2$CH$_2$CH$_2$), 2.14–1.79 (m, 4, NCHCH$_2$CH$_2$CH$_2$), 1.42 (s, 9, CMe$_3$), 1.32 (s, 9, C'Me$_3$).

The sodium salt was synthesized according to the above general procedure: $^1$H NMR (THF-d8): 0.6 equiv of THF coordinated.

EXAMPLE 452

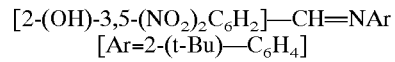
[Ar=2-(t-Bu)—C$_6$H$_4$]

The general procedure for imine synthesis was followed using 3.05 g (14.4 mmol) of 3,5-dinitrosalicylaldehyde and 2.57 g (1.20 equiv) of 2-t-butylaniline. A yellow powder was isolated: $^1$H NMR (CDCl$_3$) δ 8.94 (s, 1, N=CH), 8.54 (d, 1, Ar': H), 8.50 (d, 1, Ar': H), 7.49 (d, 1, Ar: H), 7.35 (t, 1, Ar: H), 7.31 (t, 1, Ar: H), 7.02 (d, 1, Ar: H), 1.40 (s, 9 CMe$_3$).

The sodium salt was synthesized according to the above general procedure: $^1$H NMR (THF-d$_8$): 0.79 equiv of THF coordinated.

EXAMPLE 453

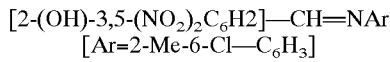
[Ar=2-Me-6-Cl—C$_6$H$_3$]

The general procedure for imine synthesis was followed using 1.56 g (7.33 mmol) of 3,5-dinitrosalicylaldehyde and 1.25 g (1.20 equiv) of 2-chloro-6-methylaniline. An orange powder (1.35 g, 55.0%) was isolated: $^1$H NMR (CDCl$_3$) δ 15.96 (br s, 1, OH), 8.71 (s, 1, N=CH), 8.60 (d, 1, H$_{aryl}$), 7.50–7.15 (m, 4, H$_{aryl}$), 2.36 (s, 1, Me).

The sodium salt was synthesized according to the above general procedure: $^1$H NMR (THF-d$_8$): 0.14 equiv of THF coordinated.

EXAMPLE 454

[2-(OH)-3,5-(NO$_2$)$_2$C$_6$H$_2$]—CH=NR
[R=1,2,3,4-tetrahydro-1-naphthyl]

The general procedure for imine synthesis was followed using 3.07 g (14.5 mmol) of 3,5-dinitrosalicylaldehyde and 2.55 g (1.20 equiv) of 1,2,3,4-tetrahydro-1-naphthylamine. A yellow powder (4.31 g, 87.1%) was isolated: $^1$H NMR (CDCl$_3$) δ 8.98 (d, 1, Ar': H), 8.36 (d, 1, Ar': H), 8.07 (d, 1, Ar: H), 7.36 (m, 1, Ar: H), 7.27 (m, 3, N=CH and Ar: H), 7.15 (d, 1, Ar: H), 5.04 (m, 1, NCHCH$_2$CH$_2$CH$_2$), 2.90 (m, 2, NCHCH$_2$CH$_2$CH$_2$), 2.26, 1.97 and 1.87 (m's, 2, 1 and 1 each, NCHCH$_2$CH$_2$CH$_2$).

The sodium salt was synthesized according to the above general procedure: $^1$H NMR (THF-d$_8$): 0.11 equiv of THF coordinated.

EXAMPLE 455

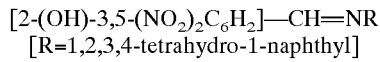
[Ar=2,6-(i-Pr)$_2$—C$_6$H$_3$]

The general procedure for imine synthesis was followed using 6.00 g (16.0 mmol) of 3,5-diiodosalicylaldehyde and 3.70 g (1.31 equiv) of 2,6-diisopropylaniline. A yellow powder (7.93 g, 93.0%) was isolated: $^1$H NMR (CDCl$_3$) δ 8.14 (d, 1, Ar': H), 8.10 (s, 1, N=CH), 7.60 (d, 1, Ar': H), 7.20 (m, 3, Ar: H), 2.92 (septet, 2, CHMe$_2$), 1.18 (d, 12, CHMe$_2$).

The sodium salt was synthesized according to the above general procedure: $^1$H NMR (THF-d$_8$): 0.67 equiv of THF coordinated.

EXAMPLE 456

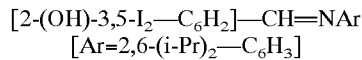
[Ar=2,6-(i-Pr)H—C$_6$H3]

The general procedure for imine synthesis was followed using 5.05 g (27.7 mmol) of 4,6-dimethoxysalicylaldehyde and 5.90 g (1.20 equiv) of 2,6-diisopropylaniline. A yellow powder (3.59 g, 38.0%) was isolated: $^1$H NMR (CDCl$_3$) δ 8.58 (s, 1, N=CH), 7.18 (s, 3, Ar: H), 6.13 (d, 1, Ar': H), 5.92 (d, 1, Ar': H), 3.84 (s, 3, OMe), 3.80 (s, 3, OMe'), 3.03 (septet, 1, CHMe$_2$), 1.19 (d, 12, CHMe$_2$).

The sodium salt was synthesized according to the above general procedure: $^1$H NMR (THF-d$_8$): No THF coordinated.

EXAMPLE 457

[2-Hydroxynaphthyl]—CH=NAr
[Ar=2,6-Br$_2$-4-F—C$_6$H$_2$]

The general procedure for imine synthesis was followed using 29.8 g (173 mmol) of 2-hydroxy-1-naphthaldehyde and 52.0 g (193 mmol) of 2,6-dibromo-4-fluoroaniline. A yellow powder (62.1 g, 84.9%, 2 crops) was isolated: $^1$H NMR (CDCl$_3$) δ 9.40 (s, 1, N=CH), 8.09 (d, 1, Ar': H), 7.92 (d, 1, Ar': H), 7.81 (d, 1, Ar': H), 7.55 (t, 1, Ar': H), 7.43 (d, 2, Ar: H), 7.40 (t, 1, Ar': H), 7.25 (d, 1, Ar': H).

The sodium salt was synthesized according to the above general procedure: $^1$H NMR (THF-d$_8$): 0.66 equiv of THF coordinated.

EXAMPLE 458

[2-Hydroxynaphthyl]—CH=NAr
[Ar=2-Aza-6-Me—C$_5$H$_3$]

The general procedure for imine synthesis was followed using 3.44 g (20.0 mmol) of 2-hydroxy-1-naphthaldehyde and 2.59 g (1.20 equiv) of 2-amino-3-picoline. A yellow-orange powder (4.51 g, 86.0%) was isolated: $^1$H NMR (CDCl$_3$) δ 9.94 (d, 1, H$_{aryl}$), 8.27 (d, 1, N=CH), 8.09 (d, 1, H$_{aryl}$), 7.68 (d, 1, H$_{aryl}$), 7.54 (d, 1, H$_{aryl}$), 7.51 (d, 1, H$_{aryl}$), 7.44 (t, 1, H$_{aryl}$), 7.24 (t, 1, H$_{aryl}$), 7.02 (t, 1, H$_{aryl}$), 6.85 (d, 1, H$_{aryl}$), 2.44 (s, 3, Me).

The sodium salt was synthesized according to the above general procedure: $^1$H NMR (THF-d$_8$): 0.1 equiv of THF coordinated.

EXAMPLE 459

[2-Hydroxynaphthyl]—CH=NAr
[Ar=2-(t-Bu)—C$_6$H$_4$]

The general procedure for imine synthesis was followed using 10.19 g (59.2 mmol) of 2-hydroxy-1-naphthaldehyde and 10.60 g (1.20 equiv) of 2-t-butylaniline. A yellow powder (10.8 g, 60.4%) was isolated: $^1$H NMR (CDCl$_3$) δ 9.27 (d, 1, N=CH), 8.18 (d, 1, H$_{aryl}$), 7.88 (d, 1, H$_{aryl}$), 7.79 (d, 1, H$_{aryl}$), 7.55 (t, 1, H$_{aryl}$) 7.52 (d, 1, H$_{aryl}$) 7.39 (t, 1, H$_{aryl}$) 7.37 (t, 1, H$_{aryl}$) 7.30 (t, 1, H$_{aryl}$) 7.21 (d, 1, H$_{aryl}$) 7.19 (d, 1, H$_{aryl}$), 1.52 (s, 9, CMe$_3$).

The sodium salt was synthesized according to the above general procedure: $^1$H NMR (THF-d$_8$): 0.48 equiv of THF coordinated.

EXAMPLE 460

(Ar)(H)N—C(Me)=CH—C(O)—Ph
[Ar=2,6-(i-Pr)$_2$—C6H$_3$]

The general procedure for imine synthesis was followed using 5.17 g (31.9 mmol) of 1-benzoylacetone and 7.35 g (1.30 equiv) of 2,6-diisopropylaniline. After 2 days, no precipitate formed from the methanol solution. However, slow evaporation of the methanol yielded single crystals, which were isolated and washed with a small amount of additional methanol. The standard work-up procedure was then followed to yield a white powder (2.56 g, 25.0%): $^1$H NMR (CDCl$_3$) δ 7.89 (d, 2, H$_{aryl}$), 7.38 (m, 3, H$_{aryl}$) 7.25 (t, 1, H$_{aryl}$), 7.12 (d, 1, H$_{aryl}$), 5.86 (s, 1, =CH), 3.02 (septet, 2, ChMe$_2$), 1.71 (s, 3, N—C(Me)), 1.17 and 1.11 (d, 6 each, CHMeMe'); $^{13}$C NMR (CDCl$_3$) δ 188.4 (C(O)), 165.0 (N—C(Me)), 146.2 (Ar: C$_o$), 140.0 and 133.5 (Ph: C$_{ipso}$; Ar: C$_{ipso}$)) 130.8 and 128.3 (Ar: C$_p$; Ph: C$_p$), 128.1, 127.1 and 123.5 (Ph: C$_o$, C$_m$; Ar: C$_m$), 92.1 (C(Me)=CH), 28.5 (CHMe$_2$), 24.6 and 22.7 (CHMeMe'), 19.7 (N—C(Me)).

The sodium salt was synthesized according to the above general procedure: $^1$H NMR (THF-d$_8$): 0.66 equiv of THF coordinated.

EXAMPLE 461

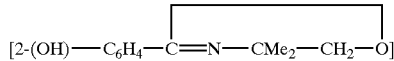

A 200 mL sidearm flask was charged with 5.0 g (42 mmol, 1.0 equiv) of 2-hydroxybenzonitrile, 5.6 g (63 mmol, 1.5 equiv) of 2-amino-2-methylpropanol, 0.29 g (2.1 mmol, 0.05 equiv) of ZnCl$_2$, and 90 mL of chlorobenzene. The reaction mixture was heated to reflux under N$_2$ atmosphere for 24 h. After this time, reflux was discontinued, the flask was cooled to ambient temperature, and most of the volatile materials were removed using a rotary evaporator. The resulting residue was dissolved in ~100 mL of CH$_2$Cl$_2$, transferred to a separatory funnel, and washed with 3×50 mL of H$_2$O. The combined H$_2$O washings were back extracted with 30 mL of CH$_2$Cl$_2$, and the combined CH$_2$Cl$_2$ extracts were then dried over Na$_2$SO$_4$, filtered and evaporated to yield a brown oil which was purified by flash chromatography (SiO$_2$, eluting with 5:1 hexanes:EtOAc), to yield 6.3 g (78%) of the desired product: $^1$H NMR (CDCl$_3$) δ 12.2 (br s, 1, OH), 7.6 (m, 1, H$_{aryl}$), 7.4 (m, 1, H$_{aryl}$), 7.06 (m, 1, H$_{aryl}$), 6.92 (m, 1, H$_{aryl}$), 4.14 (s, 2, CH$_2$), 1.44 (s, 6, CMe$_2$).

The sodium salt was synthesized according to the above general procedure: $^1$H NMR (THF-d$_8$): 0.20 equiv of THF coordinated.

EXAMPLE 462

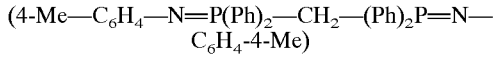

See Phosphorus, Sulfur, and Silicon 1990, 47, 401. A 100-mL 3-neck round-bottomed flask was fitted with a condenser, a nitrogen inlet and an addition funnel. It was charged with 2.64 g (6.87 mmol) of bis(diphenylphosphino) methane (DPPM) dissolved in 17 mL of benzene. The addition funnel was charged with 1.86 g (14.0 mmol) of 4-Me—C$_6$H$_4$—N$_3$ (prepared from p-toluidine hydrochloride, sodium nitrite and sodium azide, see Ugi, I; Perlinger, H.; Behringer, L. Chemische Berichte 1958, 91, 2330) dissolved in ca. 7–10 mL of benzene. The DPPM solution was heated to 60° C. and the aryl azide solution slowly added to the reaction mixture. As the addition occurred, nitrogen was evolved. After the addition was completed, the reaction mixture was kept an additional 4 h at 60° C. The solvent was then removed in vacuo, and the solid was collected, washed with 2×15 mL of hexane and dried in vacuo. The yield was 3.75 g (92%): $^1$H NMR (CDCl$_3$) δ 7.72 (m, 8, PPh$_2$: H$_o$) 7.41 (t, 4, PPh$_2$: H$_p$), 7.29 (t, 3, PPh$_2$: H$_m$), 6.83 (d, 4, NAr: H$_m$), 6.52 (d, 4, NAr: H$_o$), 3.68 (t, 2, J$_{HP}$=14.2, PCH$_2$P), 2.21 (s, 6, NAr: Me).

The sodium salt was synthesized according to the above general procedure: $^1$H NMR (THF-d$_8$): 0.39 equiv of THF coordinated.

EXAMPLE 463

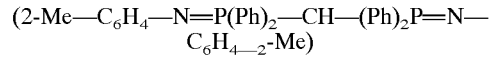

A 100-mL 3-neck round-bottomed flask was fitted with a condenser, a nitrogen inlet and an addition funnel. It was charged with 3.0 g (7.80 mmol) of bis(diphenylphosphino) methane (DPPM) dissolved in 20 mL of toluene. The addition funnel was charged with 2.11 g (15.8 mmol) of 2-Me—C$_6$H$_4$—N$_3$ (prepared from o-toluidine hydrochloride, sodium nitrite and sodium azide) dissolved in ca. 12 mL of toluene. The DPPM solution was heated to 60° C. and the aryl azide solution slowly added to the reaction mixture. As the addition occurred, nitrogen was evolved. After the addition was completed, the reaction mixture was kept an additional 4 h at 60° C. The solvent was then removed in vacuo, the solid was collected and recrystallized from Et$_2$O/hexane. The yield was 2.70 g (58%). $^1$H NMR (CDCl$_3$) δ 7.68 (m, 8, PPh$_2$: H$_o$), 7.38 (t, 4, PPh$_2$: H$_p$), 7.25 (t, 8, PPh$_2$: H$_m$), 7.09 (d, 2, NAr: H$_m$') 6.76 (t, 2, NAr: H$_m$), 6.23 (t, 2, NAr: H$_p$), 6.23 (d, 2, NAr: H$_o$) 3.87 (t, 2, J$_{HP}$=13.5, PCH$_2$P), 2.29 (s, 6, NAr: Me).

The sodium salt was synthesized according to the above general procedure: $^1$H NMR (THF-d$_8$): 0.59 equiv of THF coordinated.

EXAMPLE 464

Lithium 5-Methyl-2-Thiophenecarboxylate

The sodium salt was synthesized from commercially available 5-methyl-2-thiophenecarboxylic acid according to the above general procedure and the cation was exchanged with an excess of lithium chloride to improve product solubility: $^1$H NMR (THF-d$_8$): 0.25 equiv of THF coordinated.

EXAMPLE 465

Cy$_2$PCH$_2$CH(CH$_3$)SLi

A 100-mL Schlenk flask was charged with 1.28 g (6.28 mmol) of PCy$_2$Li (prepared from PCy$_2$H and n-BuLi) dissolved in 20 mL of THF. The flask was cooled to −78° C. and propylene sulfide (520 mg, 7.01 mmol) was vacuum transferred onto the lithium salt solution. The reaction mixture was kept at −78° C. for 45 min. The dry ice/acetone bath was then removed and the yellowish solution was allowed to warm to ambient temperature. After an additional 20 min, the solvent was removed in vacuo. The solid was washed three times with 30 mL of hexane and dried in vacuo. The yield was 1.37 g (78%). $^1$H NMR (THF-d$_8$, 300 MHz, 23° C.) δ 2.80 (m, 1, CH), 1.31 (d, 3, J=6 Hz, CH$_3$), 1–2 (m, 24, Cy$_2$, PCH$_2$); $^{31}$P NMR: δ −7.6.

EXAMPLE 466

Sodium 2,3,5,6-Tetrachloro-4-Pyridinethiolate

The sodium salt was synthesized according to the above general procedure from the commercially available 2,3,5,6-tetrachloro-4-pyridinethiol.

EXAMPLE 467

Sodium 2,5-Dimethylpyrrole

The sodium salt was synthesized according to the above general procedure from the commercially available 2,5-dimethylpyrrole: $^1$H NMR (THF-d$_8$): No THF coordinated.

EXAMPLE 468

Sodium 2,6-Dibromo-4-Methylanilide

The sodium salt was synthesized according to the above general procedure from the commercially available 2,6- dibromo-4-methylaniline: $^1$H NMR (THF-d$_8$): 0.5 equiv THF coordinated.

EXAMPLES 469–498

Complexes 21 through 49 were synthesized according to the general procedure for the synthesis of allyl initiators (see above under Examples 17–40).

EXAMPLE 469

Complex 21a. Two equiv (2.77 g, 6.45 mmol) of the sodium salt of the ligand were reacted with one equiv (1.53 g, 3.22 mmol) of [(allyl)Ni($\mu$-Br)]$_2$ (allyl=H$_2$CC(CO$_2$Me)CH$_2$) to give 2.94 g (87.4% yield) of a yellow powder: $^1$H NMR (C$_6$D$_6$) δ 7.39 (d, 1, Ar': H), 7.29 (d, 1, Ar': H), 7.0–6.9 (m, 3, Ar: H), 4.00 (m, 1, HH'CC(CO$_2$Me)C'HH'), 3.57 and 2.86 (septet, 1 each, CHMe$_2$ and C'HMe$_2$), 3.25 (s, 3, OMe), 2.86 (s, 1, HH'CC(CO$_2$Me)C'HH'), 1.92 (m, 1, HH'CC(CO$_2$Me)C'HH'), 1.47 (s, 3, N=CMe), 1.34, 1.18, 0.89 and 0.79 (d, 3 each, CHMeMe' and C'HMeMe'), 1.12 (s, 1 each, HH'CC(CO$_2$Me)C'HH').

EXAMPLE 470

Complex 21b. Two equiv (720 mg, 1.68 mmol) of the sodium salt of the ligand were reacted with one equiv (225 mg, 0.834 mmol) of [(allyl)Ni($\mu$-Br)]$_2$ (allyl=H$_2$CCHCH$_2$) to give 599 mg (77.6% yield) of a yellow powder: $^1$H NMR (CDCl$_3$) δ 7.39 (d, 1, Ar': H), 7.35 (d, 1, Ar': H), 7.13–7.00 (m, 3, Ar: H), 5.78 (m, 1, H$_2$CCHC'H$_2$), 3.66 and 3.07 (m, 1 each, CHMe$_2$ and C'HMe$_2$), 3.21, 2.64, 1.44 and 1.11 (d, 1 each, HH'CCHC'HH'), 1.99 (s, 3, N=CMe), 1.31, 1.26, 1.07 and 0.99 (d, 3 each, CHMeMe' and C'HMeMe'); $^{13}$C NMR (CDCl$_3$) δ 168.7 (N=CMe), 159.5, 150.0, 137.7, 137.0, 131.8, 128.7, 127.9, 125.9, 123.8, 123.3, 120.9, 117.1., 113.1 (Ar: C$_o$, C$_o$', C$_m$, C$_m$', C$_p$, Ar': C$_o$, C$_o$', C$_m$, C$_m$', C$_p$, H$_2$CCHCH$_2$), 59.4 and 52.8 (H$_2$CCHC'H$_2$), 28.3 and 27.8 (CHMe$_2$, C'HMe$_2$), 24.1, 23.64, 23.54 and 23.4 (CHMeMe' and C'HMeMe'), 20.3 (N=CMe).

EXAMPLE 471

Complex 22a. Two equiv (809 mg, 2.14 mmol) of the sodium salt of the ligand were reacted with one equiv (508 mg, 1.07 mmol) of [(allyl)Ni($\mu$-Br)]$_2$ (allyl=H$_2$CC(CO$_2$Me)CH$_2$) to give 792 mg (79.6% yield) of a yellow powder: $^1$H NMR (C$_6$D$_6$) δ 7.57 (d, 1, Ar': H), 7.30 (d, 1, Ar': H), 7.0–6.9 (m, 3, Ar: H), 4.10 (m, 1, HH'CC(CO$_2$Me)C'HH'), 3.38 (s, 3, OMe), 2.69 (s, 1, HH'CC(CO$_2$Me)C'HH'), 2.02 and 2.12 (s, 3, Ar: Me, Me'), 1.89 (m, 1, HH'CC(CO$_2$Me)C'HH'), 1.45 (s, 3, N=CMe), 1.35 (s, 1, HH'CC(CO$_2$Me)C'HH')

EXAMPLE 472

Complex 23a. Two equiv (1.56 g, 4.20 mmol) of the sodium salt of the ligand were reacted with one equiv (1.00 g, 2.10 mmol) of [(allyl)Ni($\mu$-Br)]$_2$ (allyl=H$_2$CC(CO$_2$Me)CH$_2$) to give 1.35 g (65.3% yield) of a yellow powder: According to the $^1$H NMR spectrum, two isomers (t-Bu group positioned syn and anti to the CO$_2$Me group) are present in a 1:1 ratio. $^1$H NMR (C$_6$D$_6$) δ 7.6–6.5 (m, 8, H$_{aryl}$), 4.16 and 4.01 (s, 1 each, HH'CC(CO$_2$Me)C'HH' of each isomer), 3.42 and 3.42 (s, 3 each, OMe of each isomer), 2.82 and 2.74 (s, 1 each, HH'CC(CO$_2$Me)C'HH' of each isomer), 2.22 and 2.02 (s, 1 each, HH'CC(CO$_2$Me)C'HH' of each isomer), 1.63 and 1.56 (s, 3 each, N=CMe of each isomer), 1.56 and 1.38 (s, 9 each, CMe$_3$ of each isomer), 1.54 and 1.36 (s, 1 each, HH'CC(CO$_2$Me)C'HH' of each isomer).

EXAMPLE 473

Complex 24a. Two equiv (1.10 g, 2.15 mmol) of the sodium salt of the ligand were reacted with one equiv (512 mg, 1.08 mmol) of [(allyl)Ni($\mu$-Br)]$_2$ (allyl=H$_2$CC(CO$_2$Me)CH$_2$) to give 635 mg (49.5% yield) of a yellow powder: $^1$H NMR (CDCl$_3$) δ 7.72 (s, 1, N=CH), 7.70 (d, 1, Ar': H), 7.20–7.08 (m, 4, Ar: H, Ar': H), 3.90 (d, 1, HH'CC(CO$_2$Me)C'HH'), 3.80 (s, 3, OMe), 3.73 and 2.92 (septet, 1 each, CHMe$_2$ and C'EMe$_2$), 2.99 (s, 1, HH'CC(CO$_2$Me)C'HH'), 2.03 (m, 1, HH'CC(CO$_2$Me)C'HH'), 1.56 (s, 1, HH'CC(CO$_2$Me)C'HH'), 1.30, 1.22, 1.08 and 0.93 (d, 3 each, CHMeMe' and C'HMeMe').

EXAMPLE 474

Complex 25a. Two equiv (3.25 g, 6.31 mmol) of the sodium salt of the ligand were reacted with one equiv (1.50 g, 3.16 mmol) of [(allyl)Ni($\mu$-Br)]$_2$ (allyl=H$_2$CC(CO$_2$Me)CH$_2$) to give 3.49 g (90.6% yield) of a yellow powder: $^1$H NMR spectrum is clean and consistent with the desired product.

EXAMPLE 475

Complex 26a. Two equiv (2.01 g, 4.20 mmol) of the sodium salt of the ligand were reacted with one equiv (1.00 g, 2.10 mmol) of [(allyl)Ni($\mu$-Br)]$_2$ (allyl H$_2$CC(CO$_2$Me)CH$_2$) to give 1.51 g (64.9% yield) of a golden brown powder: $^1$H NMR (C$_6$D$_6$) δ 7.64 (s, 1, Ar': H), 7.25 (s, 1, Ar': H), 6.70 (, 3, Ar: H), 3.85 (s, 1, HH'CC(CO$_2$Me)C'HH'), 3.15 (s, 3, OMe), 2.44 (s, 1, HH'CC(CO$_2$Me)CHH'), 1.97 and 1.85 (s, 3 each, Ar: Me, Me'), 1.60 (s, 1, HH'CC(CO$_2$Me)C'HH'), 1.20 (s, 3, N=CMe), 1.11 (s, 1, HH'CC(CO$_2$Me)C'HH'); $^{13}$C NMR (C$_6$D$_6$, selected resonances) δ 59.5, 52.7, and 51.3 (H$_2$CC(CO$_2$Me)C'H$_2$), 19.0, 18.6, and 18.0 (N=CMe, Ar: Me, Me').

EXAMPLE 476

Complex 27a. Two equiv (951 mg, 2.13 mmol) of the sodium salt of the ligand were reacted with one equiv (505 mg, 1.06 mmol) of [(allyl)Ni($\mu$-Br)]$_2$ (allyl=H$_2$CC(CO$_2$Me)CH$_2$) to give 851 mg (68.6% yield) of a yellow powder: $^1$H NMR spectrum in C$_6$D$_6$ is clean and consistent with the desired product. The product exists as a 1:1 ratio of isomers (t-Bu group positioned syn or anti to the CC$_2$Me group.)

EXAMPLE 477

Complex 28a. Two equiv (983 mg, 2.14 mmol) of the sodium salt of the ligand were reacted with one equiv (509 mg, 1.07 mmol) of [(allyl)Ni($\mu$-Br)]$_2$ (allyl=H$_2$CC(CO$_2$Me)CH$_2$) to give 1.02 g (90.9% yield) of a green powder: $^1$H NMR spectrum in C$_6$D$_6$ is broad, but consistent with the desired product. The product exists as an ~1:1 ratio of isomers (t-Bu group positioned syn or anti to the CO$_2$Me group.)

EXAMPLE 478

Complex 29a. Two equiv (550 mg, 1.59 mmol) of the sodium salt of the ligand were reacted with one equiv (308 mg, 0.647 mmol) of [(allyl)Ni($\mu$-Br)]$_2$ (allyl=H$_2$CC(CO$_2$Me)CH$_2$) to give 478 mg (64.3% yield) of a dark brown powder.

EXAMPLE 479

Complex 30a. Two equiv (478 mg, 1.27 mmol) of the sodium salt of the ligand were reacted with one equiv (303 mg, 0.637 mmol) of [(allyl)Ni($\mu$-Br)]$_2$ (allyl=H$_2$CC(CO$_2$Me)CH$_2$) to give 375 mg (61.4% yield) of a dark brown powder:

EXAMPLE 480

Complex 31a. Two equiv (1.04 g, 2.10 mmol) of the sodium salt of the ligand were reacted with one equiv (500 mg, 1.05 mmol) of [(allyl)Ni($\mu$-Br)]$_2$ (allyl=H$_2$CC(CO$_2$Me)CH$_2$) to give 948 mg (81.1% yield) of a green-yellow powder: $^1$H NMR (THF-d$_8$) $\delta$ 7.85, 7.34, 7.14, 7.12, 6.63 and 6.43 (N=CH, H$_{aryl}$, CHPh$_2$), 3.72 (s, 3, OMe), 3.80, 2.78, 2.78, and 1.48 (s, 1 each, HH'CC(CO$_2$Me)C'HH'), 1.37 and 1.18 (CMe$_3$, C'Me$_3$); $^{13}$C NMR (THF-d$_8$) $\delta$ 166.9 (N=CH), 167.1, 166.9, 164.1, 142.3, 142.0, 140.9, 135.8, 130.3, 130.0, 129.4, 129.3, 129.27, 128.3, 118.3, 110.4 (C$_{aryl}$ and H$_2$CC(CO$_2$Me)CH$_2$), 81.0 (CHPh2), 59.1 and 45.8 (H$_2$CC(CO$_2$Me)CH$_2$), 52.6 (OMe), 35.9 and 34.3 (CMe$_3$, C'Me$_3$), 31.7 and 29.7 (CMe$_3$, C'Me$_3$).

EXAMPLE 481

Complex 32a. Two equiv (923 mg, 2.15 mmol) of the sodium salt of the ligand were reacted with one equiv (512 mg, 1.08 mmol) of [(allyl)Ni($\mu$-Br)]$_2$ (allyl=H$_2$CC(CO$_2$Me)CH$_2$) to give 907 mg (81.1% yield) of a brown-orange powder.

EXAMPLE 482

Complex 33a. Two equiv (891 mg, 2.11 mmol) of the sodium salt of the ligand were reacted with one equiv (502 mg, 1.06 mmol) of [(allyl)Ni($\mu$-Br)]$_2$ (allyl=H$_2$CC(CO$_2$Me)CH$_2$) to give 940 mg (89.1% yield) of a gold powder. Two major isomers are present in a 1.18:1 ratio. There is a very small amount of a third product or isomer present. The $^1$H NMR assignments of the two major isomers follow: $^1$H NMR (CDCl$_3$) $\delta$ 8.30 and 8.25 (d, 1 each, Ar': H of each isomer), 7.48 and 7.32 (d, 1 each, Ar': H of each isomer), 6.94 and 6.78 (s, 1 each, N=CH of each isomer), 7.05 (m, 2, H$_{aryl}$), 6.83 (m, 1, H$_{aryl}$), 6.80 (m, 3, H$_{aryl}$), 6.58 (d, 1, H$_{aryl}$), 6.45 (m, 1, H$_{aryl}$), 3.90 and 3.73 (m, 1 each, HH'CC(CO$_2$Me)C'HH' of each isomer), 3.18 and 3.09 (s, 3 each, OMe of each isomer), 2.43 and 2.41 (s, 1 each, HH'CC(CO$_2$Me)C'HH' of each isomer), 2.26 and 2.08 (m, 1 each, HH'CC(CO$_2$Me)C'HH' of each isomer), 1.30 and 1.17 (s, 1 each, HH'CC(CO$_2$Me)C'HH' of each isomer), 1.18 and 1.03 (s, 9 each, CMe$_3$ of each isomer).

EXAMPLE 483

Complex 34a. Two equiv (719 mg, 1.95 mmol) of the sodium salt of the ligand were reacted with one equiv (464 mg, 0.977 mmol) of [(allyl)Ni($\mu$-Br)]$_2$ (allyl=H$_2$CC(CO$_2$Me)CH$_2$) to give 928 mg (96.6% yield) of a yellow powder. The $^1$H NMR spectrum indicates that two isomers (Cl group positioned syn and anti to the CO$_2$Me group) are present in a 2.5 to 1 ratio. Major Isomer: $^1$H NMR (C$_6$D$_6$) $\delta$ 8.50 (d, 1, Ar': H), 7.52 (d, 1, Ar': H), 7.10 (d, 1, Ar: H), 6.75 (t, 1, Ar: H), 6.72 (s, 1, N=CH), 6.70 (d, 1, Ar: H), 4.02 (d, 1, HH'CC(CO$_2$Me)C'HH'), 3.28 (s, 3, OMe), 2.60 (s, 1, HH'CC(CO$_2$Me)C'HH'), 2.18 (d, 1, HH'CC(CO$_2$Me)C'HH'), 1.99 (s, 3, Ar: Me), 1.63 (s, 1, HH'CC(CO$_2$Me)C'HH'); Minor Isomer: $^1$H NMR (C$_6$D$_6$) $\delta$ 8.50 (d, 1, Ar': H), 7.53 (d, 1, Ar': H), 7.06 (d, 1, Ar: H), 6.8–6.7 (m, 3, N=CH, Ar: H), 4.10 (d, 1, HH'CC(CO$_2$Me)C'HH'), 3.39 (s, 3, OMe), 2.57 (s, 1, HH'CC(CO$_2$Me)C'HH'), 2.19 (d, 1, HH'CC(CO$_2$Me)C'HH'), 1.98 (s, 3, Ar: Me), 1.35 (s, 1, HH'CC(CO$_2$Me)C'HH').

EXAMPLE 484

Complex 35a. Two equiv (765 mg, 2.11 mmol) of the sodium salt of the ligand were reacted with one equiv (500 mg, 1.05 mmol) of [(allyl)Ni($\mu$-Br)]$_2$ (allyl=H$_2$CC(CO$_2$Me)CH$_2$) to give 890 mg (84.7% yield) of a red powder.

EXAMPLE 485

Complex 36a. Two equiv (1.22 g, 2.10 mmol) of the sodium salt of the ligand were reacted with one equiv (500 mg, 1.05 mmol) of [(allyl)Ni($\mu$-Br)]$_2$ (allyl=H$_2$CC(CO$_2$Me)CH$_2$) to give 1.18 g (81.7% yield) of a yellow powder: $^1$H NMR (CD$_2$Cl$_2$) $\delta$ 8.03 (d, 1, Ar': H), 7.70 (s, 1, N=CH), 7.36 (d, 1, Ar': H), 7.20–7.07 (m, 3, Ar: H), 3.88 (m, 1, HH'C(CO$_2$Me)C'HH'), 3.78 (s, 3, OMe), 3.71 (septet, 1, CHMe$_2$), 2.97 (s, 1, HH'CC(CO$_2$Me)C'HH'), 2.90 (septet, 1, C'HMe$_2$), 1.96 (m, 1, HH'CC(CO$_2$Me)C'HH'), 1.57 (s, 1 HH"CC(CO$_2$Me)CHH'), 1.28, 1.20, 1.04 and 0.90 (d, 3 each, CHMeMe', C'HMeMe'); $^{13}$C NMR (CD$_2$Cl$_2$) $\delta$ 166.8 (N=CH), 167.9, 164.6, 153.2, 151.6, 144.4, 141.4, 140.6, 128.4, 125.3, 125.2, 121.1, 114.2, 98.2 and 75.2 (Ar: C$_o$, C$_o$', C$_m$, C$_m$', C$_p$; Ar': C$_o$, C$_o$', C$_m$, C$_m$', C$_p$; H$_2$CC(CO$_2$Me)C'H$_2$), 62.7, 54.5 and 50.2 (H$_2$CC(CO$_2$Me)C'H$_2$), 30.2 and 29.8 (CHMe$_2$, C'HMe$_2$), 26.7, 26.5, 24.2 and 23.7 (CHMeMe', C'HMeMe').

EXAMPLE 486

Complex 37a. Two equiv (771 mg, 2.12 mmol) of the sodium salt of the ligand were reacted with one equiv (504 mg, 1.06 mmol) of [(allyl)Ni($\mu$-Br)]$_2$ (allyl=H$_2$CC(CO$_2$Me)CH$_2$) to give 992 mg (93.9% yield) of a green powder: $^1$H NMR (CD$_2$Cl$_2$) $\delta$ 8.25 (s, 1, N=CH), 7.18 (m, 3, Ar: H), 6.02 (d, 2, Ar': H), 5.68 (d, 2, Ar': H), 3.90 (septet, 1, CHMe$_2$), 3.84, 3.78 and 3.71 (s, 3 each, Ar: OMe and OMe'; CO$_2$Me), 3.65 (s, 1, HH'CC(CO$_2$Me)C'HH'), 3.03 (septet, 1, C'HMe$_2$), 2.80 (s, 1, HH'CC(CO$_2$Me)C'HH'), 1.88 (s, 1, HH'CC(CO$_2$Me)C'HH'), 1.46 (s, 1, HH'CC(CO$_2$Me)C'HH'), 1.36, 1.28, 1.14 and 0.99 (d, 3 each, CHMeMe', C'HMeMe').

EXAMPLE 487

Complex 38a. Two equiv (1.04 g, 2.12 mmol) of the sodium salt of the ligand were reacted with one equiv (503 mg, 1.06 mmol) of [(allyl)Ni($\mu$-Br)]$_2$ (allyl=H$_2$CC(CO$_2$Me)CH$_2$) to give 1.10 g (89.3% yield) of a green-yellow powder: $^1$H NMR (CD$_2$Cl$_2$) $\delta$ 8.65 (s, 1, N=CH), 7.84 (d, 1, Ar': H), 7.77 (d, 1, Ar': H), 7.68 (t, 1, Ar': H), 7.48 (m, 2, Ar: H), 7.44 (t, 1, Ar': H), 7.27 (t, 1, Ar': H), 7.07 (d, 1, Ar': H), 3.86 (s, 3, OMe), 3.80, 2.84, 2.05 and 1.91 (s, 1 each, HH'CC(CO$_2$Me) C'HH').

EXAMPLE 488

Complex 39a. Two equiv (614 mg, 2.10 mmol) of the sodium salt of the ligand were reacted with one equiv (500 mg, 1.05 mmol) of [(allyl)Ni($\mu$-Br)]$_2$ (allyl=H$_2$CC(CO$_2$Me)CH$_2$) to give 683 mg (77.6% yield) of a green-yellow powder: $^1$H NMR (C$_6$D$_6$) $\delta$ 9.17 (s, 1, N=CH), 8.39 (d, 1, H$_{aryl}$), 7.62 (d, 1, H$_{aryl}$), 7.52 (d, 1, H$_{aryl}$), 7.52 (d, 1, H$_{aryl}$), 7.44 (d, 1, H$_{aryl}$), 7.24 (t, 1, H$_{aryl}$), 7.18 (t, 1, H$_{aryl}$), 7.11 (d, 1, H$_{aryl}$), 6.75 (dd, 1, H$_{aryl}$), 4.19 (br s, 1, HH'CC(CO$_2$Me) C'HH'), 3.43 (s, 3, OMe), 2.67 (br s, 1, HH'CC(CO$_2$Me) C'HH'), 2.32 (br s, 1, HH'CC(CO$_2$Me)C'HH'), 2.24 (s, 3, Ar: Me), 1.65 (s, 1, HH'CC (CO$_2$Me) C'HH').

EXAMPLE 489

Compound 40a. Two equiv (765 mg, 2.12 mmol) of the sodium salt of the ligand were reacted with one equiv (505 mg, 1.06 mmol) of [(allyl)Ni($\mu$-Br)]$_2$ (allyl=H$_2$CC(CO$_2$Me)CH$_2$) to give 925 mg (95.1% yield) of a green powder: Three isomers or products are present in a 1.35 to 1.02 to 1.00 ratio. $^1$H NMR (CDCl$_3$, selected resonances only) δ 8.84, 8.72 and 8.20 (N=CH of the 3 products), 3.29 (OMe of the 3 products—all overlapping), 1.81, 1.45 and 1.25 (CMe$_3$ of the 3 products).

EXAMPLE 490

Complex 41a. Two equiv (867 mg, 2.22 mmol) of the sodium salt of the ligand were reacted with one equiv (527 mg, 1.11 mmol) of [(allyl)Ni($\mu$-Br)]$_2$ (allyl=H$_2$CC(CO$_2$Me)CH$_2$) to give 782 mg (77.1% yield) of a golden brown powder: $^1$H NMR (C$_6$D$_6$) δ 8.08 (d, 2, Ph: C$_o$) 7.27 (m, 6, Ph: C$_m$, C$_p$; Ar: C$_m$, C$_p$), 6.01 (s, 1, PhCCHCMe), 4.23 (s, 1, HH'CC(CO$_2$Me)C'HH'), 4.03 (septet, 1, CHMe$_2$), 3.45 (s, 3, OMe), 3.33 (septet, 1, C'HMe$_2$), 3.04 (s, 1, HH'CC(CO$_2$Me)C'HH'), 2.18 (s, 1, HH'CC(CO$_2$Me)CHH'), 1.69 (s, 3, CMeNAr), 1.38 (s, 1, HH'CC(CO$_2$Me)CHH'), 1.54, 1.41, 1.29 and 1.18 (d, 3 each, CHMeMe' and C'HMeMe').

EXAMPLE 491

Complex 42a. Two equiv (495 mg, 2.17 mmol) of the sodium salt of the ligand were reacted with one equiv (516 mg, 1.09 mmol) of [(allyl)Ni($\mu$-Br)]$_2$ (allyl=H$_2$CC(CO$_2$Me)CH$_2$) to give 434 mg (57.4% yield) of a yellow powder: $^1$H NMR (C$_6$D$_6$) δ 7.82 (d, 1, H$_{aryl}$), 7.20 (d, 1, H$_{aryl}$), 7.10 (t, 1, H$_{aryl}$), 6.47 (t, 1, H$_{aryl}$), 4.10 (s, 1, HH'CC(CO$_2$Me)C'HH'), 3.27 (s, 3, OMe), 3.27 (s, 2, OCH$_2$, overlaps with OMe), 3.02, 2.73 and 1.11 (s, 1 each, HH'CC(CO$_2$Me)C'HH'), 0.81 and 0.73 (s, 3 each, CMeMe').

EXAMPLE 492

Complex 43a. Two equiv (586 mg, 0.909 mmol) of the sodium salt of the ligand were reacted with one equiv (216 mg, 0.455 mmol) of [(allyl)Ni($\mu$-Br)]$_2$ (allyl=H$_2$CC(CO$_2$Me)CH$_2$) to give 506 mg (74.1% yield) of a dark red powder: $^1$H NMR (THF-d$_8$) δ 7.50 (m, 8, PPh: H$_o$), 7.20 (t, 4, PPh: H$_p$), 7.10 (t, 8, PPh: H$_m$), 6.65 (d, 4, NAr: H$_m$), 6.59 (d, 4, NAr: H$_o$), 3.52 (s, 3, OMe), 2.77 (s, 2, HH'CC(CO$_2$Me)CHH'), 2.03 (s, 6, NAr: Me), 2.03 or 1.81 (m, 1, PCHP), 1.72 (s, 2, HH'CC(CO$_2$Me)CHH'); $^{13}$C NMR (THF-d$_8$, selected resonances only) δ 50.9 and 47.9 (H$_2$CC(CO$_2$Me)CH$_2$), 19.5 (NAr: Me), 12.0 (t, J$_{CP}$=109 Hz, PCHP)

EXAMPLE 493

Complex 44a. Two equiv (343 mg, 0.520 mmol) of the sodium salt of the ligand were reacted with one equiv (124 mg, 0.260 mmol) of [(allyl)Ni($\mu$-Br)]$_2$ (allyl=H$_2$CC(CO$_2$Me)CH$_2$) to give 128 mg (32.8% yield) of an orange powder. The $^1$H NMR spectrum is consistent with the presence of one major symmetrical isomer; some of the ligand is also present along with some impurities and possibly the presence of other isomers. (The three possible isomers include the isomer with both methyl groups anti to the CO$_2$Me group, the isomer with both methyl groups syn to the CO$_2$Me group, and the isomer with one Me group anti and one Me group syn to the CO$_2$Me group). The nonaromatic resonances of the major symmetrical isomer follow: $^1$H NMR (THF-d$_8$) δ 3.60 (s, 3, OMe), 2.77 (s, 2, HH'CC(CO$_2$Me)CHH'), 3.47 or 2.01 (m, 1, PCHP), 1.88 (s, 6, Ar: Me), 1.75 (s, 2, HH'CC(CO$_2$Me)CHH').

EXAMPLE 494

Complex 45a. Two equiv (349 mg, 2.10 mmol) of the lithium salt of the ligand were reacted with one equiv (500 mg, 1.05 mmol) of [(allyl)Ni($\mu$-Br)]$_2$ (allyl=H$_2$CC(CO$_2$Me)CH$_2$) to give 255 mg (40.7% yield) of an brown-yellow powder. $^1$H NMR (C$_6$D$_6$/THF-d$_8$) δ 6.02 (s, 1, Thiophene: H), 5.23 (s, 1, Thiophene: H), 3.78 (br s, 1, HH'CC(CO$_2$Me)C'HH'), 3.40 and 3.38 (s, 3 each, Thiophene: Me and CO$_2$Me), 2.41 (s, 2, HH'CC(CO$_2$Me)C'HH'), 2.02 (s, 1, HH'CC(CO$_2$Me)CHH').

EXAMPLE 495

Complex 46a. Two equiv (587 mg, 2.11 mmol) of the lithium salt of the ligand were reacted with one equiv (501 mg, 1.05 mmol) of [(allyl)Ni($\mu$-Br)]$_2$ (allyl=H$_2$CC(CO$_2$Me)CH$_2$) to give 765 mg (84.5% yield) of an orange powder. $^1$H NMR spectrum in C$_6$D$_6$ is complex. Peaks consistent with two different isomers of the product are present.

EXAMPLE 496

Complex 47a. Two equiv (607 mg, 2.24 mmol) of the sodium salt of the ligand were reacted with one equiv (303 mg, 1.12 mmol) of [(allyl)Ni($\mu$-Br)]$_2$ (allyl=H$_2$CCHCH$_2$) to give 482 mg (61.8% yield) of a red powder.

EXAMPLE 497

Complex 48a. Two equiv (149 mg, 1.27 mmol) of the sodium salt of the ligand were reacted with one equiv (302 mg, 0.635 mmol) of [(allyl)Ni($\mu$-Br)]$_2$ (allyl=H$_2$CC(CO$_2$Me)CH$_2$) to give 146 mg (45.7% yield) of a red powder.

EXAMPLE 498

Complex 49a. Two equiv (700 mg, 2.17 mmol) of the sodium salt of the ligand were reacted with one equiv (515 mg, 1.08 mmol) of [(allyl)Ni($\mu$-Br)]$_2$ (allyl=H$_2$CC(CO$_2$Me)CH$_2$) to give 779 mg (685.2% yield) of an orange powder. $^1$H NMR spectrum in THF-d$_8$ is complex.

EXAMPLES 499–503

The following complexes of Examples through were synthesized by mixing the protonated form of the hydroxyimine ligand with a base (e.g., pyridine, lutidine, acetonitrile, etc.) in an Et$_2$O solution and cooling this solution to −35° C. The cold Et$_2$O solution was then added to a cold flask containing (tmeda)NiMe$_2$. [For the preparation of (tmeda)NiMe$_2$ please see: Kaschube, W.; Porschke, K. R.; Wilke, G. *J. Organomet. Chem.* 1988, 355, 525–532.] The reaction mixture was stirred for ~4 h. The solution was then filtered though a frit with dry Celite®. The solvent was removed and the product was dried in vacuo.

EXAMPLE 499

Complex 50. One equiv of [2-(OH)-3,5-Cl$_2$—C$_6$H$_2$—C(Me)=NAr [Ar=2,6-(i-Pr)$_2$—C$_6$H$_3$] (356 mg, 0.976 mmol) was reacted with (tmeda)NiMe$_2$ (200 mg, 0.976 mmol) and pyridine (772 mg, 9.76 mmol) to yield an orange-red powder: $^1$H NMR (C$_6$D$_6$) δ 8.66 (d, 2, Py: H$_o$), 7.50 (d, 1, Ar': H), 7.31 (d, 1, Ar': H), 7.09 (m, 3, Ar: H), 6.63 (t, 1, Py: H$_p$), 6.29 (t, 1, Py: H$_m$), 3.98 (septet, 2, CHMe$_2$), 1.68 (d, 6, CHMeMe'), 1.51 (s, 3, N=CMe), 1.04 (d, 6, CHMeMe'), −0.92 (s, 3, NiMe).

EXAMPLE 500

Complex 51. One equiv of [2-(OH)-3,5-Cl$_2$—C$_6$H$_2$—C(Me)=NAr [Ar=2,6-(i-Pr)$_2$—C$_6$H$_3$] (88.8 mg, 0.244 mmol) was reacted with (tmeda)NiMe$_2$ (50 mg, 0.244 mmol) and lutidine (26.2 mg, 0.244 mmol) to yield an orange powder: $^1$H NMR ($C_6D_6$) δ 7.35 (d, 1, Ar': H), 7.28 (d, 1, Ar': H), 7.01 (s, 3, Ar: H), 6.64 (t, 1, Lutidine: $H_p$), 6.28 (d, 2, Lutidine: $H_m$), 3.91 (septet, 2, $CHMe_2$), 3.72 (s, 6, Lutidine: Me), 1.52 (d, 6, CHMeMe'), 1.46 (s, 3, N=CMe), 0.98 (d, 6, CHMeMe'), −1.42 (s, 3, NiMe).

EXAMPLE 501

Complex 52. One equiv of [2-(OH)-3,5-$Cl_2$—$C_6H_2$—C(Me)=NAr [Ar=2,6-(i-Pr)$_2$-$C_6H_3$] (370 mg, 1.02 mmol) was reacted with (tmeda)NiMe$_2$ (209 mg, 1.02 mmol) and acetonitrile (10 mL) to yield a yellow-orange powder: $^1$H NMR ($CD_2Cl_2$) δ 7.23 (d, 1, Ar': H), 7.10 (t, 1, Ar: $H_p$), 7.04 (d, 2, Ar: $H_m$), 6.95 (d, 1, Ar': H), 4.34 (septet, 2, $CHMe_2$), 1.89 (s, 3, N=CMe), 1.70 (s, 3, NC≡Me), 1.33 (d, 6, CHMeMe'), 1.15 (d, 6, CHMeMe'), 0.80 (s, 3, NiMe)

EXAMPLE 502

Complex 53. One equiv of [2-(OH)-3,5-$Cl_2$—$C_6H_2$—C(Me)=NAr [Ar=2,6-(i-Pr)$_2$—$C_6H_3$] (88.8 mg, 0.244 mmol) was reacted with (tmeda)NiMe$_2$ (50 mg, 0.244 mmol) and p-tolunitrile (28.6 mg, 0.244 mmol) to yield a brown powder: $^1$H NMR ($CD_2Cl_2$) δ 7.74 (d, 2, Nitrile: H), 7.23 (d, 1, Ar': H), 7.21 (d, 2, Nitrile: H), 7.10 (t, 1, Ar: $H_p$), 7.04 (d, 1, Ar: $H_m$), 6.95 (d, 1, Ar': H), 4.34 (septet, 2, $CHMe_2$), 2.33 (s, 3, Nitrile: Me), 1.70 (s, 3, N=CMe), 1.33 (d, 6, CHMeMe'), 1.15 (d, 6, CHMeMe'), 0.80 (s, 3, NiMe).

EXAMPLE 503

Complex 54. One equiv of [2-(OH)-3,5-$Br_2$—$C_6H_2$—C(Me)=NAr [Ar=2,6-(i-Pr)$_2$—$C_6H_3$] (111 mg, 0.244 mmol) was reacted with (tmeda)NiMe$_2$ (50 mg, 0.244 mmol) and pyridine (200 mg) to yield a yellow-orange powder: $^1$H NMR ($C_6D_6$) δ 8.77 (d, 2, Py: $H_o$), 7.60 (t, 1, Py: $H_p$), 7.52 (d, 1, Ar': H), 7.44 (d, 1, Ar': H), 7.13 (t, 2, Py: $H_m$), 7.10 (s, 3, Ar: H), 3.85 (septet, 2, $ChMe_2$), 1.82 (s, 3, N=CMe), 1.51 (d, 6, CHMeMe'), 1.07 (d, 6, CHMeMe'), −1.42 (s, 3, NiMe).

EXAMPLES 504–509

General Procedure for Ethylene(28–35 kPa)/α-Olefin Copolymerizations of Table 19

In the drybox, a glass Schlenk flask was loaded with the nickel compound, Lewis acid, solvent, comonomer, and a stir bar. The flask was then capped with a rubber septum and the stopcock was closed prior to removing the flask from the drybox. The flask was then attached to the ethylene line where it was evacuated and backfilled with ethylene. The reaction mixture was stirred under ethylene for the stated reaction time, the ethylene pressure was then released, and the polymer was precipitated by adding the reaction mixture to a solution of MeOH (~100 mL) and concentrated HCl (~1–3 mL). The solid polymer was then collected on a frit and rinsed with MeOH. For amorphous polymers, the MeOH was decanted off of the polymer. Often, the amorphous polymer was dissolved in hexane and reprecipitated in methanol. The polymer was transferred to a pre-weighed vial and dried under vacuum overnight. The polymer yield and characterization were then obtained.

For Example 505 the following quantitative $^{13}$C NMR (TCB, 120–140° C.) was obtained: Branching per 1000 $CH_2$'s; total methyls (98.4), methyl (54.5), ethyl (13.1), propyl (3.2), butyl (14.4), amyl (4.9), hexyl and greater and end of chains (11.1), amyl and greater and end of chains (13.7), butyl and greater and end of chains (27.6)

For Example 506 the following quantitative $^{13}$C NMR (TCB, 120–140° C.) was obtained: Branching per 1000 $CH_2$'s; total methyls (115.4), methyl (61.5), ethyl 12.8), propyl (3.8), butyl (21.3), amyl (4.0), hexyl and greater and end of chains (14.4), amyl and greater and end of chains (16.3), butyl and greater and end of chains (37.2)

TABLE 19

Ethylene/α-Olefin Copolymerizations at 28–35 kPa Ethylene

| Ex. | Cmpd | Lewis Acid (equiv) | Time (h) | Toluene (mL) | Comonomer (mL) | Polymer (g) |
|---|---|---|---|---|---|---|
| 504 | 3a | BPh$_3$/20 | 32 | 30 | 1-Hexene (10) | 0.633 |
| | | Description: Viscous clear oil. $^1$H NMR ($C_6D_6$, rt): 198.2 Total Me/1000 CH$_2$ | | | | |
| 505 | 6a | B($C_6F_5$)$_3$/20 | 24.2 | 30 | 1-Hexene (5) | 7.31 |
| | | Description: Tough, rubbery, amorphous light tan solid. $^1$H NMR ($C_6D_6$, rt): 116.1 Total Me/1000 CH$_2$ | | | | |
| 506 | 6a | B($C_6F_5$)$_3$/20 | 24.2 | 25 | 1-Hexene (10) | 6.26 |
| | | Description: Rubbery, slightly sticky amorphous light tan solid. $^1$H NMR ($C_6D_6$, rt): 129.9 Total Me/1000 CH$_2$ | | | | |
| 507 | 6a | B($C_6F_5$)$_3$/20 | 24.2 | 20 | 1-Hexene (15) | 4.18 |
| | | Description: Sticky, very viscous oil--almost a solid. $^1$H NMR ($C_6D_6$, rt): 167.9 Total Me/1000 CH$_2$ | | | | |
| 508 | 6a | B($C_6F_5$)$_3$/20 | 33.3 | 30 | 1-Octene (5) | 5.65 |
| | | Description: Tough, amorphous rubbery solid. $^1$H NMR ($C_6D_6$, rt): 112.0 Total Me/1000 CH$_2$ | | | | |
| 509 | 9a | B($C_6F_5$)$_3$/20 | 27.3 | 30 | 1-Octene (5) | 7.53 |
| | | Description: Sticky, amorphous light tan solid. $^1$H NMR ($C_6D_6$, rt): 178.7 Me/1000 CH$_2$ | | | | |

EXAMPLES 510–512

General Procedure for Homopolymerizations of 1-Hexene, 1-Octene, and Cyclopentene by Cmpd 6a (Table 20)

In the drybox, the nickel compound, Lewis acid, solvent, monomer and stir bar were placed together in a round bottom flask. The reaction mixture was stirred for the stated amount of time. The flask was removed from the drybox and water and concentrated hydrochloric acid were added. The product was extracted with toluene and/or hexane and the solution was filtered through a frit containing a layer of neutral alumina on top of a layer of silica gel. The solvent was then evaporated and the product was dried in vacuo.

TABLE 20

Ethylene/α-Olefin Copolymerizations at 28–35 kPa Ethylene

| Ex. | Cmpd | Lewis Acid (equiv) | Time (weeks) | Toluene (mL) | Comonomer (mL) | Polymer (g) |
|---|---|---|---|---|---|---|
| 510 | 6a | B($C_6F_5$)$_3$/20 | ~2 | 5 | 1-Hexene (10) | 0.511 |
| | | Description: Viscous oil. $^1$H NMR ($C_6D_6$, rt): 152.2 Total Me per 1000 Carbon Atoms; DP~17.4; $M_n$~1,460 | | | | |
| 511 | 6a | B($C_6F_5$)$_3$/20 | ~2 | 5 | 1-Octene (10) | 1.83 |
| | | Description: Free-flowing, slightly viscous oil. $^1$H NMR ($C_6D_6$, rt): 122.8 Total Me per 1000 Carbon Atoms; DP~10.5; $M_n$~1,180 | | | | |
| 512 | 6a | B($C_6F_5$)$_3$/20 | ~2 | 5 | Cyclopentene (10) | 1.57 |
| | | Description: Partial viscous oil/partial solid. $^1$H NMR ($C_6D_6$) indicates polycyclopentene formation with olefinic end groups present. | | | | |

What is claimed is:
1. A compound of the formula:
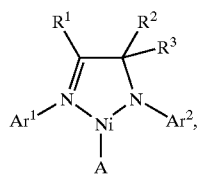
(I)
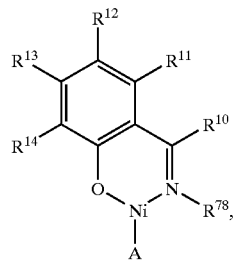
(II)
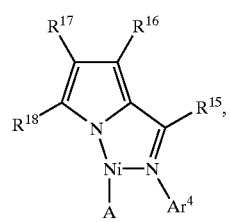
(III)
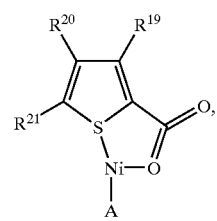
(IV)
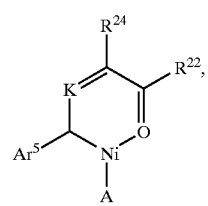
(V)
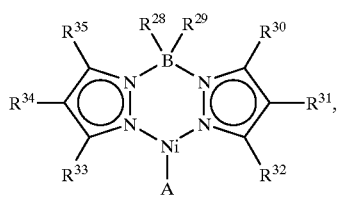
(VI)
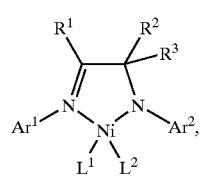
(VII)
-continued
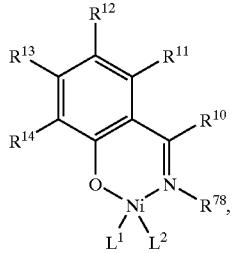
(VIII)
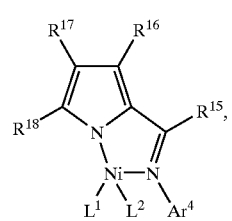
(IX)
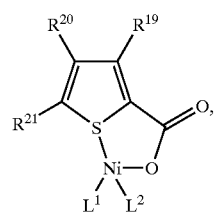
(X)
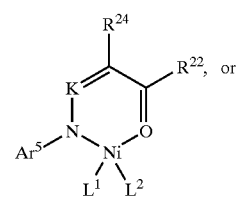
(XI), or
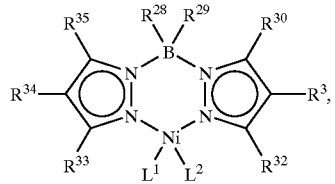
(XII)
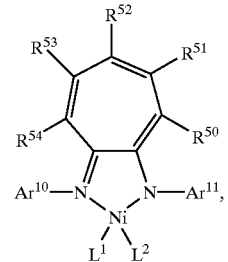
(XIX)
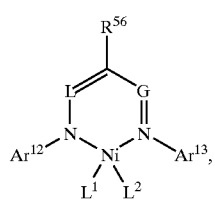
(XXVIII)

-continued

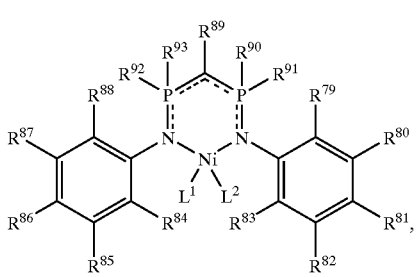
(XXXXI)

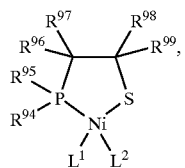
(XXXXII)

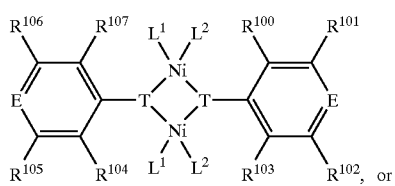
(XXXXIII)

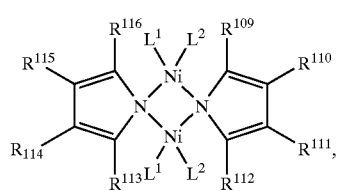
(XXXXIV)

wherein:

A is a π-allyl or π-benzyl group;

$L^1$ is a neutral monodentate ligand which may be displaced by an olefin, and $L^2$ is a monoanionic monodentate ligand, or $L^1$ and $L^2$ taken together are a monoanionic bidentate ligand, provided that said monoanionic monodentate ligand or said monoanionic bidentate ligand may add to said olefin;

$Ar^1$, $Ar^2$, $Ar^4$, $Ar^5$, $Ar^{10}$, $Ar^{11}$, $Ar^{12}$ and $Ar^{13}$ are each independently aryl or substituted aryl;

$R^1$ and $R^2$ are each independently hydrogen, hydrocarbyl, substituted hydrocarbyl, or $R^1$ and $R^2$ taken together form a ring, and $R^3$ is hydrogen, hydrocarbyl or substituted hydrocarbyl or $R^1$, $R^2$ and $R^3$ taken together form a ring;

$R^{10}$ and $R^{15}$ are each independently hydrogen, hydrocarbyl or substituted hydrocarbyl;

$R^{11}$, $R^{12}$, $R^{13}$, $R^{14}$, $R^{16}$, $R^{17}$, $R^{18}$, $R^{19}$, $R^{20}$, $R^{21}$, $R^{30}$, $R^{31}$, $R^{32}$, $R^{33}$, $R^{34}$, $R^{35}$, $R^{50}$, $R^{51}$, $R^{52}$, $R^{53}$ and $R^{54}$ are each independently hydrogen, hydrocarbyl, substituted hydrocarbyl, an inert functional group, and provided that any two of these groups vicinal to one another taken together may form a ring;

K is N or $CR^{27}$;

$R^{22}$ is hydrocarbyl, substituted hydrocarbyl, $-SR^{117}$, $-OR^{117}$, or $-NR^{118}{}_2$, $R^{24}$ is hydrogen, a functional group, hydrocarbyl or substituted hydrocarbyl, and $R^{27}$ is hydrocarbyl or substituted hydrocarbyl, and provided that $R^{22}$ and $R^{24}$ or $R^{24}$ and $R^{27}$ taken together may form a ring;

$R^{117}$ is hydrocarbyl or substituted hydrocarbyl;

each $R^{118}$ is independently hydrogen, hydrocarbyl or substituted hydrocarbyl;

G and L are both N or G is $CR^{57}$ and L is $CR^{55}$;

$R^{55}$, $R^{56}$ and $R^{57}$ are each independently hydrogen, hydrocarbyl or substituted hydrocarbyl, or any two of $R^{55}$, $R^{56}$ and $R^{57}$ taken together form a ring;

$R^{78}$ is hydrocarbyl or substituted hydrocarbyl;

$R^{79}$, $R^{80}$, $R^{81}$, $R^{82}$, $R^{83}$, $R^{84}$, $R^{85}$, $R^{86}$, $R^{87}$, $R^{88}$ and $R^{89}$ are each independently hydrogen, hydrocarbyl, substituted hydrocarbyl, or a functional group;

$R^{90}$, $R^{91}$, $R^{92}$ and $R^{93}$ are each independently hydrocarbyl or substituted hydrocarbyl;

$R^{94}$ and $R^{95}$ are each independently hydrocarbyl or substituted hydrocarbyl;

$R^{96}$, $R^{97}$, $R^{98}$, and $R^{99}$ are each independently hydrogen, hydrocarbyl, substituted hydrocarbyl or a functional group;

both of T are S (sulfur) or NH (amino);

each E is N (nitrogen) or $CR^{108}$ wherein $R^{108}$ is hydrogen, hydrocarbyl, substituted hydrocarbyl or a functional group;

$R^{100}$, $R^{101}$, $R^{102}$, $R^{103}$, $R^{104}$, $R^{105}$, $R^{106}$, and $R^{107}$ are each independently hydrogen, hydrocarbyl, substituted hydrocarbyl, or a functional group;

$R^{109}$, $R^{110}$, $R^{111}$, $R^{112}$, $R^{113}$, $R^{114}$, $R^{115}$ and $R^{116}$ are each independently hydrogen, hydrocarbyl, substituted hydrocarbyl or a functional group; and $R^{28}$ and $R^{29}$ are each independently hydrogen, hydrocarbyl or substituted hydrocarbyl.

2. The compound as recited in claim 1 which is (I) or (VII).

3. The compound as recited in claim 2 wherein:

$R^1$ and $R^2$ are both hydrogen;

$R^3$ is alkyl or aryl containing 1 to 20 carbon atoms, or $R^1$, $R^2$ and $R^3$ taken together are

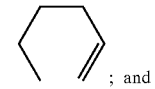
; and $Ar^1$ and $Ar^2$ are each independently

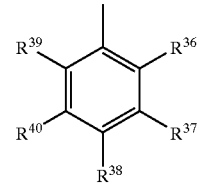
(XIV)

wherein $R^{36}$, $R^{37}$, $R^{38}$, $R^{39}$ and $R^{40}$ are each independently hydrogen, hydrocarbyl, substituted hydrocarbyl or a functional group, provided that any 2 of $R^{36}$, $R^{37}$, $R^{38}$, $R^{39}$ and $R^{40}$ that are vicinal to one another taken together may form a ring.

4. The compound as recited in claim 3 wherein $R^3$ is t-butyl, $R^1$ and $R^2$ are hydrogen, and $R^{36}$ and $R^{39}$ are halo, phenyl, or alkyl containing 1 to 6 carbon atoms.

5. The compound as recited in claim 1 which is (II) or (VIII).

6. The compound as recited in claim 5 wherein:
$R^{10}$ is hydrogen or methyl;
$R^{78}$ is $Ar^3$, which is aryl or substituted aryl; and
$R^{11}$, $R^{12}$, $R^{13}$ and $R^{14}$ are each independently chloro, bromo, iodo, alkyl, alkoxy, hydrogen or nitro, or $R^{11}$ and $R^{12}$ taken together form a 6-membered carbocyclic ring and $R^{13}$ and $R^{14}$ are hydrogen.

7. The compound as recited in claim 1 which is (III) or (IX).

8. The compound as recited in claim 7 wherein:
$R^{15}$, $R^{16}$, $R^{17}$ and $R^{18}$ are hydrogen; and
$Ar^4$ is

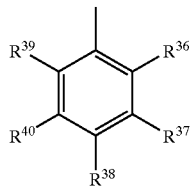

(XIV)

wherein $R^{36}$, $R^{37}$, $R^{38}$, $R^{39}$ and $R^{40}$ are each independently hydrogen, hydrocarbyl, substituted hydrocarbyl or a functional group, provided that any 2 of $R^{36}$, $R^{37}$, $R^{38}$, $R^{39}$ and $R^{40}$ that are vicinal to one another taken together may form a ring.

9. The compound as recited in claim 1 which is (IV) or (X).

10. The compound as recited in claim 9 wherein $R^{19}$, $R^{20}$ and $R^{21}$ are hydrogen, or $R^{19}$ and $R^{20}$ are hydrogen and $R^{21}$ is methyl.

11. The compound as recited in claim 1 which is (V) or (XI).

12. The compound as recited in claim 11 wherein:
K is $CR^{27}$;
$R^{27}$ is hydrogen, hydrocarbyl, substituted hydrocarbyl, or a functional group;
$R^{24}$ is hydrogen, alkyl or halo;
$R^{22}$ is hydrocarbyl or —$OR^{117}$, wherein $R^{117}$ is hydrocarbyl.

13. The compound as recited in claim 12 wherein:
$R^{27}$ is methyl;
$R^{22}$ is phenyl, or —$OR^{117}$, $R^{117}$ is alkyl containing 1 to 6 carbon atoms; and
$R^{24}$ is hydrogen.

14. The compound as recited in claim 1 which is (VI) or (XII).

15. The compound as recited in claim 14 wherein:
$R^{32}$ and $R^{33}$ are both alkyl containing 1 to 6 carbon atoms or phenyl, more preferably isopropyl, $R^{28}$ and $R^{29}$ are both hydrogen or phenyl, and $R^{30}$, $R^{31}$, $R^{34}$ and $R^{35}$ are all hydrogen; or
$R^{31}$ and $R^{32}$ taken together and $R^{33}$ and $R^{34}$ taken together are both a 6-membered aromatic carbocyclic ring having a t-butyl group vicinal to the $R^{32}$ and $R^{33}$ positions, and $R^{28}$ and $R^{29}$ are both hydrogen.

16. The compound as recited in claim 1 which is (XVIII) or (XIX).

17. The compound as recited in claim 16 wherein:
$R^{50}$, $R^{51}$, $R^{52}$, $R^{53}$ and $R^{54}$ are hydrogen; and
$Ar^{10}$ and $Ar^{11}$ are each independently

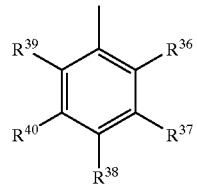

(XIV)

wherein $R^{36}$, $R^{37}$, $R^{38}$, $R^{39}$ and $R^{40}$ are each independently hydrogen, hydrocarbyl, substituted hydrocarbyl or a functional group, provided that any 2 of $R^{36}$, $R^{37}$, $R^{38}$, $R^{39}$ and $R^{40}$ that are vicinal to one another taken together may form a ring.

18. The compound as recited in claim 1 which is (XXVII) or (XXVIII).

19. The compound as recited in claim 18 wherein:
L is $CR^{55}$;
$R^{55}$ is hydrocarbyl, hydrogen, or substituted hydrocarbyl;
G is $CR^{57}$;
$R^{57}$ is hydrocarbyl, hydrogen or substituted hydrocarbyl;
$R^{56}$ is hydrogen; and $Ar^{12}$ and $Ar^{13}$ are each independently

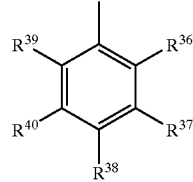

(XIV)

wherein $R^{36}$, $R^{37}$, $R^{38}$, $R^{39}$ and $R^{40}$ are each independently hydrogen, hydrocarbyl, substituted hydrocarbyl or a functional group, provided that any 2 of $R^{36}$, $R^{37}$, $R^{38}$, $R^{39}$ and $R^{40}$ that are vicinal to one another taken together may form a ring.

20. The compound as recited in claim 19 wherein $R^{55}$ and $R^{57}$ are both alkyl or fluorinated alkyl, and $Ar^{12}$ and $Ar^{13}$ are both 2,6-diisopropylphenyl.

21. The compound as described in claim 1 which is (XXXVII) or (XXXXI).

22. The compound as recited in claim 21 wherein: $R^{79}$, $R^{80}$, $R^{81}$, $R^{82}$, $R^{83}$, $R^{84}$, $R^{85}$, $R^{86}$, $R^{87}$, $R^{88}$ and $R^{89}$ are each independently hydrogen or alkyl; and
$R^{90}$, $R^{91}$, $R^{92}$ and $R^{93}$ are each independently hydrocarbyl.

23. The compound as described in claim 1 which is (XXXVIII) or (XXXII).

24. The compound as recited in claim 23 wherein:
$R^{94}$ and $R^{95}$ are each independently hydrocarbyl; and
$R^{96}$, $R^{97}$, $R^{98}$, and $R^{99}$ are each independently hydrogen or hydrocarbyl.

25. The compound as recited in claim 1 which is (XXXIX) or (XXXXIII).

26. The compound as recited in claim 25 wherein:
E is N or $CR^{108}$;
$R^{108}$ is hydrogen or hydrocarbyl; and
$R^{100}$, $R^{101}$, $R^{102}$, $R^{103}$, $R^{104}$, $R^{105}$, $R^{106}$, and $R^{107}$ each independently hydrogen, hydrocarbyl, or halo.

27. The compound as recited in claim 1 which is (XXXX) or (XXXXIV).

28. The compound as recited in claim 27 wherein $R^{109}$, $R^{110}$, $R^{111}$, $R^{112}$, $R^{113}$, $R^{114}$, $R^{115}$, $R^{116}$ are each independently hydrogen or hydrocarbyl.

29. The compound as recited in claim 1 wherein $L^1$ is a nitrile, pyridine, or a substituted pyridine, and $L^2$ is methyl.

30. The compound as recited in claim 1 wherein $L^1$ and $L^2$ taken together are not π-allyl or π-benzyl.

31. A compound of the formula

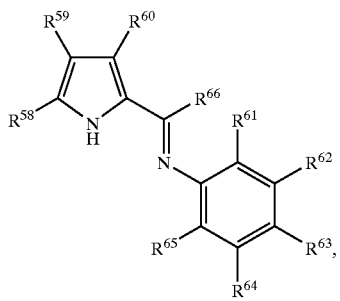

(XXXIII)

wherein:

$R^{58}$, $R^{59}$, $R^{60}$, $R^{62}$, $R^{63}$ and $R^{64}$ are each independently hydrogen, hydrocarbyl, substituted hydrocarbyl, or a functional group, and provided that any two of these groups vicinal to one another taken together may form a ring, or if vicinal to $R^{61}$ or $R^{65}$ form a ring with them;

$R^{66}$ is hydrogen, hydrocarbyl or substituted hydrocarbyl; and $R^{61}$ and $R^{65}$ are each independently hydrocarbyl containing 2 or more carbon atoms, or substituted hydrocarbyl containing 2 or more carbon atoms, and provided that $R^{61}$ and $R^{65}$ may form a ring with any group vicinal to it.

32. The compound as recited in claim 29 wherein;

$R^{58}$, $R^{59}$, and $R^{60}$ are hydrogen;

$R^{66}$ is hydrogen;

$R^{61}$ and $R^{65}$ are each independently alkyl containing 2 or more carbon atoms; and $R^{62}$, $R^{63}$ and $R^{64}$ are hydrogen.

33. A compound of the formula

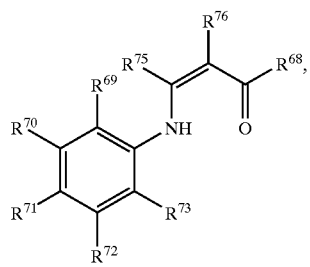

(XXXVI)

wherein:

$R^{66}$ is hydrocarbyl, substituted hydrocarbyl, —$SR^{117}$, —$OR^{117}$, or —$NR^{118}{}_2$, $R^{76}$ is hydrogen, a functional group, hydrocarbyl or substituted hydrocarbyl, and $R^{75}$ is hydrocarbyl or substituted hydrocarbyl, and provided that $R^{68}$ and $R^{76}$ or $R^{75}$ and $R^{76}$ taken together may form a ring;

$R^{117}$ is hydrocarbyl or substituted hydrocarbyl;

each $R^{118}$ is independently hydrogen, hydrocarbyl or substituted hydrocarbyl;

$R^{70}$, $R^{71}$ and $R^{72}$ are each independently hydrogen, hydrocarbyl, substituted hydrocarbyl or a functional group;

$R^{69}$ and $R^{73}$ are hydrocarbyl containing 3 or more carbon atoms, substituted hydrocarbyl containing 3 or more carbon atoms or a functional group;

and provided that any two of $R^{70}$, $R^{71}$, $R^{72}$, $R^{69}$ and $R^{73}$ vicinal to one another together may form a ring.

34. The compound as recited in claim 33 wherein:

$R^{68}$ is —$OR^{117}$ or aryl;

$R^{75}$ is hydrocarbyl or substituted hydrocarbyl; and $R^{76}$ is hydrogen, hydrocarbyl, substituted hydrocarbyl or a functional group.

35. The compound as recited in claim 34 wherein $R^{76}$ is hydrogen, hydrocarbyl or substituted hydrocarbyl.

* * * * *